US010610535B2

(12) United States Patent
Voskuhl

(10) Patent No.: US 10,610,535 B2
(45) Date of Patent: Apr. 7, 2020

(54) DIARYLPROPIONITRILE THERAPY FOR TREATMENT OF MULTIPLE SCLEROSIS

(71) Applicant: The Regents of the University of California, Oakland, CA (US)

(72) Inventor: Rhonda R. Voskuhl, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/685,156

(22) Filed: Aug. 24, 2017

(65) Prior Publication Data

US 2018/0161346 A1    Jun. 14, 2018

Related U.S. Application Data

(63) Continuation of application No. 14/333,027, filed on Jul. 16, 2014, now abandoned, which is a continuation of application No. 13/722,672, filed on Dec. 20, 2012, now abandoned, which is a continuation of application No. 11/992,558, filed as application No. PCT/US2006/037259 on Sep. 26, 2006, now abandoned.

(60) Provisional application No. 60/833,527, filed on Jul. 26, 2006, provisional application No. 60/720,971, filed on Sep. 26, 2005.

(51) Int. Cl.
    *A61K 31/57*    (2006.01)
    *A61K 31/565*   (2006.01)

(52) U.S. Cl.
    CPC ............ *A61K 31/57* (2013.01); *A61K 31/565* (2013.01)

(58) Field of Classification Search
    None
    See application file for complete search history.

(56) References Cited

U.S. PATENT DOCUMENTS

| | | | |
|---|---|---|---|
| 3,932,635 A | 1/1976 | Segre | |
| 4,826,831 A | 5/1989 | Plunkett et al. | |
| 5,108,995 A | 4/1992 | Casper | |
| 5,200,197 A | 4/1993 | Wright et al. | |
| 5,554,601 A | 9/1996 | Simpkins et al. | |
| 6,013,642 A | 1/2000 | Foulkes et al. | |
| 6,043,236 A | 3/2000 | Brattsand et al. | |
| 6,214,791 B1 | 4/2001 | Arnon et al. | |
| 6,936,599 B2 | 8/2005 | Voskuhl | |
| 8,372,826 B2 | 2/2013 | Voskuhl | |
| 8,658,627 B2 | 2/2014 | Voskuhl | |
| 8,895,539 B2 | 11/2014 | Voskuhl | |
| 9,168,262 B2 | 10/2015 | Voskuhl | |
| 9,452,175 B2 | 9/2016 | Voskuhl | |
| 2001/0016325 A1 | 8/2001 | Mobley et al. | |
| 2002/0164314 A1 | 11/2002 | Weiss et al. | |
| 2002/0183299 A1 | 12/2002 | Voskuhl | |
| 2004/0229800 A1 | 11/2004 | Gold | |
| 2005/0209208 A1 | 9/2005 | Murase et al. | |
| 2005/0239758 A1 | 10/2005 | Roby | |
| 2005/0239762 A1 | 10/2005 | Voskuhl | |
| 2009/0005351 A1 | 1/2009 | Pickar et al. | |
| 2009/0297477 A1 | 12/2009 | Voskuhl | |
| 2010/0168071 A1 | 7/2010 | Boissonneault | |
| 2011/0256096 A1 | 10/2011 | Voskuhl et al. | |
| 2012/0282222 A9 | 11/2012 | Voskuhl et al. | |
| 2012/0328566 A9 | 12/2012 | Voskuhl | |
| 2013/0203722 A1 | 8/2013 | Voskuhl | |
| 2015/0051178 A1 | 2/2015 | Voskuhl | |
| 2016/0082017 A1 | 3/2016 | Voskuhl | |
| 2018/0162827 A1 | 6/2018 | McBride et al. | |

FOREIGN PATENT DOCUMENTS

| | | |
|---|---|---|
| AU | 2004257772 A1 | 1/2005 |
| JP | 2003522737 A | 7/2003 |
| JP | 2003246736 A | 9/2003 |
| WO | WO-1995/012402 A1 | 5/1995 |
| WO | WO-1997/008188 A1 | 3/1997 |
| WO | WO-1999/048502 A1 | 9/1999 |
| WO | WO-2001/070208 A2 | 9/2001 |
| WO | WO-2001/085154 | 11/2001 |
| WO | WO-2002/085374 | 10/2002 |
| WO | WO-2002/092102 A2 | 11/2002 |
| WO | WO-2002/092102 A3 | 11/2002 |
| WO | WO-2003/072109 | 9/2003 |
| WO | WO-2003/072110 | 9/2003 |
| WO | WO-2006/053172 A2 | 5/2006 |
| WO | WO-2007/038435 A2 | 4/2007 |

(Continued)

OTHER PUBLICATIONS

Itoh et al., Journal of Neuroimmunology, 2017; 304: 63-71 (Year: 2017).*
't Hart et al., The Lancet Neurology 3(10):588-597, Oct. 2004 (Year: 2004).*
Werkerle et al., Drug Discovery Today: Disease Models 3(4):359-367, 2006 (Year: 2006).*
Lund et al., Endocrinology, 2005; 146: 797-807. (Year: 2005).*
Abramsky, "Pregnancy and multiple sclerosis." Annals of Neurology, 36 Suppl: S38-41 (1994).
Aharoni et al., "Bystander suppression of experimental autoimmune encephalomyelitis by T cell lines and clones of the Th2 type induced by copolymer I," J Neuroimmunol, 91:135-46 (1998).
Ando et al., "Encephalitogenic T cells in the BIO.PL model of experimental allergic encephalomyelitis (EAE) are of the Th1 lymphokine subtype," Cell Immunol, 124:132-43 (1989).

(Continued)

*Primary Examiner* — Christina M Borgeest
(74) *Attorney, Agent, or Firm* — Foley Hoag LLP; David P. Halstead; Alexander J. Chatterley

(57) ABSTRACT

The present invention discloses administering steroid hormones to mammals to treat autoimmune related diseases, including post-partum auto immune diseases. Most preferably the invention uses estrogens, estranges, estriol or estrogen receptor active agents to prevent or ameliorate clinical symptoms of these Th1-mediated (cell-mediated) autoimmune diseases known to either have an initial onset following the birth of a child or which are exacerbated in patients in the post-partum period.

21 Claims, 21 Drawing Sheets

(56) References Cited

FOREIGN PATENT DOCUMENTS

| WO | WO-2007/038636 A2 | 4/2007 |
|---|---|---|
| WO | WO-2010/050916 A1 | 5/2010 |
| WO | WO-2013/017619 A1 | 2/2013 |
| WO | WO-2015/168000 A1 | 11/2015 |
| WO | WO-2015/168002 A1 | 11/2015 |
| WO | WO-2016/036719 A1 | 3/2016 |
| WO | WO-2016/036721 A1 | 3/2016 |
| WO | WO-2016/053946 A1 | 4/2016 |

OTHER PUBLICATIONS

Asthana et al., "High-dose estradiol improves cognition for women with AD: results of a randomized study," Neurology, 57:605-12 (2001).
Baker, "What are the physiological estrogens?" Steroids, 78:337-40 (2013).
Balashov et al., "Defective regulation of IFNgamma and IL-12 by endogenous IL-IO in progressive MS," Neurology, 55:192-8 (2000).
Barkhof et al., "T(1) hypo intense lesions in secondary progressive multiple sclerosis: effect of interferon beta-l b treatment," Brain, 124:1396-1402 (2001).
Barkley et al., "Equol: a contributor to enigmatic immunoassay measurements of estrogen," Steroids, 46:587 (1985).
Bebo et al., "Low-dose estrogen therapy ameliorates experimental autoimmune encephalomyelitis in two different inbred mouse strains," J Immunol, 166(3):2080-9 (2001).
Becker et al., "Immunotherapy in Multiple Sclerosis," Am J Health Sys Pharmacy, 52(19):2105-20 (1995).
Behl et al., "17-Beta estradiol protects neurons from oxidative stress-induced cell death in vitro," Biochem Biophys Res Comm, 216:473-82 (1995).
Behl et al., "Neuroprotection against oxidative stress by estrogens: Structure-activity relationship," Mol Pharmacol, 51:535-41 (1997).
Biewenga et al., "Estradiol and raloxifene protect cultured SN4741 neurons against oxidative stress," Neurosci Lett, 373:179-83 (2005).
Bijisma et al., "Estrogens and rheumatoid arthritis," Am J Reproductive Immunol, 28:231-4 (1992).
Birk et al., "Pregnancy and Multiple Sclerosis," Semin Neurol, 8(3):205-13 (1988).
Birk et al., "The clinical course of Multiple Sclerosis during pregnancy and the puerperium," Arch Neurol, 47:738-42 (1990).
Bongioanni et al., "Systemic high-dose recombinant-alpha-2a-interferon therapy modulates lymphokine production in Multiple Sclerosis," J Neurol Sci, 143(1-2):91-9 (1996).
Boothman, "Interferon beta: The current position," Brit J Hospital Med, 57(6):277-80 (1997).
Boumpas et al., "Systemic lupus erythematosus: Emerging concepts," Ann Internal Med, 123:42-53 (1995).
Brinton, "Estrogen regulation of glucose metabolism and mitochondrial function: Therapeutic implications for prevention of Alzheimer's disease," Adv Drug Deliver Rev, 60:1504-11 (2008).
Brod et al., "Interferon-beta lb treatment decreases tumor necrosis factor-beta and increases interleukin-6 production in Multiple Sclerosis," Neurology, 46(6):1633-8 (1996).
Brod et al., "Multiple Sclerosis: Clinical presentation, diagnosis and treatment," Am Fam Physician, 54(4):1301-6, 1309-11 (1996).
Brostoff, et al., "Results of a Phase lClinical Trial of a T-Cell Receptor Peptide Vaccine in Patients with Multiple Sclerosis, I, Analysis of T-Cell Receptor Utilization in CSF Cell Populations," J Neuroimmunologyn, 76(1-2): 15-28 (1997).
Buyon et al., "The effect of combined estrogen and progesterone hormone replacement therapy on disease activity in systemic lupus erythematosus: A randomized trial," Ann Internal Med, 142(12, part 1):953-62 (Jun. 2005).
Cannella et al., "IL-10 fails to abrogate experimental autoimmune encephalomyelitis," J Neurosci Res, 45:735-46 (1996).
Cardozo et al., "Oestriol in the treatment of postmenopausal urgency: A multicentre study," Maturitas, 18(1):47-53 (1993).
Carswell et al., "Neuroprotection by a selective estrogen receptor B agonist in a mouse model of global ischemia," Am J Physiol-Heart C, 287:H1501-H1504 (2004).
Cheng et al., "Nylestriol replacement therapy in postmenopausal women," Chinese Med J, 106:911-6 (1993).
Cho et al., "The role of the estrogen neuroprotection: Implications for neurodegenerative diseases," Neuroendocrinol Lett, 24:141-7 (2003).
Comi et al., "European/Canadian multicenter, double-blind, randomized, placebo-controlled study of the effects of glatiramer acetate on magnetic resonance imaging-measured disease activity and burden in patients with relapsing Multiple Sclerosis," Ann Neurol, 49:290-7 (2001).
Confavreux et al., "Rate of pregnancy-related relapse in Multiple Sclerosis," New England J Med, 339:285-91 (1998).
Correale et al., "Steroid hormone regulation of cytokine secretion by proteolipid protein-specific CD4+ T cell clones isolated from Multiple Sclerosis patients and normal control subjects," J Immunol, 161:3365-74 (1998).
Crisi et al., "*Staphylococcal enterotoxin* band tumor-necrosis factor-alpha-induced relapses of experimental allergic encephalomyelitis: Protection by transforming growth factor-beta and interleukin-IO," Eur J Immunol, 25:3035-40 (1995).
Croxford et al., "Mouse models for multiple sclerosis: Historical facts and future implications," Biochimica Biophysica Acta, 1812:177-83 (2011).
Cutolo, "Sex hormone adjuvant therapy in rheumatoid arthritis," Neuroendocrine Mech Rheum Dis, 26:881-95 (2000).
Da Silva et al., "The effects of gender and sex hormones on outcome in rheumatoid arthritis," Baillieres Clin Rheumatol, 6:196-219 (1992).
Da Silva et al., "The role of pregnancy in the course and aetiology of rheumatoid arthritis," Clin Rheumatol, 189-94 (1992).
Damek et al., "Pregnancy and Multiple Sclerosis," Mayo Clinic Proc, 72:977-89 (1997).
DeGroot, et al., Endocrinology, 3(9): 2171-2223 (1994).
Delassus et al., "Differential cytokina expression in maternal blood and placenta during murine gestation," J Immunol, 152:2411-20 (1994).
Draca, "Estriol and progesterone: A new role for sex hormones," Int J Biomed Sci, 2(4):305-7 (2006).
Drake et al., "Associations between circulating sex steroid hormones and cognition in normal elderly women," Neurology, 54:599-603 (2000).
Drew et al., "Female sex steroids: Effects upon microglial cell activation," J Neuroimmunol, 111:77-85 (2000).
Drossaers-Bakker et al., "Pregnancy and oral contraceptive use do not significantly influence outcome in long term rheumatoid arthritis," Ann Rheum Dis, 61:405-8 (2002).
Du et al., "Administration of dehydroepiandrosterone suppresses experimental allergic encephalomyelitis in EJL/J mice," J Immunol, 7094-101 (2001).
Duda et al., "Glatiramer acetate (Copaxone) induces degenerate, Th2-polarized immune responses in patients with Multiple Sclerosis," J Clin Invest, 105:967-76 (2000).
El-Etr et al., "Steroid hormones in Multiple Sclerosis," J Neurol Sci, 233(1-2):49-54 (2005).
Elloso et al., "Suppression of experimental autoimmune encephalomyelitis using estrogen receptor-selective ligands," J Endocrinol, 185:243-52 (2005).
Follingstad et al., "Estriol, the forgotten estrogen?" JAMA, 239:29-30 (1978).
Fornari et al., "Demyelination of superficial white matter in early Alzheimer's disease: a magnetization transfer imaging study," Neurobiol Aging, 33:428.e7-428.e19 (2012).
Fritzemeier et al., "Analysis of the effects of ERbeta on ERalpha transcriptional activity using isoptope selective ligands," Exp Clin Endocrinol Diabetes, 109:S57 (2001).
Galea et al., "Estradiol alleviates depressive-like symptoms in a novel animal model of postpartum depression," Behavioural Brain Res, 122(1):1-9 (2001).

(56) References Cited

OTHER PUBLICATIONS

Gelinas et al., "Alpha and beta estradiol protect neuronal but not active PC12 cells from paraquat-induced oxidative stress," Neurotox Res, 6:141-8 (2004).
Gilmore et al., "Effect of estradiol on cytokine secretion by proteolipid protein-specific Tcell clones isolated from multiple sclerosis patients and normal control subjects," J Immunol, 158:446-51 (1997).
Gold et al., "Estrogen treatment in multiple sclerosis," J Neurol Sci, 286(1-2):99-103 (2009).
Gomez-Mancilla et al., "Effect of estrogen and progesterone on L-DOPA induced dyskinesia in MPTP-treated monkeys," Neurosci Lett, 135:129-32 (1992).
Hall et al., "A randomised controlled trial of the effect of hormone replacement therapy on disease activity in postmenopausal rheumatoid arthritis," Ann Rheum Dis, 53(2):112-6 (1994).
Hall et al., "Beta-interferon and Multiple Sclerosis," Trends Neurosci, 20:63-7 (1997).
Harms et al., "Differential mechanisms of neuroprotection by 17 beta-estradiol in apoptopic versus necrotic neurodegeneration," J Neurosci, 21:2600-9 (2001).
Harrington et al., "Activities of estrogen receptor alpha- and beta-selective ligands at diverse estrogen responsive gene sites mediating transactivation or transrepression," Mol Cell Endocrinol, 29:13-22 (2003).
Hauptmann et al., "Concepts for the syntheses of biotinylated steroids. Part II: 17b-estradiol derivatives as immunochemical probes," Bioconjugate Chem, 11:537-48 (2000).
Head, "Estriol: Safety and efficacy," Alt Med Rev, 3:101-13 (1998).
Hernan et al., "Oral contraceptives and the incidence of Multiple Sclerosis," Neurology, 55(6):848-54 (2000).
Hill et al., "T-helper I-type immunity to trophoblast in women with recurrent spontaneous abortion," JAMA, 273:1933-6 (1995).
Hofbauer et al., "Oral contraceptives that contain ethinyl estradiol (0.035 mg) and cyproterone acetate (2 mg) inhibit leukocyte trans-migration through endothelial cell monolayers," Fertility Sterility, 72(4):652-6 (1999).
Hunter et al., "Rational clinical immunotherapy for Multiple Sclerosis," Mayo Clinic Proc, 72(8):765-80 (1997).
International Preliminary Examination Report in PCT/US2002/013407 dated Nov. 14, 2003.
International Preliminary Report on Patentability and Written Opinion in PCT/US2006/037752 dated Apr. 3, 2008.
International Preliminary Report on Patentability for PCT/US2008/012353 dated May 3, 2011.
International Preliminary Report on Patentability in PCT/US2006/037259 dated Apr. 3, 2008.
International Search Report and Written Opinion for PCT/US2006/037259 dated Mar. 28, 2007.
International Search Report and Written Opinion for PCT/US2006/037752 dated Sep. 25, 2007.
International Search Report and Written Opinion for PCT/US2008/012353 dated Feb. 6, 2009.
International Search Report for PCT/US2002/013407 dated Aug. 22, 2002.
International Search Report of the International Searching Authority, dated Aug. 3, 2015, from related International Application No. PCT/US2015/027756.
International Search Report of the International Searching Authority, dated Jan. 3, 2016, from related International Application No. PCT/US2015/047909.
International Search Report of the International Searching Authority, dated Aug. 5, 2015, from related International Application No. PCT/US2015/027752.
International Search Report of the International Searching Authority, dated Jan. 10, 2016, from related International Application No. PCT/US2015/047906.
International Search Report of the International Searching Authority, dated Dec. 24, 2015, from related International Application No. PCT/US2015/052805.

International Written Opinion for PCT/US2002/013407 dated Jan. 16, 2003.
Ito et al., "Estrogen treatment down regulates TNF-alpha production and reduces the severity of experimental autoimmune encephalomyelitis in cytokine knockout mice," J Immunol, 167(1):542-52 (2001).
Jacobs et al., "Appropriate use of interferon beta-1a in Multiple Sclerosis," BioDrugs, 11:155-63 (1999).
Jacobs et al., "Intramuscular interferon beta-1a therapy initiated during a first demyelinating event in Multiple Sclerosis," New England J Med, 343:898-904 (2000).
Janeway et al., "Signals and signs for lymphocyte responses," Cell, 576:275-85 (1994).
Jansen et al., "Increased T cell expression of COI 54 (CD4O-ligand) in Multiple Sclerosis," Eur J Neurol, 8:321-8 (2001).
Jansson et al., "Estrogen induced suppression of collagen arthritis. V: Physiological level of estrogen in DBAII mice is therapeutic on established arthritis, suppresses anti-type II collagen T cell dependent immunity and stimulates polyclonal B-cell activity," J Autoimmunity, 3:257 (1990).
Jansson et al., "Estrogen induces a potent suppression of experimental autoimmune encephalomyelitis and collagen-induced arthritis in mice," J Neuroimmunol, 53(2):203-7 (1994).
Jansson et al., "Estrogen-mediated immunosuppression in autoimmune diseases," Inflamm Res, 47:290-301 (1998).
Jansson et al., "Oestrogen induced suppression of collagen arthritis. IV: Progesterone alone does not affect the course of arthritis but enhances the oestrogen-mediated therapeutic effect," J Reprod Immunol, 15:141-50 (1989).
Johnson, et al., Neurology, 50: 701-708 (1998).
Jourdain et al., "Oestrogens prevent loss of dopamine transporter (OAT) and vesicular monoamine transporter (VMAT2) in substantia nigra of 1-methyl-4-phenyl-1,2,3,6-tetrahydropyridine mice," J Neuroendocrinol, 17:509-17 (2005).
Jover et al., "Estrogen protects against global ischemia-induced neuronal death and prevents activation of apoptotic signaling cascades in the hippocampal CA 1," J Neurosci, 22:2115-24 (2002).
Jungers et al., "Influence of oral contraceptive therapy on the activity of systemic lupus erythematosus," Arthritis Rheumatism, 25:618-23 (1982).
Kallmann et al., "What is new in MS treatment?" Aktuelle Neurologie, 30(9):421-27 (2003).
Kassi et al., "Molecular analysis of estrogen receptor alpha and beta in lupus patients," Eur J Clin Investig, 31:86-93 (2001).
Katzenellenbogen, "Biology and receptor interactions of estriol and estriol derivatives in vitro and in vivo," J Steroid Biochem, 20:1033-7 (1984).
Kenchappa et al., "Estrogen and neuroprotection: higher constitutive expression of glutaredoxin in female mice offers protection against MPTP-mediated neurodegeneration," FASEB J, 18:1102-4 (2004).
Kennedy et al., "Analysis of cytokine mRNA expression in the central nervous system of mice with experimental autoimmune encephalomyelitis receals that IL-10 mRNA expression correlates with recover," J Immunol, 149:2496-505 (1992).
Kent et al., "Oral administration of myelin induces antigen-specific TGF beta I-secreting T cells in Multiple Sclerosis patients," Ann NY Acad Sci, 815:412-22 (1997).
Kim et al., "Estriol ameliorates autoimmune demyelinating disease," Neurology, 52(6):1230-6 (1999).
Kim et al., "Mechanisms in the shift toward TH2 during pregnancy: A role for estriol treatment of TH1 mediated disease," FASEB J, 12(4):A616 (1998).
Kirkengen et al., "Oestriol in the prophylactic treatment of recurrent urinary tract infections in postmenopausal women," Scandinavian J Primary Health Care, 10:139-42 (1992).
Kishi et al., "Estrogen promotes differentiation and survival of dopaminergic neurons derived from human neural stem cells," J Neurosci Res, 79:279-86 (2005).
Koloszar et al., "Treatment of climacteric urogenital disorders with an estriol-containing ointment," Orvosi Hetilap, 136(7):343-5 (1995).
Kozovska et al., "Interferon beta induces T-helper 2 immune deviation in MS," Neurology, 53:1692-7 (1999).

(56) References Cited

OTHER PUBLICATIONS

Krishnan et al., "Pregnancy impairs resistance of C57BL/6 mice to leishmania major infection and causes decreased antigen-specific IFN-responses and increased production of T helper 2 cytokines," J Immunol, 156:644-52 (1996).
Krishnan et al., "T-Helper I response against leishmania major in pregnant C57BL/6 mice increases implantation failure and fetal reabsorptions: Correlation with increased IFN and TNF and reduced IL-10 production by placental cells," J Immunol, 156:653-62 (1996).
Kuchroo et al., "Cytokines and adhesion molecules contribute to the ability of myelin proteolipid protein-specific T cell clones to mediate experimental allergic encephalomyelitis," J Immunol, 151:4371-82 (1993).
Kuiper et al., "Comparison of the ligand binding specificity and transcript tissue distribution of estrogen receptors a and b," Endocrinol, 138(3):863-70 (1997).
Kumar et al., "Role of nonfeminizing estrogen analogues in neuroprotection of rat retinal ganglion cells against glutimate-induced cytotoxicity," Free Radical Biol Med, 38(9):1152-63 (2005).
Kurman et al., "Norethindrone acetate and estradiol-induced endometrial hyperplasia," Obstetrics Gynecol, 96(3):373-9 (2000).
Langer-Gould et al., "Sex hormones and multiple sclerosis: another informative failure," Lancet Neurol, 15(1): 22-23 (2016).
Lauritzen, "Results of a 5 years prospective study of estriol succinate treatment in patients with climacteric complaints," Hormone Metabolic Res, 19:579-84 (1987).
Lauritzen, "The female climacteric syndrome: Significance, problems, treatment," Acta Obstetricia et Gynecologica Scandinavica, 51(suppl.):49-61 (1976).
Lauritzen, "The management of the premenopausal and the post-menopausal patient," Frontiers Hormone Res, 2:2-21 (1973).
Lee et al., "Neurotrophic and neuroprotective actions of estrogens and their therapeutic implications," Ann Rev Pharmacol Toxicol, 41:569-91 (2001).
Lemon, "Estriol prevention of mammary carcinoma induced by 7,12-dimethylbenzanthracene and procarbazine," Cancer Res, 35:1341-53 (1975).
Lemon, "Oestriol and prevention of breast cancer," The Lancet, 1:547 (1973).
Leranth et al., "Estrogen is essential for maintaining nigrostriatal dopamine neurons in primates: Implications for Parkinson's disease and memory," J Neurosci, 20:8604-9 (2000).
Li et al., "Estrogen and brain: Synthesis, function and diseases," Frontiers Biosci, 10:257-67 (2005).
Li et al., "Randomized controlled trial of interferon-beta-1a in secondary progressive MS: MRI results," Neurology, 56:1505-13 (2001).
Lin et al., "Synthesis of T helper 2-type cytokines at the maternal-fetal interface," J Immunol, 151:4562-73 (1993).
Liva et al., "Testosterone acts directly on CD4+ T-lymphocytes to increase ILIO production," J Immunol, 167:2060-7 (2001).
MacKenzie-Graham et al., "Estrogen treatment prevents gray matter atrophy in experimental autoimmune encephalomyelitis," J Neurosci Res, 90(7):1310-23 (2012).
Maki et al., "Enhanced verbal memory in nondemented elderly women receiving hormone-replacement therapy," Am J Psychiat, 158:227-33 (2001).
Maki et al., "Implicit memory varies across the menstrual cycle: Estrogen effects in young women," Neuropsychol, 40:518-29 (2002).
Margolis et al., "Effect of oestrogen plus progestin on the incidence of diabetes in postmenopausal women: Results from the Women's Health Initiative Hormone Trial," Diabetologia, 47(7):1175-87 (2004).
Martin et al., "Immunological aspects of demyelinating diseases," Ann Rev Immunol, 10:1534-87 (1992).
Marzi et al., "Characterization of type 1 and type 2 cytokine production profile in physiologic and pathologic pregnancy," Clin Exp Immunol, 106:127-33 (1996).

Matejuk et al., "17beta-estradiol inhibits cytokine, chemokine chemokine receptor mRNA expression in the central nervous system of female mice with experimental autoimmune encephalomyelitis," J Neurosci Res, 65:529-42 (2001).
Mattsson et al., "Maintained pregnancy levels of oestrogen afford complete protection from post-partum exacerbation of collagen-induced arthritis," Clin Exp Immunol, 85:41-7 (1991).
McDonald et al., "Recommended diagnostic criteria for Multiple Sclerosis: Guidelines from the International Panel on the Diagnostic of Multiple Sclerosis," Ann Neurology, 50(1):121-7 (2001).
McFarland et al., "Using gadolinium-enhanced magnetic resonance imaging lesions to monitor diease activity in Multiple Sclerosis," Ann Neurology, 32:758-66 (1992).
Miller et al., "Guidelines for the use of magnetic resonance techniques in monitoring the treatment of Multiple Sclerosis," Ann Neurology, 39:6-16 (1996).
Milner, "Understanding the molecular basis of cell migration; Implications for clinical therapy in Multiple Sclerosis," Clin Sci, 92(2):113-22 (1997).
Minaguchi et al., "Effect of estriol on bone loss in postmenopausal Japanese women: A multicenter prospective open study," J Obstetrics Gynaecol Res, 22(3):259-65 (1996).
Morissette, et al., "Oestrogens Prevent Loss of Dopamine Transporter (OAT) and Vesicular Monoamine Transporter (VMAT2) in Substantia Nigra of 1-Methyl-4-Phenyl-1,2,3,6-Tetrahydropyridine Mice," J Neuroendocrinology, 17: 509-517 (2005).
Mosselman et al., "ER beta: Identification and characterization of a novel human estrsogen receptor," FEBS Lett, 392:49-53 (1996).
Murphy et al., "Estradiol increases dendritic spine density by reducing GABA neurotransmission in hippocampal neurons," J Neurosci, 18:2550-9 (1998).
Murray et al., "Major histocompatibility complex regulation of T helper functions mapped to a peptide C terminus that controls ligand density," Eur J Immunol, 24:2337-44 (1994).
Nelson et al., "Maternal-fetal disparity in HLA class II alloantigens and the pregnancy-induced amelioration of rheumatoid arthritis," New England J Med, 329:466-71 (1993).
Nelson et al., "Remission of rheumatoid arthritis during pregnancy and maternal-fetal class II alloantigen disparity," Am J Reprod Immunol, 28:226-7 (1992).
Nishibe et al., "Effect of estriol and bone mineral density of lumbar vertebrae in elderly and postmenopausal women," JPN J Geriatr, 33(5):353-9 (1996).
Noelle, "CD40 and its ligand in host defense," Immunity, 4:415-9 (1996).
Office Action for Canadian Patent Application No. 2,623,839 dated Nov. 17, 2011.
Office Action for European Patent Application No. 02729034 dated Jul. 22, 2005.
Office Action for European Patent Application No. 02729034 dated Oct. 11, 2007.
Offner et al., "Estrogen potentiates treatment with T-cell receptor protein of female mice with experimental encephalomyelitis," J Clin Investig, 105:1465-72 (2000).
Offner et al., "Estrogen potentiates treatment with TCR protein of female mice with experimental encephalomyelitis," Int J Mol Med, Joint Meeting of the 5th World Congress on Advances in Oncology and the 3rd International Symposium on Molecular Medicine, Oct. 19-21, 2000; vol. 6(Suppl.1):58.
Offner, "Neuroimmunoprotective effects of estrogen and derivatives in experimental autoimmune encephalomyelitis: Therapeutic implications for Multiple Sclerosis," J Neurosci Res, 78(5):603-24 (2004).
Ortho-Micronor. Drug Datasheet (online). Ortho-McNeil Pharmaceuticals. Http://www.orthomcneilpharmaceutical.com/products/pi/pdfs/micro.pdf, p. 1 (1998).
Paty et al., "Interferon beta-1 b is effective in relapsing-remitting Multiple Sclerosis. II. MRI analysis results of a multicenter, randomized, double-blind, placebo-controlled trial," Neurology, 43:662-7 (1993).
Perrella et al., "Protection of cortical cells by equine estrogens against glutamate-induced excitotoxicity is mediated through a calcium independent mechanism," BMC Neurosci, 6:34 (2005).

(56) References Cited

OTHER PUBLICATIONS

Polman et al., "The treatment of Multiple Sclerosis: Current and future," Curr Opin Neurol, 8(3):200-9 (1995).
Powell et al., "Lymphotoxin and tumor necrosis factor-alpha production by myelin basic protein specific T cell clones correlates with encephalitogenicity," Int Immunol, 2:539-44 (1990).
Pratt et al., "Estriol production rates and breast cancer," J Clin Endocrinol Metabolism, 46:44-7 (1978).
Prempro and Premphase drug information, Food and Drug Administration, dated Jun. 5, 2003, Retrieved from the Internet. URL: http://www.fda.gov/ohrms/dockets/ac/03/briefing/3992B1_03_FDA-Prempro-Premphase.pdf.
Quesada et al., "Estrogen interacts with the IGF-1 system to protect nigrostriatal dopamine and maintain motoric behavior after 6-hydroxdopamine lesions," J Neurosci Res, 75:107-16 (2004).
Ramirez et al., "Repeated estradiol treatment prevents MPTP-induced dopamine depletion in male mice," Neuroendocrinol, 77:223-31 (2003).
Ratkay et al., "Evaluation of a model for post-partum arthritis and the role of oestrogen in prevention of MRL-Ipr associated rheumatic conditions," Clin Exp Immunol, 98(1):52-9 (1994).
Recchia et al., "Interferon-B, retinoids, and tamoxifen in the treatment of metastatic breast cancer: A phase II study," J Interferon Cytokine Res, 15:605-10 (1995).
Rep et al., "Treatment with depleting CD4 monoclonal antibody results in a preferential loss of circulating naïve T cells but does not affect IFN-gamma secreting TH I cells in humans," J Clin Investig, 99(9):2225-31 (1997).
Rice et al., "Postmenopausal estrogen and estrogen-progestin use and 2-year rate of cognitive change in a cohort of older Japanese American women: The Kame Project," Arch Internal Med, 160:1641-9 (2000).
Rossouw et al., "Risks and benefits of estrogen plus progestin in healthy postmenopausal women: Principal results from the Women's Health Initiated randomized controlled trial," JAMA, 288:321-33 (2002).
Rott et al., "Interleukin-IO prevents experimental allergic encephalomyelitis in rats," Eur J Immunol, 24:1434-40 (1994).
Rudick et al., "In vivo effects of interferon beta-I a on immunosuppressive cytokines in Multiple Sclerosis," Neurology, 50:1294-300 (1998).
Rudick et al., "Use of the brain parenchymal fraction to measure whole brain atrophy in relapsing-remitting MS. Multiple Sclerosis Collaborative Research Group," Neurology, 53:1698-1704 (1999).
Runmarker et al., "Pregnancy is associated with a lower risk of onset and a better prognosis in Multiple Sclerosis," Brain, 118:253-6 (1995).
Ryan et al., "Changes in serum hormone levels associated with male-induced ovulation in group-housed adult female mice," Endocrinol, 106:959 (1980).
Sadovnick, "Update on management and genetics of Multiple Sclerosis," J Neural Transm, 50(Suppl.):167-72 (1997).
Sanchez-Guerrero et al., "Postmenopausal estrogen therapy and the risk for developing systemic lupus erythematosus," Ann Internal Med, 122:430-3 (1995).
Sandor et al., "Surface-based labeling of cortical anatomy using a deformable atlas," IEEE Transactions on Medical Imaging, 16:41-54 (1997).
Sandyk, "Estrogen's impact on cognitive functions in Multiple Sclerosis," Int J Neurosci, 86:23-31 (1996).
Saunders-Pullman, "Estrogens and Parkinson disease: neuroprotective, symptomatic neither, or both?" Endocrine, 21:81-7 (2003).
Sawada et al., "Estrogens and Parkinson disease: Novel approach for neuroprotection," Endocrine, 21:77-9 (2003).
Schiff et al., "Effect of estriol administration on the hypogonadal woman," Fertility Sterility, 30:278-82 (1978).
Schmidberger et al., "The combined effect of interferon beta radiation on five human tumor cell lines and embryonal lung fibroblasts," Int J Radiat Oncol Biol Phys, 43:405-12 [abstract only] (1999).
Schmidt et al., "New treatment of atrophic 20 acne scars by Iontophoresis with estriol and tretinoin," Int J Dermatol, 34(1):53-7 (1995).
Schmidt et al., "Treatment of skin aging with topical estrogens," Int J Dermatol, 35(9):669-74 (1996).
Schountz et al., "MHC genotype controls the capacity of ligand density to switch T helper (Th)-Irrh-2 priming in vivo," J Immunol, 157:3893-901 (1996).
Search Report for European Patent Application No. 02729034 dated Dec. 22, 2004.
Search Report for European Patent Application No. 06815340 dated Nov. 10, 2010.
Search Report for European Patent Application No. 06815626 dated Nov. 18, 2010.
Search Report for European Patent Application No. 08754819 dated Aug. 10, 2010.
Shughrue, "Estrogen attenuates the MPTP-induced loss of dopamine neurons from the mouse SNc despite a lack of estrogen receptors (Eralpha and Erbeta)," Exp Neurol, 190:468-77 (2004).
Sicotte et al., "Treatment of Multiple Sclerosis with the pregnancy hormone estriol," Ann Neurol, 52:421-8 (2002).
Sicotte et al., "Treatment of women with Multiple Sclerosis using the pregnancy hormone estriol: A pilot study," Neurology, 56(Suppl. 3) (2001).
Smith et al., "A pilot study of the effect upon Multiple Sclerosis of the menopause, hormone replacement therapy and the menstrual cycle," J Royal Soc Med, 85:612-3 (1992).
Smith et al., "Impact of combined estradiol and norethindrone therapy on visuospatial working memory assessed by functional magnetic resonance imaging," J Clin Endocrinol Metab, 91(11):4476-81 (2006).
Smith et al., "Quantitative estimation of estrogen conjugates in late 20 pregnancy plasma," J Clin Endocrinol Metabolism, 25:732-41 (1965).
Soldan et al., "Immune modulation in Multiple Sclerosis patients treated with the pregnancy hormone estriol," J Immunol, 171(11):6267-74 (2003).
Speroff et al., "Postmenopausal hormone therapy," Gynecololgy and Obstetrics, Chapter 110, Mar. 8, 2011. URL: http://www.glowm.com/resources/glowm/cd/pages/v1/v1c110.html.
Stinissen et al., "Autoimmune pathogenesis of Multiple Sclerosis: Role of autoreactive T lymphocytes and new immunotherapeutic strategies," Crit Rev Immunol, 17(1):33-75 (1997).
Strauss et al., "Placental hormones," Endocrinol, 3(9):2171-223 (1994).
Stuart et al., "Concomitant therapy for Multiple Sclerosis," Neurology, 63(Suppl.5):S28-S34 (2004).
Suenaga et al., "Peripheral blood T cells and monocytes and B cell lines derived from patients with lupus express estrogen receptor transcripts similar to those of normal cells," J Rheumatol, 25:1305-12 (1998).
Sylvia et al., "17 beta-estradiol-BSA conjugates and 17 beta-estradiol regulate growth plate chondrocytes by common membrane associated mechanisms involving PKC dependent and independent signal transduction," J Cell Biochem, 81:413-29 (2001).
Thompson, "Multiple Sclerosis: Symptomatic treatment," J Neurology, 243(8):559-65 (1996).
Thorogood et al., "The influence of oral contraceptives on the risk of Multiple Sclerosis," Brit J Obstetrics Gynecol, 105:1296-9 (1998).
Tiwari-Woodruff et al., "Differential neuroprotective and anti-inflammatory effects of estrogen receptor (ER)alpha and (ER)beta ligand treatment," PNAS, 104(37):14813-8 (2007).
Trapp et al., "Axonal pathology in Multiple Sclerosis: Relationship to neurologic disability," Curr Opin Neurol, 12:295-302 (1999).
Trapp et al., "Pathogenesis of tissue injury in MS lesions," J Neuroimmunol, 98:49-56 (1999).
Troisi et al., "Maternal serum oestrogen and androgen concentrations in preeclamptic and uncomplicated pregnancies," Int J Epidemiol, 32(3):458 (2003).
Trooster et al., "Treatment of acute experimental allergic encephalomyelitis in the Lewis rat with the sex hormone progesterone," Int J Immunopathol, 7(3):183-92 (1994).

(56) References Cited

OTHER PUBLICATIONS

Tsang et al., "The use of estrogen in the treatment of Parkinson's disease," Parkinsonism and Related Disorders, 8:133-7 (2001).
Tzingounis et al., "Estriol in the management of menopause," JAMA, 239:1638-41 (1978).
Utian, "The place of oestriol therapy after menopause," Acta Endocrinologica, 95(Suppl.233):51-6 (1980).
Vakil et al., "Benign breast disease: Estriol proportions and family history of breast cancer," Cancer Detection and Prevention, 4:517-23 (1981).
Van Boxel-Dezaire et al., "Decreased interleukin-10 and increased interleukin-12p40 mRNA are associated with disease activity and characterize different disease stages in Multiple Sclerosis," Ann Neurology, 45:695-703 (1999).
Van Vollenhoven et al., "Estrogen, progesterone, and testosterone: Can they be used to treat autoimmune diseases?" Cleveland Clinic J Med, 61:276-84 (1994).
Vandenbark et al., "TCR peptide therapy in human autoimmune diseases," Neurochem Res, 26:713-30 (2001).
Vandenbark et al., "Treatment of Multiple Sclerosis with T-cell receptor peptides: Results of a double-blind pilot trial," Nat Med, 2(10):1109-15 (1996).
Vanderhorst et al., "Estrogen induces axonal outgrowth in the nucleus retroambiguus-lumbosacral motoneuronal pathway in the adult female cat," J Neurosci, 17:1122-36 (1997).
Verghese et al., "Cognitive performance in surgically menopausal women on estrogen," Neurology, 55:872-4 (2000).
Villard-Mackintosh et al., "Oral contraceptives and reproductive factors in Multiple Sclerosis incidence," Contraception, 47:161-8 (1993).
Volpe et al., "Benefits and risks of different hormonal replacement therapies in post-menopausal women," Maturitas, 8:327-34 (1986).
Voskuhl et al., "A functional basis for the association of HLA class II genes and susceptibility to Multiple Sclerosis: Cellular immune responses to myelin basic protein in a multiplex family," J Neuroimmunol, 42:199-207 (1993).
Voskuhl et al., "Female sex hormone at supraphysicologic, but not physiologic, levels decrease EAE severity in female SJL mice," FASEB J IS, A372 (2001).
Voskuhl et al., "Hormone-based therapies in MS," Int MS J, 10(2):61-6 (2003).
Voskuhl et al., "Sex hormones in experimental autoimmune encephalomyelitis: Implications for Multiple Sclerosis," The Neuroscientist, 7:258-70 (2001).
Watkins-Smith, et al., "Quantitative Estimation of Estrogen Conjugates in Late 20 Pregnancy Plasma," J Clin Endocrinol, 25: 732-741 (1965).
Website downloaded Feb. 2, 2011 from webmd.com/multiple-sclerosis/tc/multiple-sclerosis-ms-prevention; 2 pages total.
Wegmann et al., "Bidirectional cytokine interactions in the maternal-fetal relationship: Is successful pregnancy a Th2 phenomenon?" Immunology Today, 14:353-6 (1993).
Wen et al., "Transient cerebral ischemia induces aberrant neuronal cell cycle re-entry and Alzheimer's disease-like tauopathy in female rats," J Biol Chem, 279(21):22684-92 (2004).
Wilder, "Hormones, pregnancy, and autoimmune diseases," Ann NY Acad Sci, 840(1):45-50 (1998).
Wilson et al., "Results of a phase I clinical trial of a T-cell receptor peptide vaccine in patients with Multiple Sclerosis. J. Analysis of T-Cell receptor utilization in CSF cell populations." J Neuroimmunol, 76(1-2):15-28 (1997).
Wise, "Estrogens and neuroprotection," Trends Endocrinol Metabolsim, 13(6):229-30 (2002).
Wozniak et al., "Xenoestrogens at picomolar to nanomolar concentrations trigger membrane estrogen receptor-a-mediated Ca2+ fluxes and prolactin release in GH3/B6 pituitary tumor cells," Environ Health Perspectives, 113(4):431-9 (2005).
Xu et al., "Study of relapsing remitting experimental allergic encephalomyelitis SJL mouse model using MION-46L enhanced in vivo MRI: Early histopathological correlation," J Neurosci Res, 52:549-58 (1998).
Zhang, et al., Clin Exp Immunol, 98: 52-59 (1994).
Zhu et al., "Quantitative structure-activity relationship of various endogenous estrogen metabolites for human estrogen receptor a and b subtypes: Insights into the structural determinants favoring a differential subtype binding," Endocrinol, 147:4132-50 (2006).
Ziehn et al., Laboratory Investigation, 92:1234-45 (2012).
Zorgdrager et al., "Menstrually related worsening of symptoms in Multiple Sclerosis," J Neurological Sci, 149:95-7 (1997).
MacFarland et al., "AC-186 a Selective Nonsteroidal Estrogen Receptor β Agonist, Shows Gender Specific Neuroprotection in a Parkinson's Disease Rat Model," ACS Chemical Neuroscience, 4:1249-1255 (2013).
Wisdom et al., "Estrogen Receptor-Beta Ligand Treatment After Disease Onset is Neuroprotective in the Multiple Sclerosis Model," J Neurosci Res, 91(7):901-908 (2013).
Choi et al., "FTY720 (fingolimod) efficacy in an animal model of multiple sclerosis requires astrocyte sphingosine 1-phosphate receptor 1 (S1P1) modulation," PNAS, 108(2):751-756 (2011).
Gold et al., "Understanding pathogenesis and therapy of multiple sclerosis via animal models: 70 years of merits and culprits in experimental autoimmune ecephalomyelitis research," Brain, 129:1953-1971 (2006).
Karim et al., "Increase in chemokine CXCL1 by Erβ ligand treatment is a key mediator in promoting axon myelination," PNAS, 115(24):6291-6296 (2018).
Ranshohoff, "Animal models of multiple sclerosis: the good, the bad and the bottom line," Nature Neuroscience, 15(8):1074-1077 (2012).

\* cited by examiner

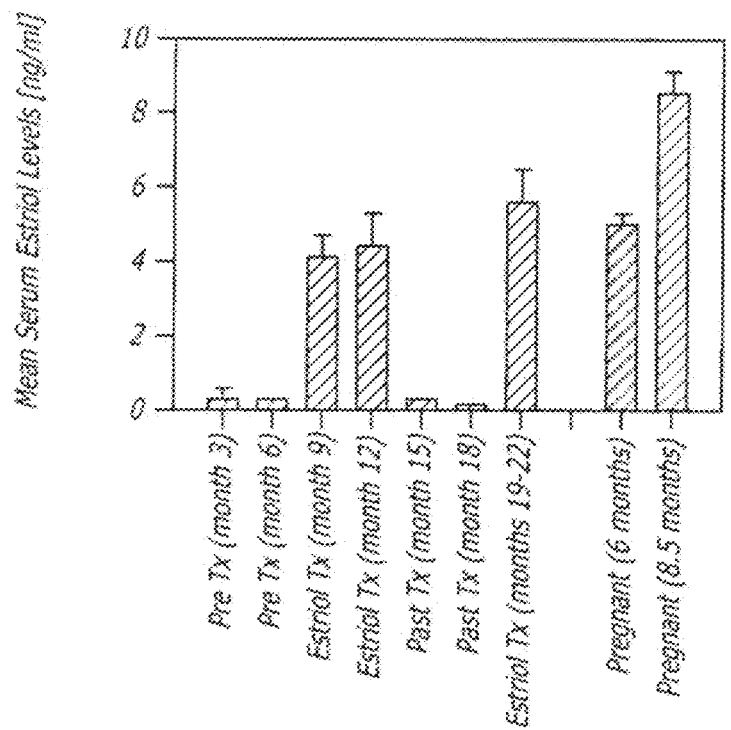

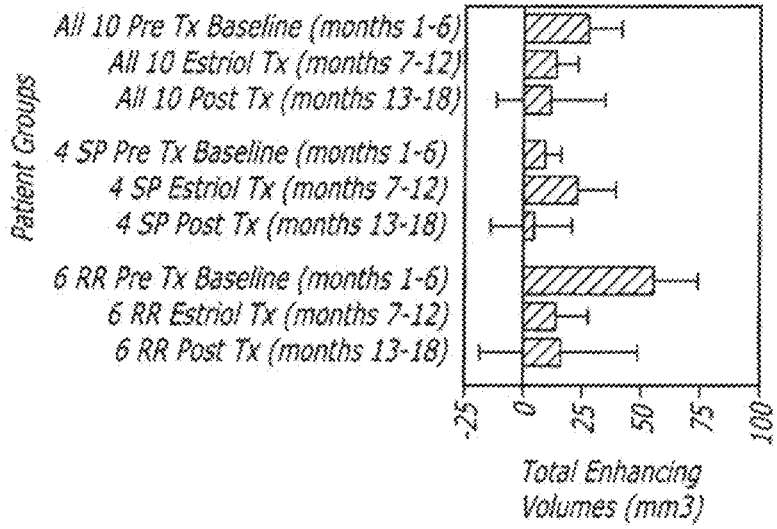
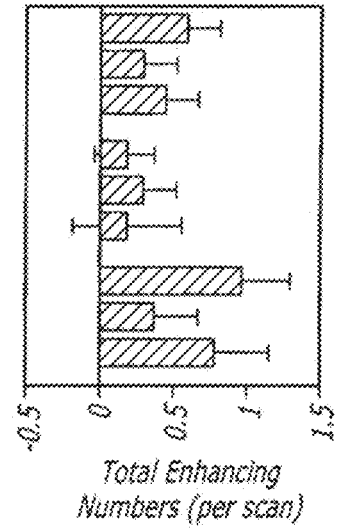
FIG. 3A
FIG. 3B
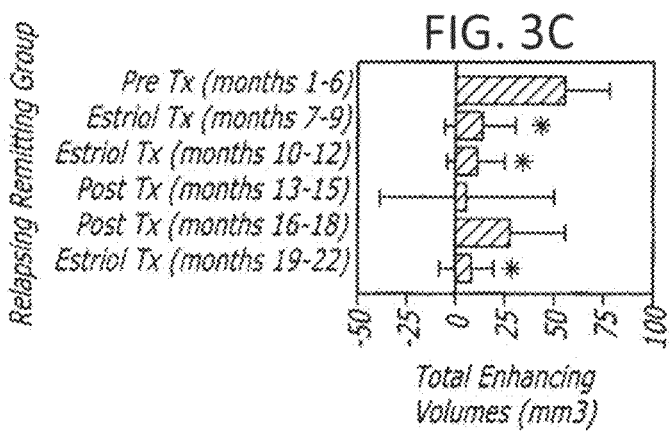
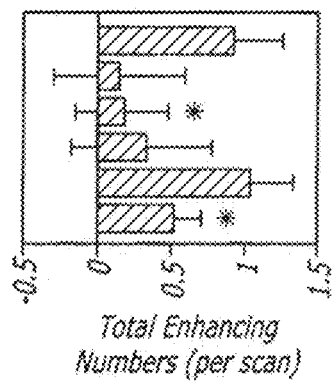
FIG. 3C
FIG. 3D
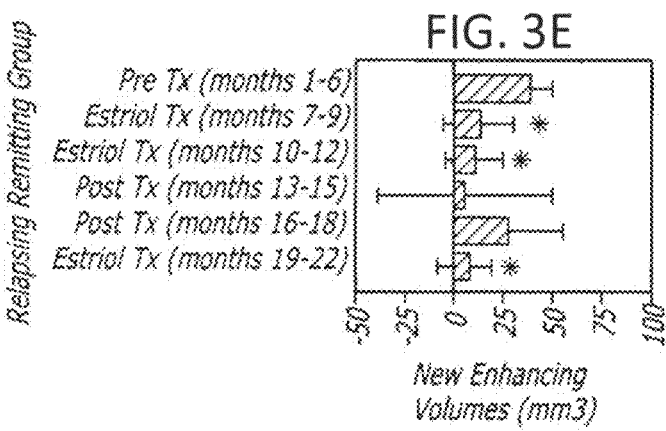
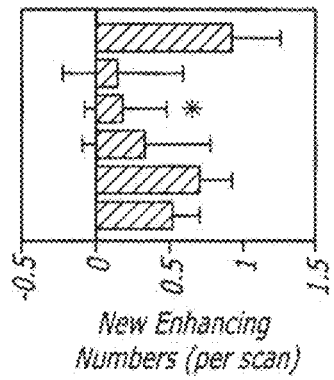
FIG. 3E
FIG. 3F

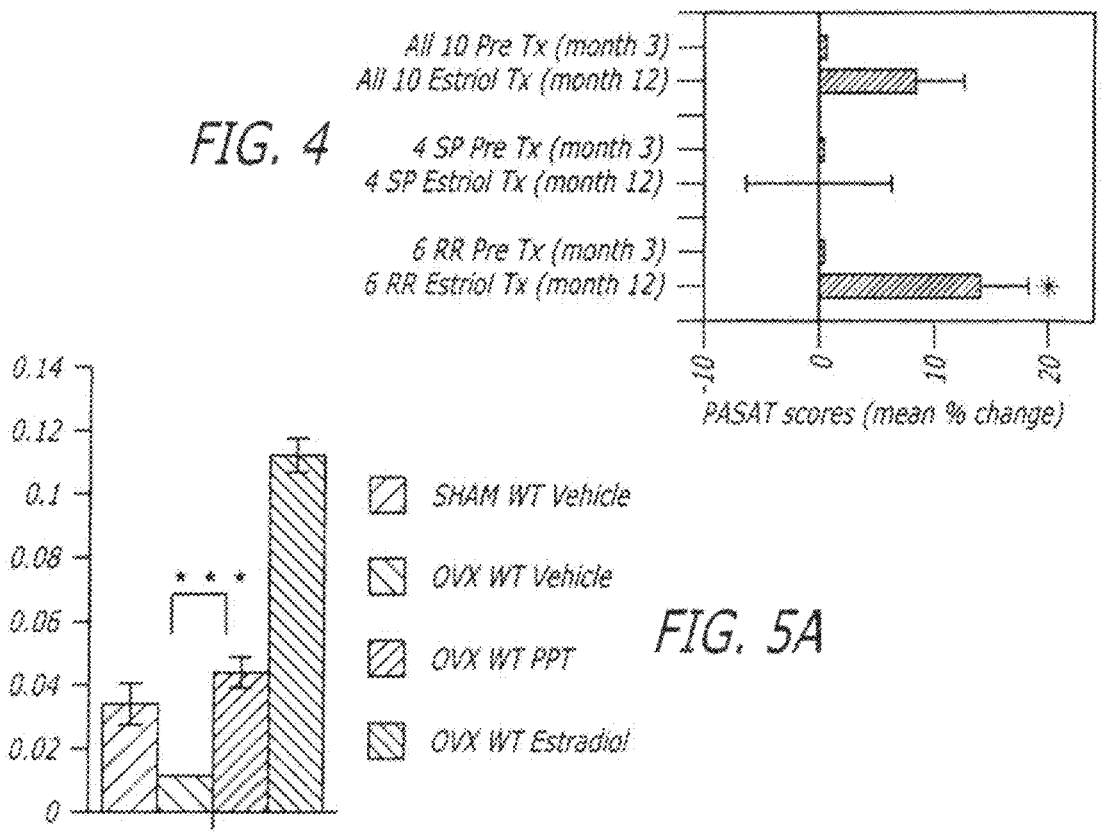
FIG. 4
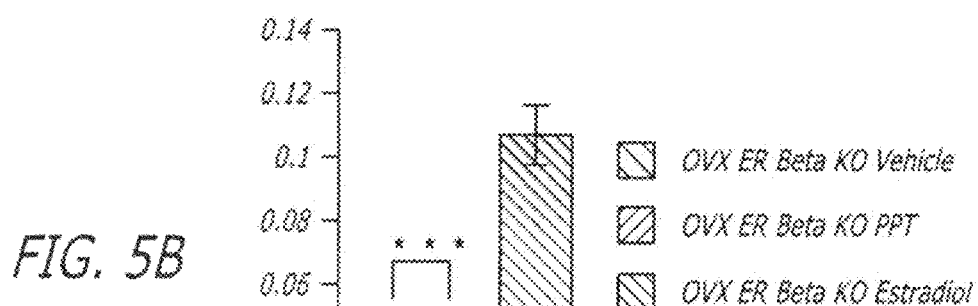
FIG. 5A
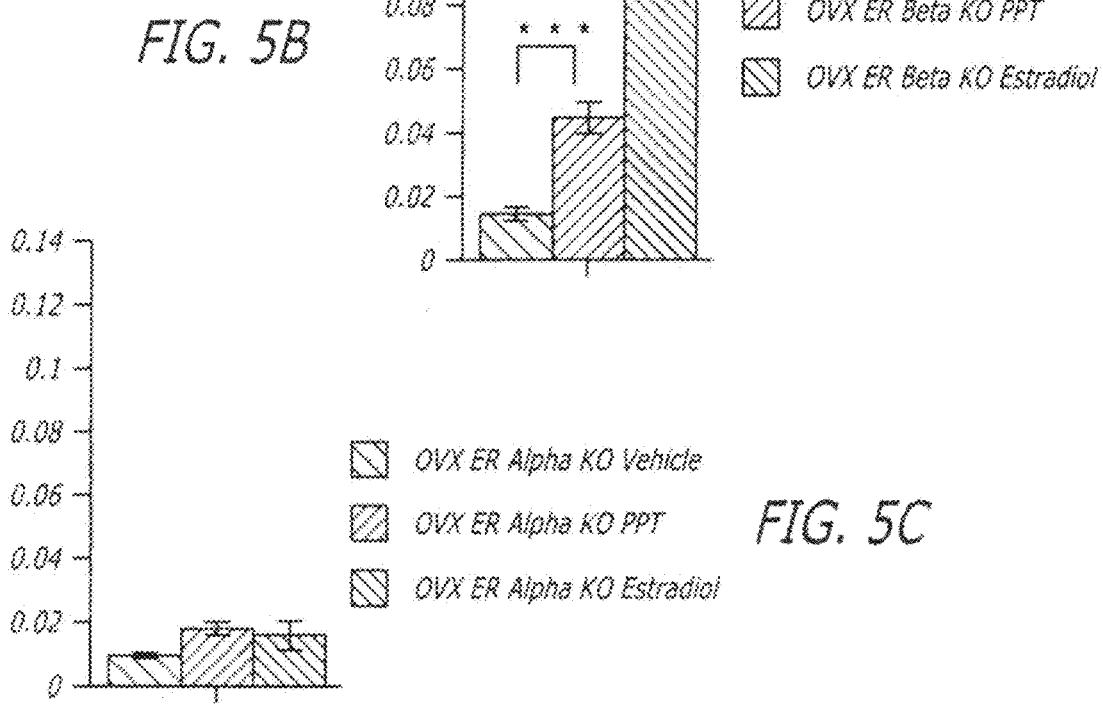
FIG. 5B
FIG. 5C

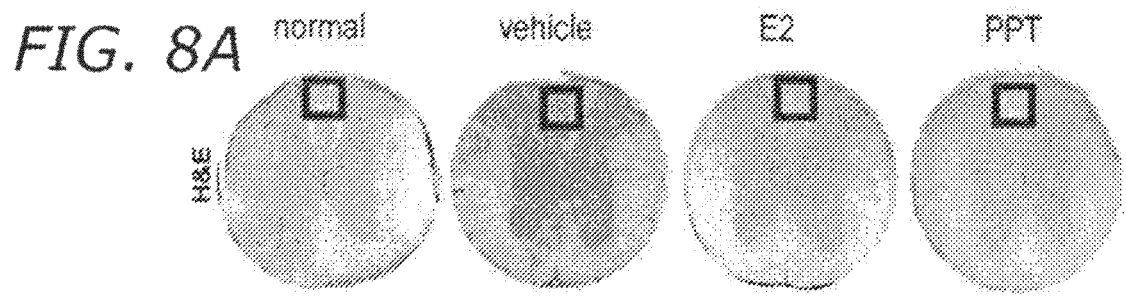
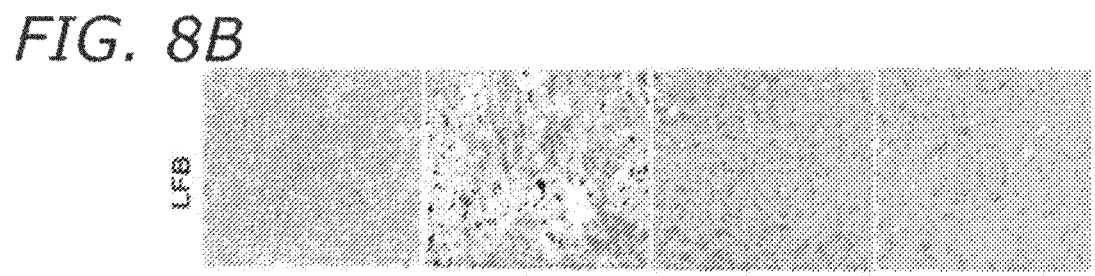
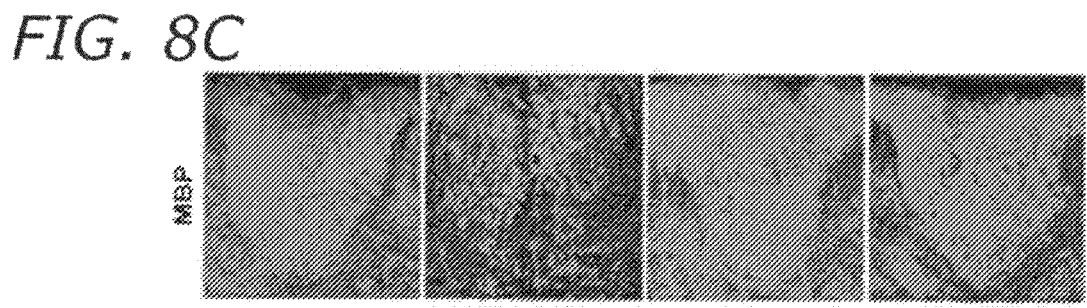
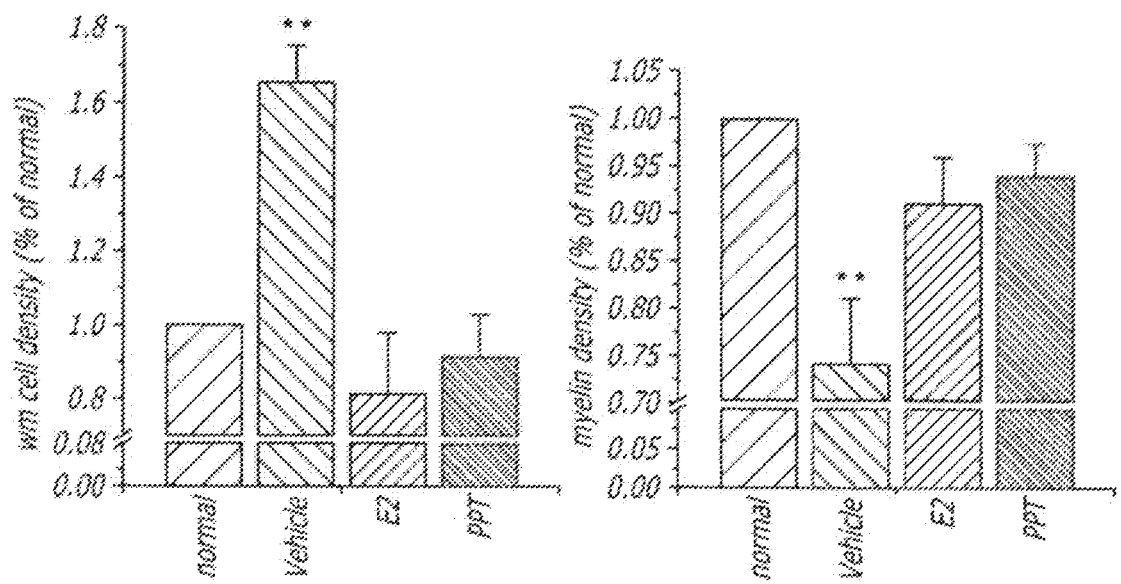
FIG. 8D    FIG. 8E

FIG. 10A
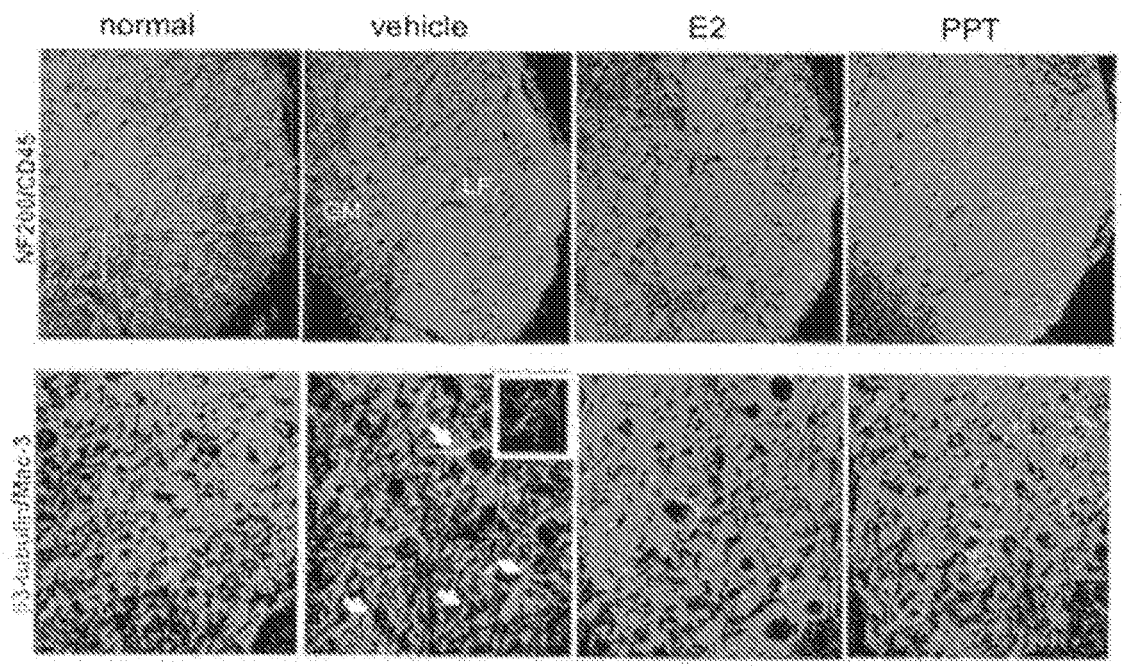
FIG. 10B
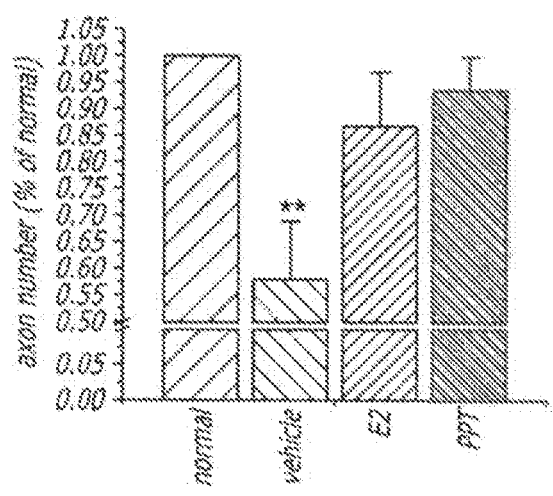
FIG. 10C
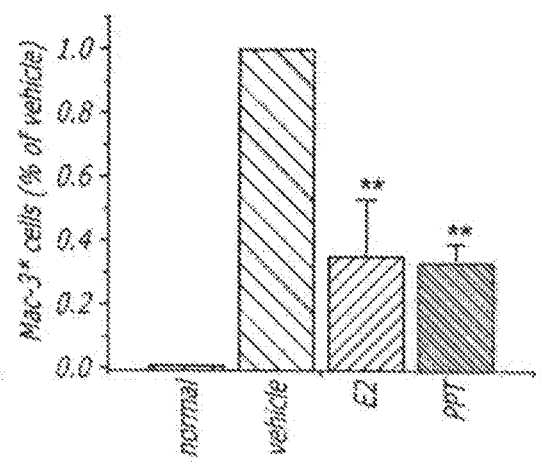
FIG. 10D

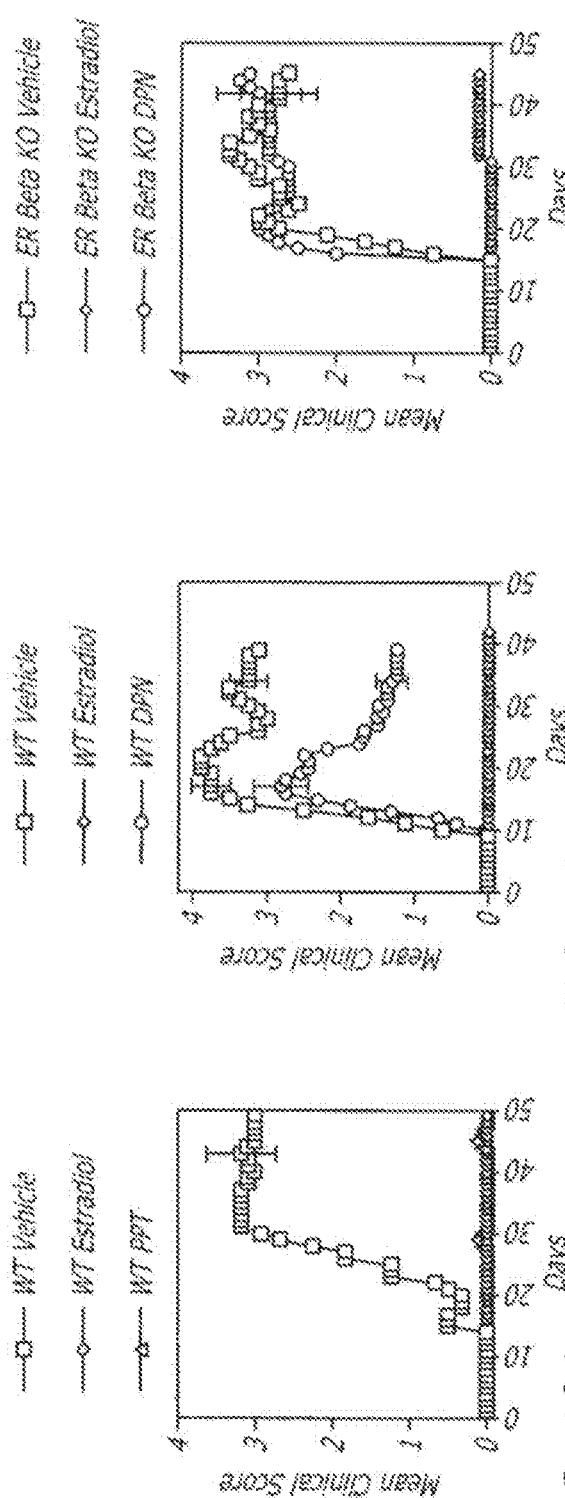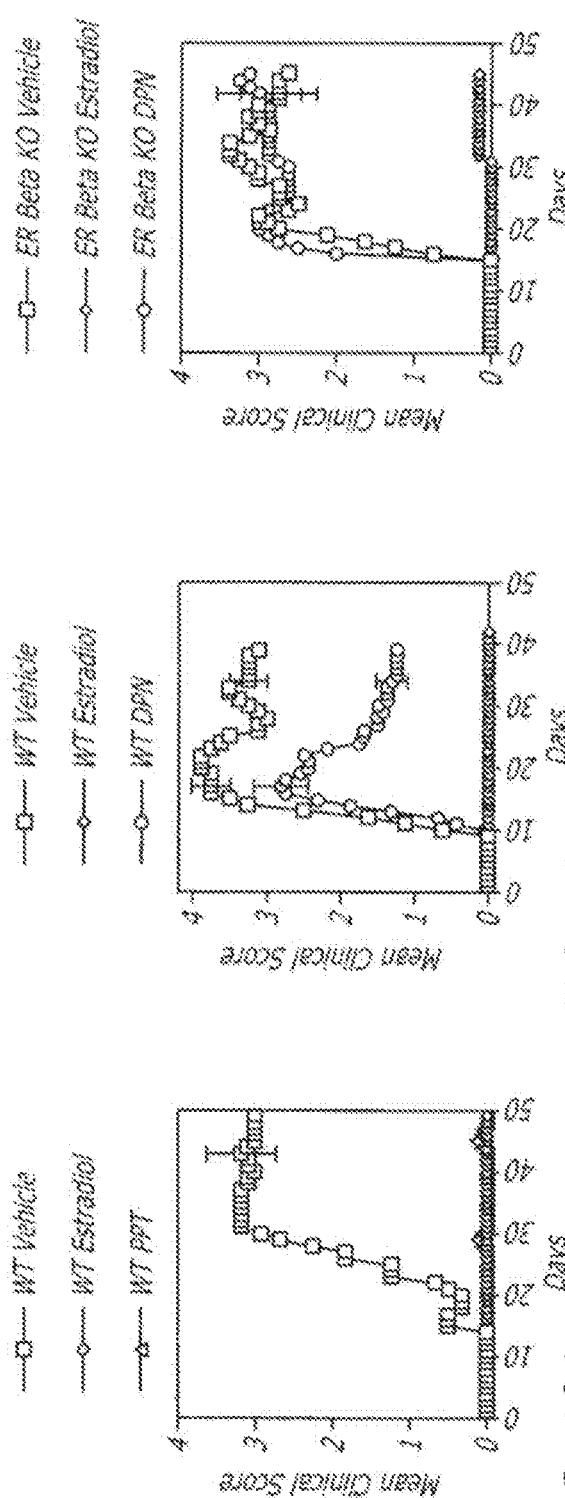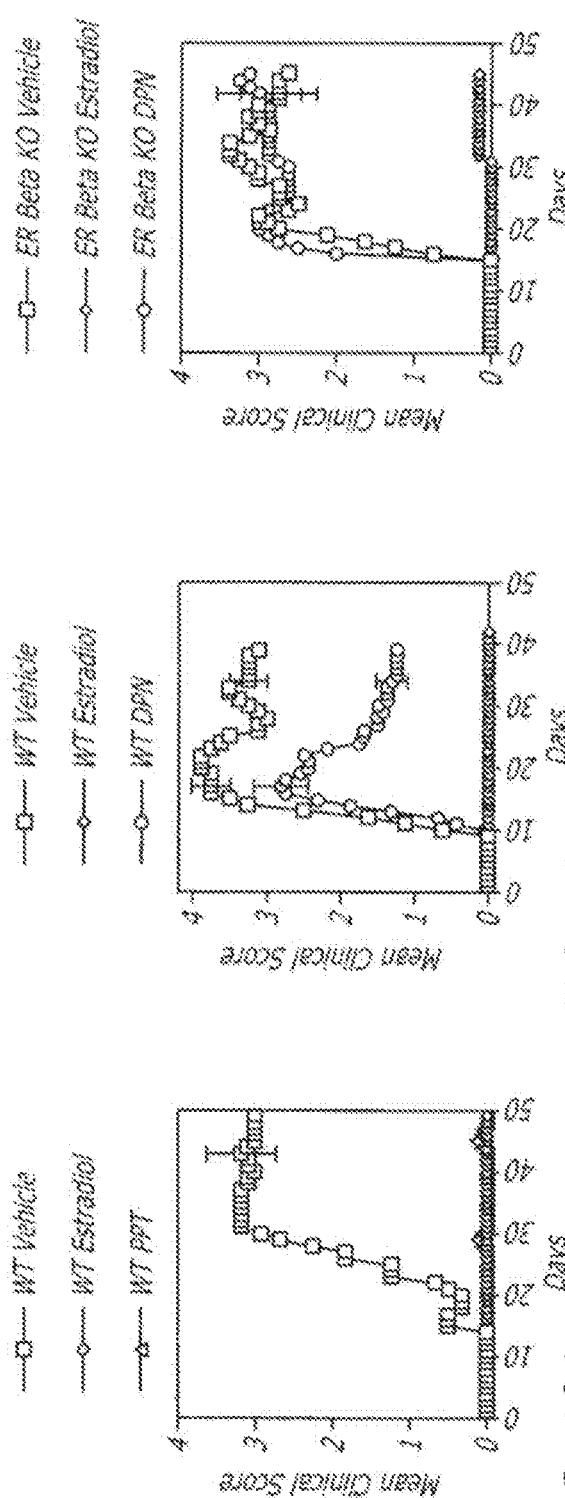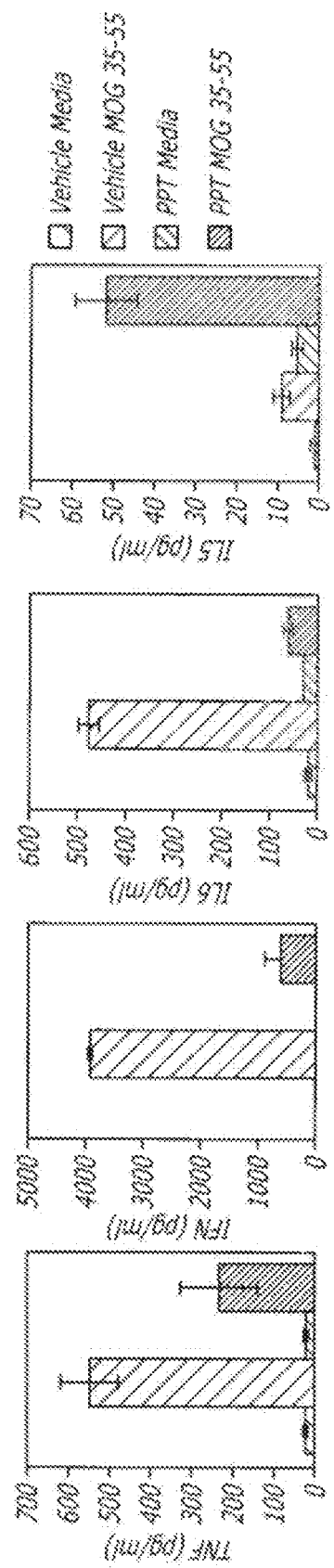
FIG. 12A
FIG. 12B
FIG. 12C
FIG. 12D

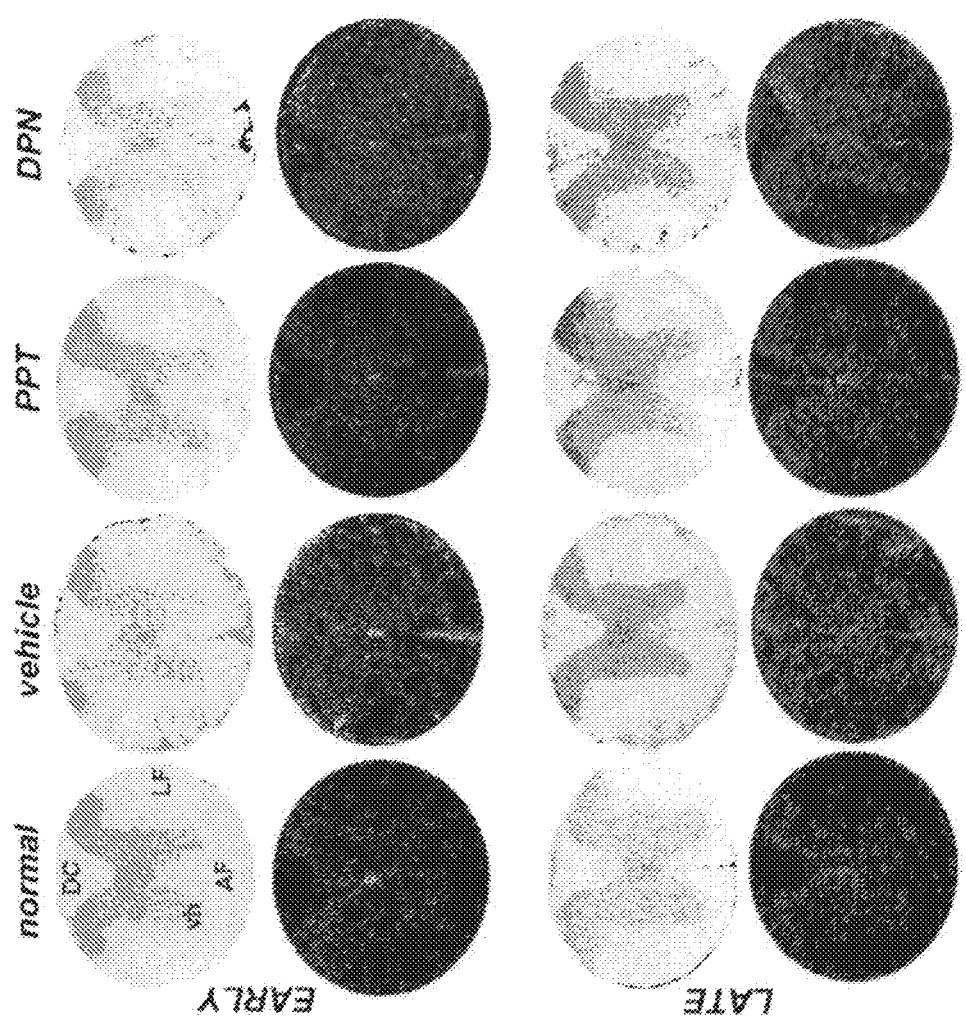
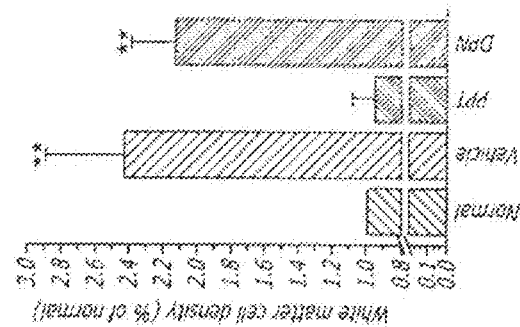
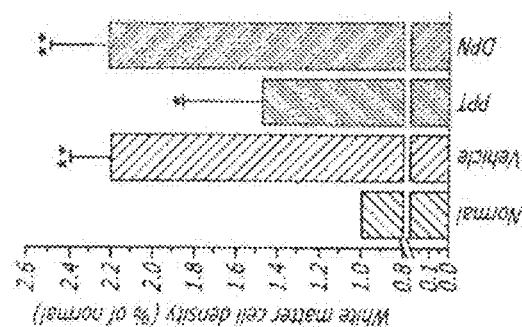

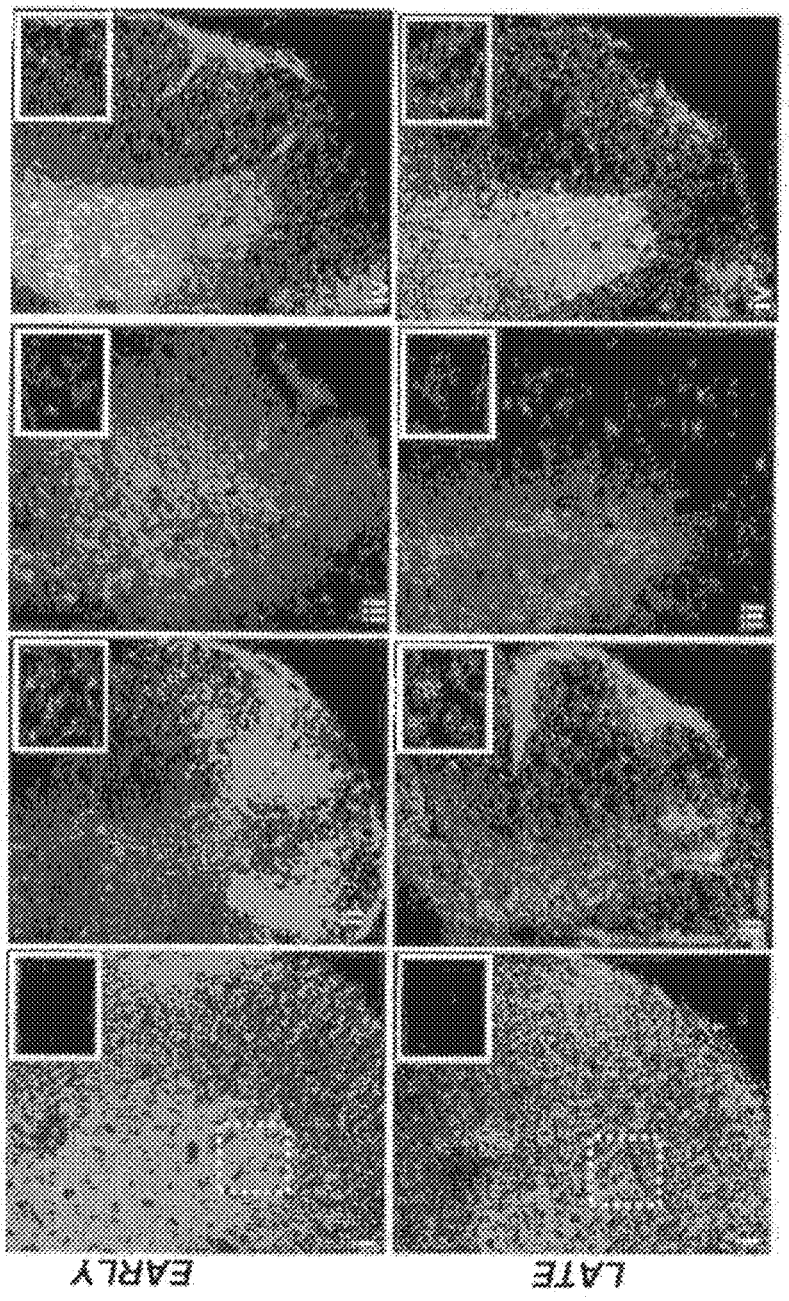

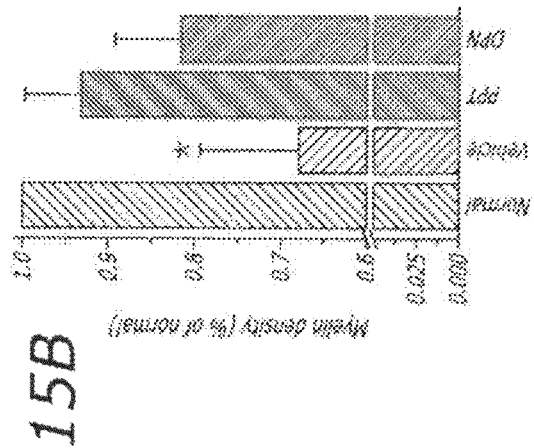
FIG. 15B
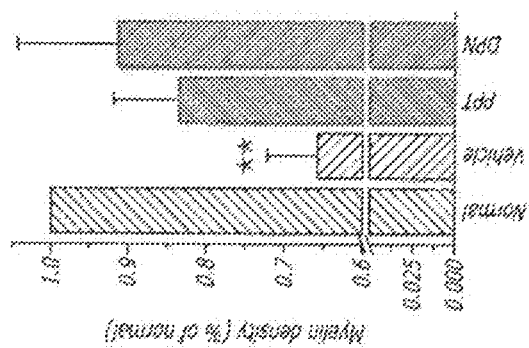
FIG. 15D
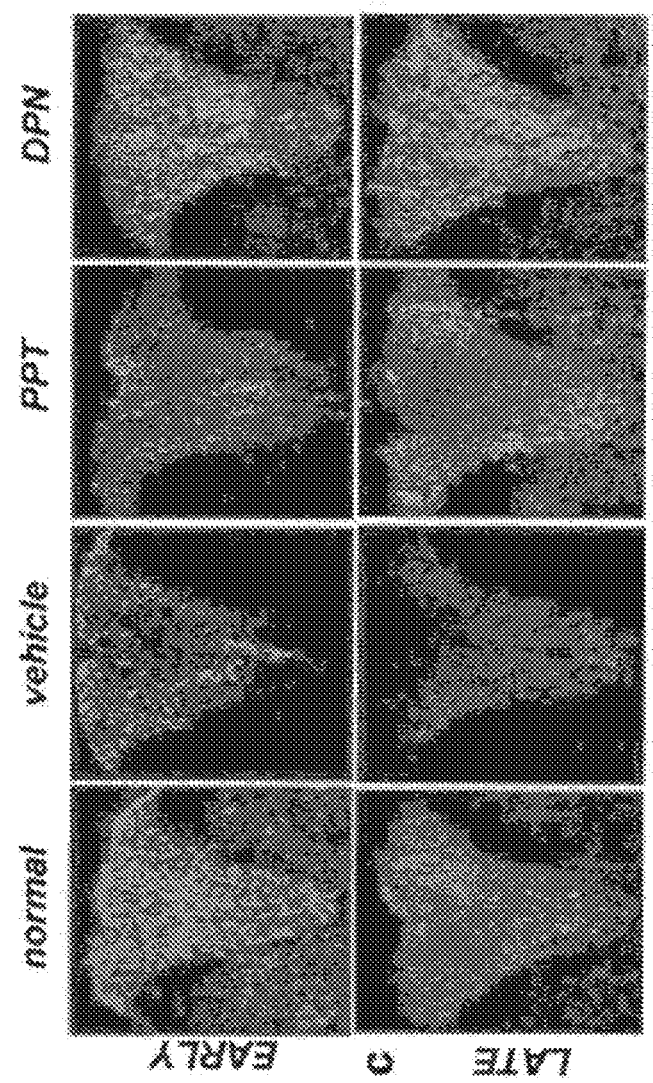
FIG. 15A
FIG. 15C

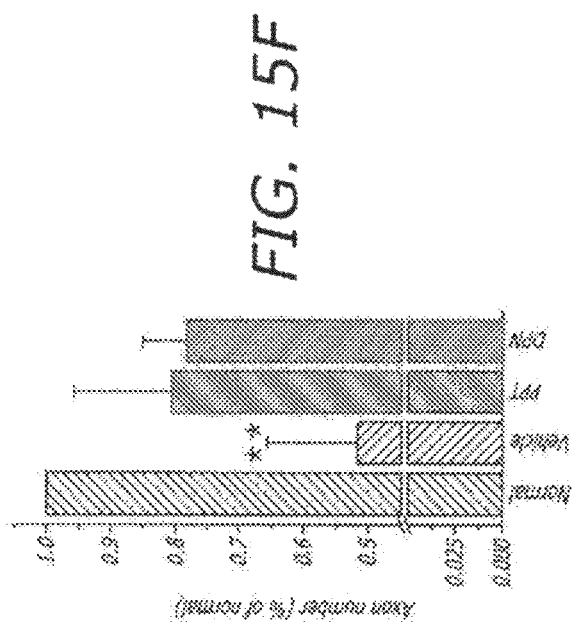
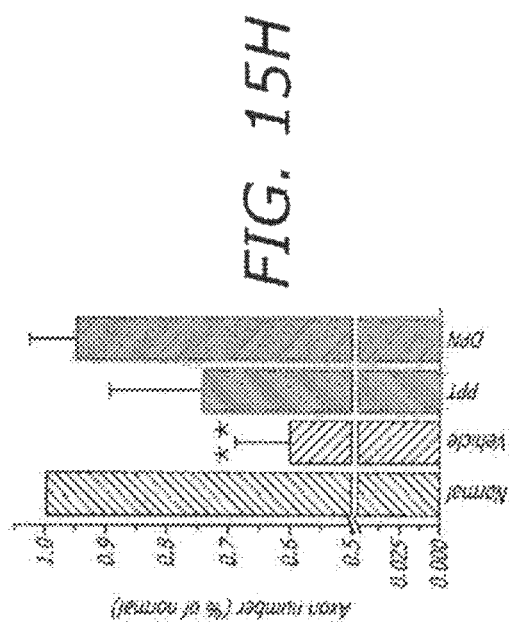
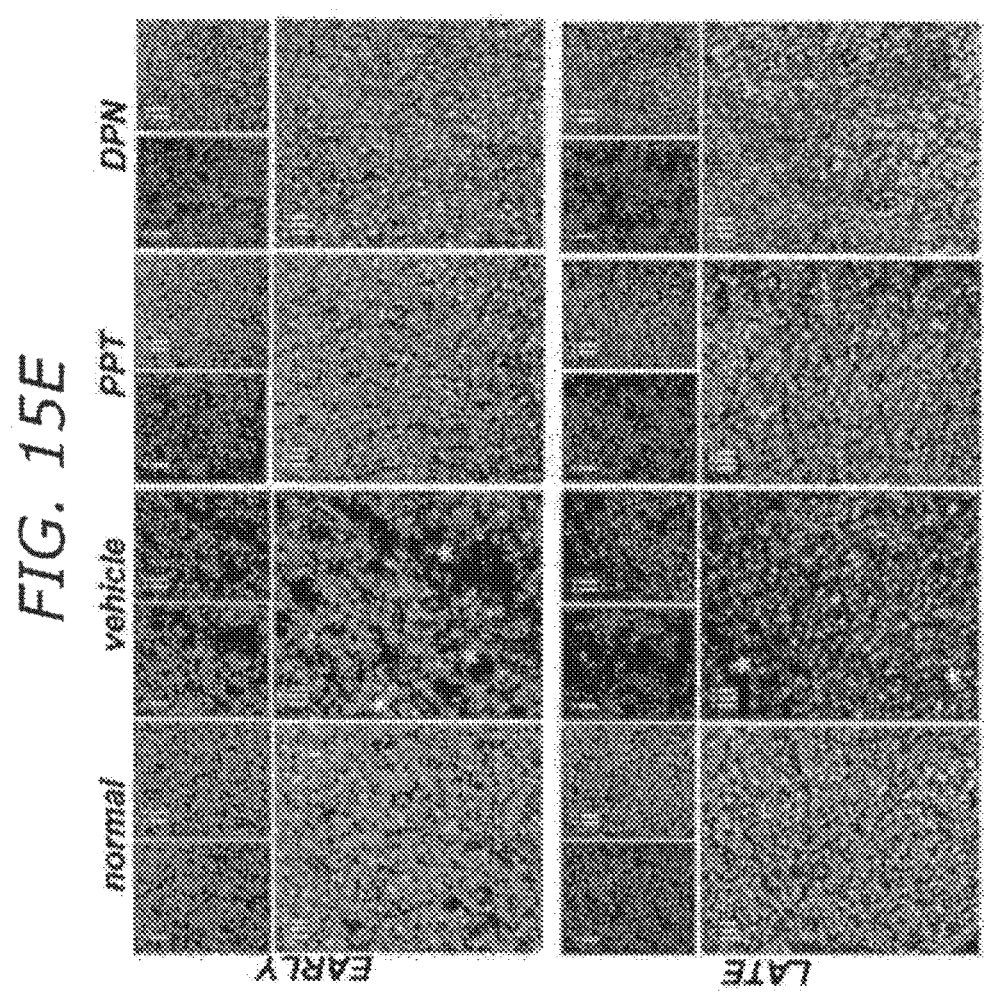

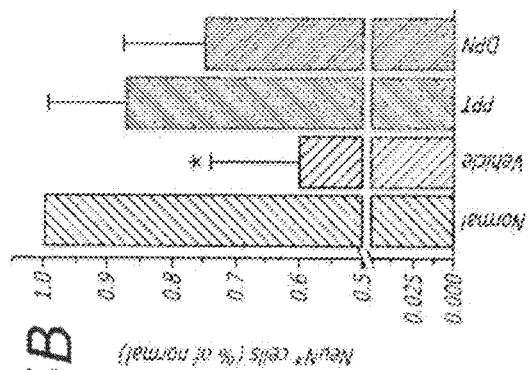
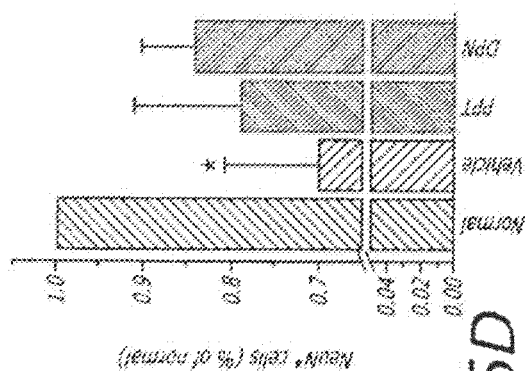
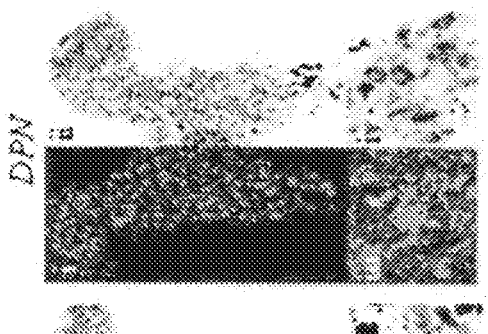
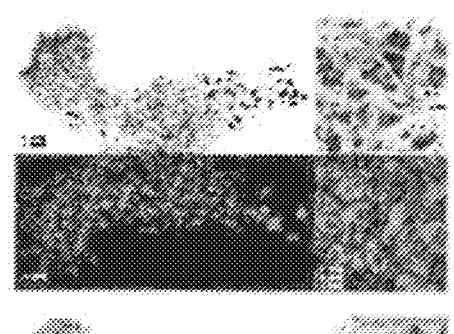
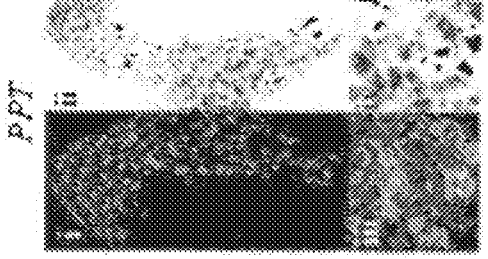
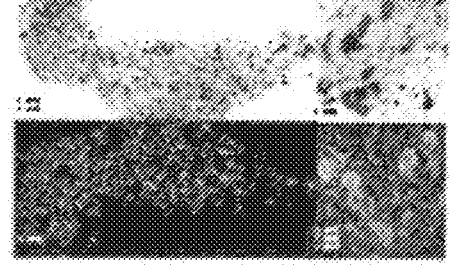
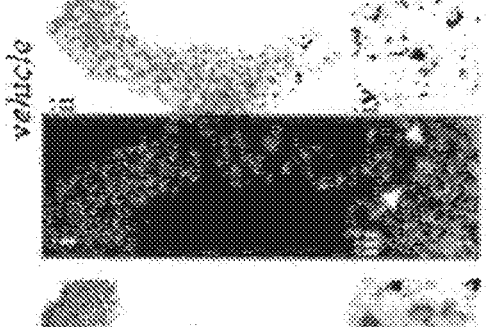
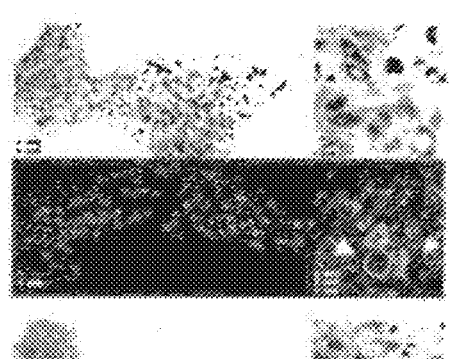
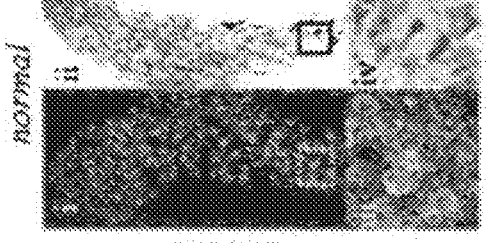
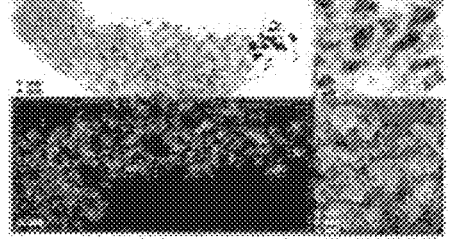
FIG. 16A  FIG. 16B  FIG. 16C  FIG. 16D

DIARYLPROPIONITRILE THERAPY FOR TREATMENT OF MULTIPLE SCLEROSIS

CROSS-REFERENCE TO RELATED APPLICATIONS

This application is a continuation of U.S. patent application Ser. No. 14/333,027, filed Jul. 16, 2014, which is a continuation of U.S. patent application Ser. No. 13/722,672, filed Dec. 20, 2012, which is a continuation of U.S. patent application Ser. No. 11/992,558, filed Mar. 25, 2008, which claims priority from International Patent Application No. PCT/US2006/037259, filed Sep. 26, 2006, which claims priority to U.S. Provisional Application No. 60/833,527, filed Jul. 26, 2006, and U.S. Provisional Application No. 60/720,971, filed Sep. 26, 2005, all of which are incorporated by reference herein.

This invention was made with Government support under Grant No. NS045443 awarded by the National Institute of Neurological Disorders and Stroke, National Institutes of Health. The government has certain rights in this invention.

BACKGROUND OF THE INVENTION

1. Field of the Invention

This invention relates generally to steroidal therapies for treating autoimmune diseases, and, more particularly, to administering primary agents being estrogens or estrogen receptor active agents for the treatment of cell mediated diseases. Optionally, secondary agents which effect the immune and/or nervous system may also be co-administered or tapered onto. This therapy may be used in patients, including post-partum patients. This invention also relates to steroidal therapies for the treatment of neurodegenerative diseases and disorders, including cell mediated diseases. Finally, treatment kits are provided containing at least one primary agent and at least one secondary agent for treating a patient presenting with symptomology of an autoimmune disease or a neurodegenerative disease or disorder.

2. General Background and State of the Art

There is a distinct female preponderance of autoimmune diseases during the reproductive ages including multiple sclerosis (MS), rheumatoid arthritis (RA), uveitis, myasthenia gravis (MG), Sjogren's syndrome, and Hashimoto's thyroiditis.

For example, MS is a chronic, and often debilitating disease affecting the central nervous system (brain and spinal cord). MS affects more than 1 million people worldwide and is the most common neurological disease among young adults, particularly woman. The exact cause of MS is still unknown. MS attacks the nervous system resulting in myelin sheaths surrounding neuronal axons to be destroyed. This demyelinization can cause weakness, impaired vision, loss of balance, and poor muscle coordination. MS can have different patterns, sometimes leaving patients relatively well after episodes of acute worsening, sometimes leading to progressive disability that persists after episodes of worsening. In the worst cases the disease can lead to paralysis or blindness.

Steroid hormones or sex-linked gene inheritance may be responsible for the enhanced susceptibility of women to these autoimmune diseases. A role for steroid hormones in susceptibility to autoimmune disease is supported by observations of alternations in disease symptomatology, with alterations in sex hormone levels such as during pregnancy, menopause or exogenous hormone administration (in the form of hormone replacement (HRT) or oral contraceptives (ORC)). For example, women with MS and RA have been reported to experience remission of symptoms during late gestation. Particularly, MS patients have been reported to show a decrease in relapse rate in pregnancy.

Normally, cell-mediated immunity is mediated by T helper cell (Th1) secretion of interferon gamma (IFN-.gamma.) and tumor necrosis factor beta (TNF-b). In contrast, humoral immunity is mediated by another group of T helper cells (Th2) secreting interleukin (IL)-10, IL-4, IL-5 and IL-6. A systemic shift toward humoral immunity (or Th2-mediated immunity) has been noted during pregnancy. During pregnancy, cell-mediated immunity is decreased and humoral-mediated immunity is increased thereby promoting fetal survival. Thus, this systemic shift in the immune system may explain why cell-mediated diseases, including MS and RA have been reported to improve during pregnancy.

Although a shift toward humoral-mediated immunity has been demonstrated during human pregnancy, mechanisms which induce this shift remain unclear. One possibility is local production of Th2 (or humoral mediated) cytokines by the placenta. Another possibility is the production of Th2 cytokines by immune cells, consequent to changed levels of steroid hormones during pregnancy. Consistent with the latter possibility, in vitro studies have demonstrated the ability of the steroid progesterone to increase IL-4 production and the ability of the steroid 17.beta.-estradiol to increase IL-10 production during T-lymphocyte responses. However, it remains unclear what cellular mechanisms are involved in regulating in vivo amelioration of autoimmune symptomology.

Examples of potential candidates which effect may effect MS during pregnancy include: Sex hormones (estrogens, progesterone), cortisol, vitamin D, alpha-fetoprotein, human chorionic gonadotropin and pregnancy specific glycoproteins.

Further, some studies have suggested that a unique pregnancy factor termed "early pregnancy factor" is responsible for improved progression of cell-mediated autoimmune diseases during pregnancy. Other studies have suggested a role for microchimerism. Still others suggest a role for local factors such as TGF.beta. or estriol (E3) which is known to be produced by the placenta during pregnancy. Of note, E3 is at its highest serum levels in the third trimester of pregnancy. However, E3's role in ameliorating symptoms of autoimmune diseases in humans is unclear.

Studies in laboratory animals have established that experimental autoimmune encephalomyelitis (EAE) and other Th1 (cell-mediated) autoimmune diseases in mice improve during pregnancy.

Specifically, treatment with late pregnancy levels of estriol or supraphysiological doses of estradiol (5 times pregnancy levels) were shown to delay the onset of clinical EAE after disease was experimentally induced by immunization of mice (Jansson et al. 1994). However, there was no investigation as to how estrogens delayed the day of onset of disease, nor as to whether disease severity was effected in these animals once symptomology occurred.

In another study, it was shown that EAE disease severity could be reduced by treatment with estriol, either before or after disease onset. Treatment of EAE mice with 90 day release pellets of 5 milligrams or 15 milligrams of estriol (E3) was shown not only to decrease disease severity but also to enhance autoantigen specific humoral-immunity, increase production of the Th2 cytokine IL-10 and reduced inflammation and demyelination in EAE mice. Importantly, these changes in the disease were induced by a dose (5 mg) which was shown to yield estriol levels in serum that were similar to those which occur during late pregnancy (Kim et al., Neurology, 50(4 Supp. 4):A242-245, April 1998, FASEB Journal 12(4):A616, March 1998 and Neurology 52(6): 1230-1238, April 1999; herein incorporated by reference). Thus, these results suggested that steroid hormones, and estriol in particular, may be involved in the amelioration of autoimmune reactions in the EAE animal model.

Other groups later demonstrated that estrogen potentiated the effects of treatment with TCR proteins to reduce autoimmune reactions in EAE mice. Offner, et al. FASEB Journal 14(6):A1246, April 2000; Int. Journal of Mol. Medicine 6 (Supp. 1): S8, October 2000 and Journal of Clin. Invest. 105(10):1465-1472, May 2000). Further, it was shown in animal studies that estrogen suppressed the onset EAE in mice (Ito, et al. Journal of Immunology, 167(1): 452-52, 2001) and that presumed diestrus levels of estrogens reduced some manifestations of active EAE in mice. Bebo et al. Journal of Immunology 166(3): 2080-9, 2001.

However, the etiology and disease progression of EAE and MS are not identical, thus it is unclear that estrogens alone would be effective in ameliorating autoimmune responses in human patients. Indeed, not only is it unknown whether pregnancy doses of estrogens might be protective in humans with autoimmune disease, it is unclear even in mice whether low doses of estrogens are protective. For example, it has been reported by some that ovariectomy of female mice makes EAE disease worse (Matejuk et al., 2001), while others have found that ovariectomy had no effect on disease severity (Kim et al., 2001; Voskuhl and Palaszynski, 2001a; Voskuhl and Palaszynski, 2001b). Thus, it is controversial whether low levels of estrogens, as they exist during the menstrual cycle, are protective even in mice.

Data from human studies to date have shown no clear benefit of steroids in treating any autoimmune disease. In humans, administration of available hormone therapies (including HRTs and OCPs) containing a mixture of sex hormones cause some autoimmune diseases to improve while others worsen.

For example, there has been no conclusive evidence that women are protected from or have a decrease in symptomology or relapse rates due to sex steroids. One study noted that past use of oral contraceptives in healthy women had no effect on subsequent risk to develop MS (Hernan et al. 2000). Further, another study found that the incidence rates for MS in current users were not decreased as compared to never-users (Thorogood and Hannaford, 1998). Thus, low dose of the estrogens in oral contraceptives are not of sufficient type or dose to ameliorate the immunopathogenesis of MS even temporarily during intercurrent use. At best, in one study, patients had the subjective impression that pre-existing MS symptoms (as opposed to relapse rates) worsen during the premenstrual period and that the use of oral contraceptives may have decreased this worsening (Zorgdrager and De Keyser, 1997). Importantly, the lack of reports of an effect of oral contraceptive therapy on MS relapses is in marked contrast to what has been observed during pregnancy.

In contrast, it has been shown that women had a lower the risk of developing MS during pregnancy compared to non-pregnant states (Runmarker and Andersen, 1995). Due to the numerous changes that occur during pregnancy, hormonal and nonhormonal (as listed above), the etiology of the beneficial effect of pregnancy may or may not be related to sex steroid fluctuations. It has also been reported for decades that pregnancy decreases MS relapses (Abramsky, 1994; Birk et al. 1990; Birk et al, 1998; Damek and Shuster, 1997; Runmarker and Andersen, 1995; Confavreux et al., 1998). These studies have shown that the latter part of pregnancy is associated with a significant reduction in relapses, while there is a rebound increase in relapses post partum. In contrast, the absence of such an effect on relapses during OCP or HRT indicate that low level sex steroids are not adequate to treat these symptoms.

Further, women having rheumatoid arthritis that were treated with HRT did not show significant improvement in their symptomology. DaSilva and Hall, Baillieres Clinical Rheumatology 1992, 6:196-219; Bijlsma at al. Journal of Repro. Imm. 28(3-4): 231-4, 1992; Hall et al. Annals of the Rheumatic Diseases, 53(2): 112-6, 1994.

Thus, the low doses of hormones found naturally during the menstrual cycle or in ORT and HRT have not been shown to be effective at ameliorating the symptomology of autoimmune diseases. This is in spite of the observation that women having MS have a decreased relapse rate during late pregnancy. Thus, a challenge has been to identify a hormone and a treatment dose that is therapeutic in treating particular autoimmune diseases, while minimizing undesirable side effects. Obviously, the dose and method of administration of steroids in humans differs from steroid treatment in laboratory animals due to toxic effects of prolonged exposure by patients to steroid hormones. In particular, there are clinical concerns of inducing breast or endometrial cancers in women requiring long term exposure to steroid hormones.

The actions of estrogen are mediated primarily by nuclear estrogen receptors (ER) ER alpha and ER beta, although non-genomic membrane effects have also been described previously. Originally it was thought that ER alpha and ER beta would each have distinct tissue distributions, thereby providing a means through which use of selective estrogen receptor modifiers. However, the relationship between ER alpha and ER beat became complex, with most tissues expressing some detectable level of each of these receptors. The two receptors at times did, and at other times did not, co-localize to the same cells within a given tissue. Furthermore, in some issues the two receptors were shown to act synergistically, whereas in the other tissues they act antagonistically. However, any selective effects by ER alpha and ER beta on MS and other auto-immune and Neurodegerative diseases have yet to be examined Further, the direct and indirect neuroprotective mechanisms by estrogens in EAE are not necessarily mutually exclusive, and have yet to be fully explored. The finding that estrogens are neuroprotective in EAE, regardless of mechanism, has relevance to estrogen treatment in MS, as well as pregnancy, a time when circulating estrogens are very high. Indeed, multiple pregnancies have been associated with a decrease in long-term disability accumulation in MS (Runmarker and Andersen, 1995; Damek and Shuster, 1997). Because it is known that up to 5 years of continuous treatment with immunomodulatory treatments are needed to impact disability in MS, a temporary anti-inflammatory effect of the third trimester of pregnancy would not necessarily be expected to improve long-term disability. While the efficacy of estrogen treatment appears to depend critically on its administration early, as a preventative therapy, before neurodegeneration has occurred (Mulnard et al., 2000), this therapeutic measure has yet to be explored.

Further, neurodegenerative diseases and disorders in addition to MS comprise a substantial clinical problem for which existing treatments have been ineffective at ameliorating the clinical symptomology or preventing the progression of the disease or disorder.

Estrogen treatment has been shown previously to be neuroprotective in a variety of neurodegenerative disease models including Parkinson's disease, cerebellar ataxia, stroke, and spinal cord injury (Leranth et al., 2000; Dubal et al., 2001; Wise et al., 2001; Jover et al., 2002; Rau et al., 2003; Sierra et al., 2003; Sribnick et al., 2003, 2005). Estrogens are lipophilic, readily traversing the blood-brain barrier, with the potential to be directly neuroprotective (Brinton, 2001; Garcia-Segura et al., 2001; Wise et al., 2001). Estrogen-mediated protection of neurons has been demonstrated in a variety of in vitro models of neurodegeneration including those induced by excitotoxicity and oxidative stress (Behl et al., 1995; Goodman et al., 1996; Behl et al., 1997; Harms et al., 2001). Estrogens have also been shown to decrease glutamate-induced apoptosis and preserve electrophysiologic function in primary cortical neurons (Sribnick et al., 2003, 2004). In addition, in vitro studies have demonstrated the ability of estrogen to modulate the astrocytic response to injury (Azcoitia et al., 1999; Garcia-Segura et al., 1999) and protect oligodendrocytes from cytotoxicity (Sur et al., 2003; Cantarella et al., 2004; Takao et al., 2004). However, the role of estrogen and estrogen receptor subtypes involved neuroprotection has yet to be fully explored.

INVENTION SUMMARY

A general object of the present invention is to provide a method of administering steroid hormones to mammals to treat autoimmune related diseases, more particularly, Th1-mediated (cell-mediated) autoimmune diseases including: multiple sclerosis (MS), rheumatoid arthritis (RA), autoimmune thyroiditis, uveitis and other autoimmune diseases in which clinical symptomology has shown improvement during the third term of pregnancy. The method may also include the treatment of post-partum patients having been diagnosed with, or at risk for developing autoimmune diseases, including MS. The method may also include the treatment of patients having been diagnosed with, or at risk for developing neurodegenerative diseases, including MS.

In accordance with one aspect of the present invention, these objectives are accomplished by providing a treatment for autoimmune related diseases with a selected dose and course of a primary agent being an estrogen or estrogen receptor-effective composition. The primary agent may include estrogen receptor selective ligands, such as agonists which mimic the effect of estrogens.

In accordance with one aspect of the present invention, these objectives are accomplished by providing a patient with a therapeutically effective amount of estriol, comprising from about 4 to 16 milligrams per day, or more specifically, about 8 milligrams once daily via oral administration.

In accordance with another aspect of the present invention, these objectives are accomplished by providing a therapeutically effective amount of a primary agent in combination with a therapeutically effective amount of a secondary active agent, such as progesterone, glucocorticoids and/or known or experimental drugs used to treat autoimmune diseases.

In accordance with one aspect of the present invention, the invention comprises the use of a primary agent comprising an estrogen receptor alpha ligand having anti-inflammatory and/or neuroprotective effects to prevent or ameliorate clinical symptoms of autoimmune and/or neurodegenerative diseases or disorders, including multiple sclerosis.

In accordance with one aspect of the present invention, the invention comprises the use of a primary agent comprising an estrogen receptor beta ligand having neuroprotective effects to prevent or ameliorate clinical symptoms of neurodegenerative diseases or disorders, including multiple sclerosis.

The above described and many other features and attendant advantages of the present invention will become apparent from a consideration of the following detailed description when considered in conjunction with the accompanying drawings.

BRIEF DESCRIPTION OF THE DRAWINGS

FIG. 1A is a schematic depicting the trial design described in Example 1; FIG. 1B is a bar graph depicting human serum levels during pregnancy, estriol treatment (Tx), and pretreatment (Pre Tx levels).

FIGS. 3A-F are bar graphs depicting each patient's gadolinium enhancing lesion volumes on serial cerebral MRIs which were assessed at each month during the pretreatment, estriol treatment and post treatment periods.

FIG. 4 is a bar graph depicting mean percent change in PASAT scores during treatment with estriol as compared to pretreatment.

FIGS. 5A-C are bar graphs showing the uterine weights of wild type (WT), ER beta knock-out (KO), or ER alpha KO in mice treated with a control (vehicle), estrogen receptor alpha ligand (PPT) or estradiol treated animals (y-axis=uterine weight in grams).

FIGS. 8A-E depict various measures of estrogen receptor alpha ligand reduced inflammation and demyelination in spinal cords of mice with EAE. FIG. 8A are thoracic spinal cord sections from normal, or treated mice (vehicle, estradiol (E2) or estrogen receptor alpha ligand (PPT)); FIG. 8B depicts luxol fast-blue stained magnified regions of the dorsal spinal column for the same sections as shown in 8A (40× magnification); FIG. 8C depicts anti-BMP immunostained magnified regions of the dorsal spinal column for the same sections as shown in 8A; FIG. 8D is a bar graph showing white matter cell density by treatment group; and FIG. 8E is a bar graph showing myelin density by treatment group.

FIGS. 9A-D are split images of thoracic spinal cord sections stained with NeuN+ (red) in I and Nissl in ii at 4× magnification, derived from mice from each treatment group (normal, vehicle, estradiol (E2) or estrogen receptor alpha ligand (PPT)). FIG. 9E is a bar graph showing the number of NeuN+ immunolabeled neurons in the delineated gray matter.

FIGS. 10A-D depict various measures of estrogen receptor alpha ligand reduced inflammation and demylination in spinal cords of mice with EAE. FIGS. 10A and B are images of thoracic spinal cord sections shown in FIG. 5 co-immunostained with NF200 (green) and CD45 (red) at 10× magnification, derived from mice from each treatment group (normal, vehicle, estradiol (E2) or estrogen receptor alpha ligand (PPT)). FIG. 10C is a bar graph showing the axon number and FIG. 10D is a bar graph showing Mac-3 cell density measurements.

FIGS. 12A-G are graphs showing the effect on clinical scores of wild type (WT), estrogen receptor alpha ligand (PPT) and estrogen receptor beta ligand (DPN) treated animals.

FIGS. 14A-F depict various measures of estrogen receptor alpha ligand reduced inflammation and demyelination in spinal cords of mice with EAE. FIGS. 14A and 14C are early and late thoracic spinal cord sections from normal, or treated mice (vehicle, estrogen receptor alpha (PPT) or estrogen receptor beta ligand (DPN)); FIG. 14B depicts early white matter cell density for each treatment group; FIG. 14D depicts late white matter cell density for each treatment group; 14 E and F depict early and late sections co-immunostained with NF200 (green) and CD45 (red) at 10× magnification, derived from mice from each treatment group.

FIGS. 15A-H depict various measures of estrogen receptor alpha and beta ligand preservation of MBP and spare axonal pathology in spinal cords of EAE mice. FIGS. 15A and 15C are images of thoracic spinal cord sections stained with NeuN (red) 10× magnification, derived from mice at early and late time points from each treatment group (normal, vehicle, estrogen alpha ligand (PPT) or estrogen receptor beat ligand (DPN)). FIGS. 15E and 15G are images of thoracic spinal cord sections co-immunostained with anti-NF200 (green, i) and anti-BMP (red, ii), shown merged in iii, derived from mice at early and late time points from each treatment group (normal, vehicle, estrogen alpha ligand (PPT) or estrogen receptor beat ligand (DPN)); FIGS. 15B and 15D are bar graphs showing myelin density, early and late, respectively, while FIGS. 15F and 15H show axon number, early and late, respectively.

FIGS. 16A-C depict various measures of estrogen receptor alpha and beta ligand preservation of neuronal staining of gray matter in spinal cords of mice with EAE. FIGS. 16B and 16D are bar graphs showing quantification of NeuN+ cells in the gray matter.

DETAILED DESCRIPTION OF THE PREFERRED EMBODIMENTS

Figure 2A:
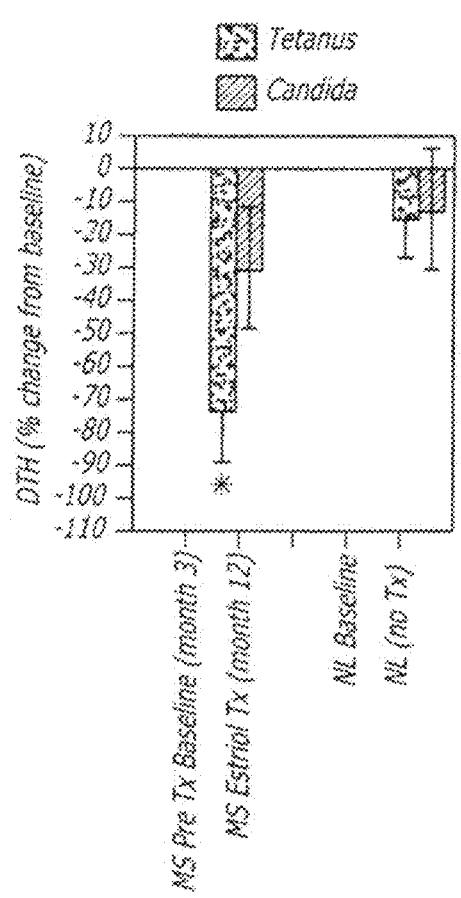
FIG. 2A is a bar graph describing the Delayed Type Hypersensitivity (DTH) responses to tetanus and to *candida*.

This description is not to be taken in a limiting sense, but is made merely for the purpose of illustrating the general principles of the invention. The section titles and overall organization of the present detailed description are for the purpose of convenience only and are not intended to limit the present invention.

Generally, the invention involves a method of treating mammal exhibiting clinical symptoms of an autoimmune disease comprising administering a primary agent at a therapeutically effective dosage in an effective dosage form at a selected interval. The treatment is aimed at reducing the symptomology and/or progression of the disease. In the preferred embodiment of the invention, human patients clinically diagnosed with MS (including both relapsing remitting or secondary progressive type patients) are treated with an oral preparation of 8 milligrams estriol daily and have ameliorated symptomology.

Amelioration of the autoimmune disease refers to any observable beneficial effect of the treatment. The beneficial effect can be evidenced by a delayed onset or progression of disease symptomology, a reduction in the severity of some or all of the clinical symptoms, or an improvement in the overall health.

For example, patients who have clinical symptoms of an autoimmune disease often suffer from some or all of the following symptoms: worsening of pre-existing symptoms (such as joint pain in rheumatoid arthritis), the appearance of new symptoms (new joints affected in rheumatoid arthritis) or increased generalized weakness and fatigue. MS patients in particular suffer from the following symptoms: weakness, numbness, tingling, loss of vision, memory difficulty and extreme fatigue. Thus an amelioration of disease in MS would include a reduction in the frequency or severity of onset of weakness, numbness, tingling, loss of vision, memory difficulty and extreme fatigue. On imaging of the brain (MRI) amelioration of disease would be evidenced by a decrease in the number or volume of gadolinium enhancing lesions, a stabilization or slowing of the accumulation of T2 lesions and/or a slowing in the rate of atrophy formation. Immunologically, an increase in Th2 cytokines (such as IL-10) a decrease in Th1 cytokines (such as interferon gamma) would be associated with disease amelioration.

Patients may also express criteria indicating they are at risk for developing autoimmune diseases. These patients may be preventatively treated to delay the onset of clinical symptomology. More specifically, patients who present initially with clinically isolated syndromes (CIS) may be treated using the treatment paradigm outlined in this invention. These patients have had at least one clinical event consistent with MS, but have not met full criteria for MS diagnosis since the definite diagnosis requires more than one clinical event at another time (McDonald et al., 2001). Treatment of the present invention would be advantageous at least in preventing or delaying the development of clinically definite MS.

PRIMARY AGENT. The primary agent useful in this invention is a steroid hormone, more particularly a estrogen or a steroidal or non-steroidal estrogen receptor active agent. Most preferably the primary agent is estriol (estra-1,3,5(10)-triene-3,16,17-triol), E3, such as estriol succinate, estriol dihexanate or estriol sulfmate. However, the primary agent may be precursors or analogs of estriol (such as nyestriol), estrone (E1) or precursors or analogs of estrone, 17.beta.-estradiol (E2) or precursors (including aromatizable testosterone) or analogs of 17.beta.-estradiol, or estranges.

The primary agent may also be a metabolite or derivatives of E1, E2 or E3 which are active at the estrogen receptor .alpha. or .beta. Metabolites and derivatives may have a similar core structure to E1, E2 or E3 but may have one or more different groups (ex. hydroxyl, ketone, halide, etc.) at one or more ring positions. Synthetic steroids which are effective at estrogen receptor are also useful in this invention, such as those described in WO 97/08188 or U.S. Pat. No. 6,043,236 to Brattsand, which is hereby incorporated by reference herein.

The primary agent may also be an estrogen receptor .alpha. or .beta., agonists and/or antagonist. These agonists or antagonists may be steroidal or non-steroidal agents which bind to and/or cause a change in activity or binding of at least one of the estrogen receptor .alpha. or .beta. subtypes. For example, specific agonists of ER alpha and ER beta may be useful in this invention (Fritzmeier, et al.). Doses of these agonists may be titrated to achieve an effect on disease similar to that which is observed during pregnancy and during treatment with pregnancy doses of estriol by methodologies known to those skilled in the art of steroid pharmacology.

Any one or combination of these estrogens or estrogen receptor active agents may be used to treat the selected autoimmune disease. The selection of the estrogens or estrogen receptor active agents can be made considering secondary side effects of the treatment to the patient. For example, estriol may be selected over 17.beta.-estradiol, because estriol causes minimal endometrial proliferation and is not associated with increased risk of breast cancer. Minimal endometrial proliferation is observed when the long-acting estriol derivative, nyestriol is used. Indeed, because estriol has partial antagonist action on the binding of 17.beta.-estradiol to the estrogen receptor in vivo, estriol was at one point in the past considered as a therapeutic agent for treatment and prevention of breast cancer.

THERAPEUTICALLY EFFECTIVE DOSAGE OF THE PRIMARY AGENT. A therapeutically effective dose of the primary agent is one sufficient to raise the serum concentration above basal levels, and preferably to pregnancy levels or above pregnancy levels. Most preferably, the therapeutically effective dosage of the primary agent is selected to result in serum levels in a patient equivalent to the steroid hormone level of that agent in women in the second or third trimester of pregnancy.

For example, during the normal female menstrual cycle estradiol levels are in the range of about 350 pg/ml serum. During pregnancy, there is about a 100 fold increase in the level of estradiol to about 10,000 to about 35,000 pg/ml serum. (Correale, et al. Journal of Immunology 161:3365 (1998) and Gilmore, et al. Journal of Immunology 158:446). In contrast, estriol levels are undetectable during the menstrual cycle in the non-pregnant state. Estradiol levels rise progressively during pregnancy to levels from 3,000 to 30,000 pg/ml (3 to 30 ng/ml) (www.il-st-acad-sci.org/steroid 1.html#se3t).

In one embodiment, where the primary agent is estriol, the preferable dose is from about 4 to 16 milligrams daily, and more specifically, about 8 milligrams daily. In this embodiment, blood serum levels preferably reach at least about 2 ng/ml, may reach about 10 to about 35 ng/ml, or most preferably about 20-30 ng/ml. (Sicotte et al. Neurology 56:A75). In some embodiments, estradiol (E2) levels would preferably reach at least about 2 ng/ml and most preferably about to 10-35 ng/ml. In some embodiments, estrone (E1) levels would preferably reach at least about 2 ng/ml and most preferably about 5-18 ng/ml (DeGroot and Jameson, 1994).

The dosage of the primary agent may be selected for an individual patient depending upon the route of administration, severity of disease, age and weight of the patient, other medications the patient is taking and other factors normally considered by the attending physician, when determining the individual regimen and dosage level as the most appropriate for a particular patient.

The use of this group of primary agents is advantageous in at least that other known or experimental treatments for cellular mediated autoimmune diseases are chemotherapeutic immunosuppressants which have significant risks and side effects to patients, including decreasing the ability of the patient to fight infections, inducing liver or heart toxicity which are not caused by estrogen treatment. Other agents used in MS do not cause these side effect, but are associated with flu-like symptoms or chest tightness. Further, these previously used agents are associated with local skin reactions since they entail injections at frequencies ranging from daily to once per week.

DOSAGE FORM. The therapeutically effective dose of the primary agent included in the dosage form is selected at least by considering the type of primary agent selected and the mode of administration. The dosage form may include the active primary agent in combination with other inert ingredients, including adjutants and pharmaceutically acceptable carriers for the facilitation of dosage to the patient as known to those skilled in the pharmaceutical arts. The dosage form may be any form suitable to cause the primary agent to enter into the tissues of the patient.

In one embodiment, the dosage form of the primary agent is an oral preparation (liquid, tablet, capsule, caplet or the like) which when consumed results in elevated serum estrogen levels. The oral preparation may comprise conventional carriers including dilutents, binders, time release agents, lubricants and disinigrants.

In other embodiments of the invention, the dosage form may be provided in a topical preparation (lotion, creme ointment or the like) for transdermal application. Alternatively, the dosage form may be provided in a suppository or the like for transvaginal or transrectal application.

That estrogens or estrogen receptor active agents can be delivered via these dosage forms is advantageous in that currently available therapies, for MS for example, are all injectables which are inconvenient for the user and lead to decreased patient compliance with the treatment. Non-injectable dosage forms are further advantageous over current injectable treatments which often cause side effects in patients including flu-like symptoms (particularly, .beta. interferon) and injection site reactions which may lead to lipotrophy (particularly, glatiramer acetate copolymer-1).

However, in additional embodiments, the dosage form may also allow for preparations to be applied subcutaneously, intravenously, intramuscularly or via the respiratory system.

SECONDARY ACTIVE AGENTS. Any one or a combination of secondary active agents may be included in the dosage form with the primary agent. Alternatively, any one or a combination of secondary active agents may be administered independently of the primary agent, but concurrent in time such that the patient is exposed to at least two agents for the treatment of their immunological disease.

The secondary agents are preferably immunotherapeutic agents, which act synergistically with the primary agent to diminish the symptomology of the autoimmune disease. Secondary active agents may be selected to enhance the effect of the estrogen or estrogen receptor active agent, reduce the effect of the estrogen or estrogen receptor active agent or effect a different system than that effected by the estrogen or estrogen receptor active agent.

Secondary active agents include immunotherapeutic agents which cause a change in the activity or function of the immune system.

In one embodiment, a secondary agent may be a therapeutically effective amount of progesterone, precursor, analog or progesterone receptor agonist or antagonist. Most preferably, the secondary agent is 100-200 milligrams of progesterone administered daily. Progesterone in combination with estrogen or estrogen receptor active agent treatment is advantageous in at least protecting patients against risks associated with long term estrogen exposure, including, but not limited to endometrial proliferation and breast cancers.

In another embodiment, a secondary agent may be a therapeutically effective amount of glucocorticoid, precursor, analog or glucocorticoid receptor agonist or antagonist. For example, prednisone may be administered, most preferably in the dosage range of about 5-60 milligrams per day. Also, methyl prednisone (Solumedrol) may be administered, most preferably in the dosage range of about 1-2 milligrams per day. Glucocorticoids are currently used to treat relapse episodes in MS patients, and symptomatic RA within this dosage range.

In other embodiments, a secondary agent may be selected from the group immunotherapeutic compounds. For example, as .beta.-interferon (Avonex® (interferon-beta 1a), Rebiff® (by Serono); Biogen, Betaseron® (interferon-beta 1b) Berlex, Schering), glatiramer acetate copolymer-1 (Copaxone®; Teva), antineoplastics (such as mitoxantrone; Novatrone® Lederle Labs), human monoclonal antibodies (such as natalizumab; Antegren® Elan Corp. and Biogen Inc.), immonusuppressants (such as mycophenolate mofetil; CellCept® Hoffman-LaRoche Inc.), paclitaxel (Taxol®; Bristol-Meyers Oncology), cyclosporine (such as cyclosporin A), corticosteroids (glucocorticoids, such as prednisone and methyl prednisone), azathioprine, cyclophosphamide, methotrexate, cladribine, 4-aminopyridine and tizanidine and natalizumab (Tysabri)

By way of example, which is consistent with the current therapeutic uses for these treatments, Avonex® in a dosage of about 0 to about 30 mcg may be injected intramuscularly once a week. Betaseron® in a dosage of about 0 to about 0.25 mg may be injected subcutaneously every other day. Copaxone® in a dosage of about 0 to about 20 mg may be injected subcutaneously every day. Finally, Rebiff® may be injected at a therapeutic dose and at an interval to be determined based on clinical trial data. Further, any of these secondary agents may be used in increasing, constant or decreasing dose in combination with a primary agent, such as estriol or an ER alpha or beta receptor ligand. However, dosages and method of administration may be altered to maximize the effect of these therapies in conjunction with estrogen treatment. Dosages may be altered using criteria that are known to those skilled in the art of diagnosing and treating autoimmune diseases.

Preferably, secondary agents would be administered in the dosage ranges currently used to treat patients having autoimmune diseases, including MS patients. Alternatively, the secondary agents may be administered at a reduced dose or with reduced frequency due to synergistic or duplicative physiological effects with the primary agent.

Preferably, patients exhibiting symptomology of autoimmune diseases are treated with the above agents (estrogen or estrogen receptor active agents with or without secondary agents). Most preferably, patients exhibit autoimmune diseases marked by improvement in symptomology at least during a treatment regimen, including but not limited to that reflecting patterns observed during the second or third trimester of pregnancy.

Treatment of Post-Partum Patients.

In a recent clinical study, a dramatic decrease in the relapse rate during pregnancy, especially in the third trimester was noted, with a rebound increase in the three months post partum (such as a patient who has given birth, including until the following year from the date of birth). These data, in addition to confirmatory animal testing using the EAE model suggest that sex steroids have profound effects in autoimmune disease progression and symptomology, and could also have an effect on myelinating and re-myelinating the peripheral and possibly the central nervous system.

In another embodiment of the invention, the invention may include methods of steroidal therapies for preventing or treating female post-partum patients, expressing symptoms of or at risk for autoimmune diseases. The invention may include the method of preventing or treating a subject having been diagnosed with at least one symptom of an autoimmune disease to reduce the symptomology of/and or slow the progression of the disease. The method according to the invention may comprise administering primary agents being estrogens or estrogen receptor active agents for the treatment of cell mediated diseases. The invention may further include the treatment with secondary agents which effect the immune system, which may be co-administered or tapered onto. In other embodiments, the use of the primary agents, combinations of primary agents with secondary agents, at the doses and in the dosage forms may be administered as described above for auto immune diseases.

In one embodiment of the invention, human post-partum patients who are clinically diagnosed with an autoimmune disease, such as MS (including both relapsing remitting or secondary progressive type patients) may be treated with an oral preparation of 8 milligrams estriol daily, resulting in ameliorated symptomology. Additionally, patients could be administered an estriol or an estrogen following birth, then tapered onto a conventional FDA approved therapy, such as Copaxone.

Amelioration of the post-partum autoimmune disease refers to any observable beneficial effect of the treatment. The beneficial effect can be evidenced by a delayed onset or progression of disease symptomology, a reduction in the severity of some or all of the clinical symptoms, or an improvement in the overall health.

For example, patients who have clinical symptoms of an autoimmune disease often suffer from some or all of the following symptoms: worsening of pre-existing symptoms (such as joint pain in rheumatoid arthritis), the appearance of new symptoms (new joints affected in rheumatoid arthritis) or increased generalized weakness and fatigue. Multiple sclerosis patients in particular suffer from the following symptoms: weakness, numbness, tingling, loss of vision, memory difficulty and extreme fatigue. Thus an amelioration of disease in multiple sclerosis would include a reduction in the frequency or severity of onset of weakness, numbness, tingling, loss of vision, memory difficulty and extreme fatigue. On imaging of the brain (MRI) amelioration of disease would be evidenced by a decrease in the number or volume of gadolinium enhancing lesions, a stabilization or slowing of the accumulation of T2 lesions and/or a slowing in the rate of atrophy formation. Immunologically, an increase in Th2 cytokines (such as IL-10) a decrease in Th1 cytokines (such as interferon gamma) would be associated with disease amelioration.

Patients may also express criteria indicating they are at risk for developing autoimmune diseases. These patients may be preventatively treated to delay the onset of clinical symptomology. More specifically, patients who present initially with clinically isolated syndromes (CIS) may be treated using the treatment paradigm outlined in this invention. These patients have had at least one clinical event consistent with MS, but have not met full criteria for MS diagnosis since the definite diagnosis requires more than one clinical event at another time (McDonald et al., 2001). Treatment of the present invention would be advantageous at least in preventing or delaying the development of clinically definite MS.

Treatment with Primary Agents being ER Alpha Receptor Agonists.

In one embodiment, the invention comprises the use of a primary agent comprising an estrogen receptor alpha ligand, such as an agonist, having an anti-inflammatory and neuroprotective effect to prevent or ameliorate clinical symptoms of auto immune diseases including multiple sclerosis.

As above, multiple sclerosis is an inflammatory, neurodegenerative disease for which experimental autoimmune encephalomyelitis (EAE) is a model. Treatments with estrogens have been shown to decrease the severity of EAE through anti-inflammatory and neuropreservation mechanisms. More recently, it has been determined that estrogen receptor alpha (ER alpha) ligand could recapitulate the estrogen-mediated protection in clinical EAE. As described in the examples below, EAE treatment with a highly selective ER alpha agonist (propyl pyrazole triol) ameliorated clinical disease in both wild-type and ER beta knock-out mice, but not in ER alpha knock-out mice, suggesting that the ER alpha ligand maintained ER alpha selectivity in vivo during disease. Anti-inflammatory and neuroprotective effects included, reduced auto-antigen-specific pro-inflammatory cytokine production, increased anti-inflammatory cytokines, reduced nervous system inflammation, reduced demyelination, reduction in neuronal cell loss, reduction in axonal transaction, decreased white matter lesions, decreased loss in axonal number, reduced nervous system monocyte activation and reduced nervous system microglial activation. See Examples 5 and 6 and FIGS. 5-10.

Treatment of Patients with Neurodegenerative Diseases/Disorders.

In another embodiment of the invention, the invention comprises the treatment of neurodegenerative diseases and disorders, including MS. The invention may include the method of preventing or treating a subject having been diagnosed or exhibiting at least one clinical symptom of a neurodegenerative disease or disorder.

The method according to the invention may comprise administering a primary agent at a therapeutically effective dosage in an effective dosage form at a selected interval to prevent, reduce the frequency or reduce the severity of the symptoms and/or progression of the disease or disorder.

In one specific embodiment, the method may comprise administration of 8 milligrams estriol daily, such as in an oral preparation and result in ameliorated symptomology. In one other embodiment, the method may comprise treating the patent with a combination of estrogen and progestin or progesterone, as a secondary agent. In other embodiments, the use of the primary agents, combinations of primary agents with secondary agents, at the doses and in the dosage forms may be administered as described above for auto immune diseases.

In other embodiments, the primary agent may comprise an estrogen receptor beta ligand, such as a estrogen receptor beta agonist. In the EAE animal model, an estrogen receptor beta agonist was found to have significant neuroprotective effects, including reduced demyelination, reduces axon loss, reduces neuronal abnormalities and reduced motor impairment, and reduced relapses. See Example 6 and FIGS. 11-18, below.

Neurodegenerative diseases and disorders for which the invention may be effective include, but are not limited to: Alzheimer's disease, Parkinson's disease, multiple sclerosis, stroke, amyotrophic lateral sclerosis (Lou Gehrig's Disease), frontotemporal dementia (Pick's Disease), prion disease and Huntington's disease. Additional disorders that may be treated on the basis of the pharmacological results with estrogens or estrogen receptor active agents, include, but are not limited to cerebral ischemia, idiopathic Morbus Parkinson, topically- or drug-induced Parkinson syndrome, Morbus Alzheimer and cerebral dementia syndromes of different origin, Huntington's chorea, infectious-induced neurodegeneration disorders such as AIDS-encephalopathy, Creutzfeld-Jakob disease, encephalopathies induced by rubiola and herpes viruses and borrelioses, metabolic-toxic neurodegenerative disorders such as hepatic-, alcoholic-, hypoxic-, hypo- or hyperglycemically-induced encephalopathies as well as encephalopathies induced by solvents or pharmaceuticals, degenerative retina disorders of various origin, traumatically-induced brain and bone marrow damage, cerebral hyperexcitability symptoms of varying origin such as after the addition of and/or withdrawal of medicaments, toxins, noxae and drugs, mentally and traumatically-induced cerebral hyperexcitability states, neurodegenerative syndromes of the peripheral nervous system, such as metabolism, medicament, toxically- and infectiously-induced polyneuropathies and polyneuritis, and the bronchospasmolytic effect.

KITS. In another aspect of this invention kits are provided for use by the treating physician in the clinic or prescribed patient for self-administration of treatment. The kits of this invention include at least one primary agent and one secondary agent in the appropriate dosages and dosage form for the treatment of the patient's clinical symptoms.

In a first embodiment of the kit, the primary agent is estriol in doses of about 4-16 milligrams and the secondary agent is progesterone in doses of about 100 to about 200 milligrams. In a second embodiment of this kit, the primary agent is estriol in doses of about 4-16 milligrams and the secondary agent is a glucocorticoid, such as prednisone (about 5-60 milligrams per day) or methyl prednisone (1-2 milligrams per day).

In a third embodiment of this invention, the primary agent is estriol in doses of about 4-16 milligrams and the secondary agent is .beta.-interferon in doses of about 0.25 milligrams of Betaseron® or 30 mcg of Avonex® In a fourth alternate embodiment of the kit, the primary agent is estriol in doses of about 4 to about 16 milligrams and the secondary agent is glatiramer acetate copolymer in doses of about 20 milligrams of Copaxone®.

The kit also preferably contains instructions for use of the kit by the use by the treating physician or patients to treat their autoimmune disease. Such information would include at least the schedule for the administration of the primary agent dose and the secondary agent dose.

Although the present invention has been described in terms of the preferred embodiment above, numerous modifications and/or additions to the above-described preferred embodiments would be readily apparent to one skilled in the art.

Example 1

Methods: Trial Design.

A crossover design was used with monthly brain MRIs during the six month pretreatment period, the six month treatment period with oral estriol (8 milligrams/day) and the six month post treatment period, with clinical and laboratory evaluations as demonstrated (FIG. 1A).

Inclusion Criteria.

Women with clinically definite MS, ages 18-50, with an EDSS 0-6.5 who had been off interferon beta and copolymer-1 for at least six months, and had no steroid treatment for at least three months were eligible. At least 5 cm$^3$ of lesion burden on a screening T2 weighted brain MRI was required. Subjects who were pregnant or nursing, on oral contraceptives or hormone replacement therapy, or who had a history of thrombosis, neoplasm or gynecologic disease, or who had been treated in the past with total lymphoid irradiation, monoclonal antibody, T cell vaccination, cladribine or bone marrow transplantation were excluded.

Patients.

Twelve female patients with clinically definite MS were enrolled. Six had RR disease and six had SP disease. All six RR and four of six SP patients completed the entire 18 month study period. One SP patient was discontinued from the study because of prolonged treatment with steroids for tonic spasms by an outside neurologist and the other did not wish to go untreated in the post treatment period. Of the ten patients who completed the entire study, the mean age was 44 years (range 28 to 50 years) and the mean EDSS was 3.3 (range 1.0 to 6.5). The mean EDSS score for the SP patients was 5.0 while the mean EDSS for the RR patients was 2.2. The 18 month trial was extended in RR patients whereby treatment was re-instituted. Medication. For the initial treatment phase, micronized, U.S.P. graded estriol powder (Medisca, Inc., Plattsburg, N.Y.) was put into capsules by UCLA Pharmaceutical Services. During the extension re-treatment phase in the RR patients, all but one received a capsule of estriol (8 milligrams/day) plus progesterone (100 milligrams/day), while the single RR patient who had a hysterectomy received only estriol (8 milligrams/day) (Women's International Pharmacy, Madison, Wis.).

Clinical and Safety Measures.

Subjects were evaluated using the Kurtzke's Expanded Disability Status Scale (EDSS) by the same neurologist (RV) throughout the study. At each visit the study nurse (RK) administered the paced auditory serial addition test (PASAT) and the 9-hole peg test. Blood was drawn for SMA12, cholesterol panel, blood counts and hormone levels (estriol, estradiol, estrone, LH, FSH, cortisol, progesterone). Estriol levels in serum were determined by ELISA according to manufacturer's instructions (Oxford Biomedical, Oxford, Mich.).

Delayed Type Hypersensitivity Responses (DTH).

DTH to tetanus (Tetanus Toxoid, Wyeth Laboratories, Marietta, Pa.) and *candida* (Candin, Allermed Laboratories, San Diego, Calif.) were tested at two timepoints, once in the pretreatment period at study month 3 and once at the end of the treatment period at study month 12 (FIG. 1A). A group of six untreated healthy control women were also tested twice, spanning the same time interval (9 months). 0.1 ml of each solution was injected intradermally on the anterior surface of the forearm. Induration at each injection site was read after 48 hours. Each site was measured twice, once vertically and once horizontally with the average recorded. The same nurse (RK) administered all injections and read all responses on all subjects at both time points.

Reverse Transcription and Polymerase Chain Reaction.

Peripheral blood mononuclear cells (PBMCs) were isolated from heparinized venous blood and cryopreserved. PBMCs were thawed in parallel from a given patient during the two pre-treatment timepoints and the two treatment timepoints. Total RNA was isolated, DNA was removed and mRNA was reverse transcribed. Both IFN-$\gamma$ and actin were amplified from the same cDNA, however, the cDNA was diluted 1:9 prior to amplification for actin. Amplification was done in 1 mM MilligramsCl$_2$ using IFN.$\gamma$ and actin primer sequences (Life Technologies, Rockville, Md.). Complementary DNA was amplified for 35 cycles: 45" @ 95° C., 60" @ 54° C. and 45" @ 72° C. PCR products were separated on a 1.5% agarose gel containing ethidium bromide and densitometry performed.

MRIs. Scans were performed on a 1.5 T G.E. scanner. The pulse sequences obtained were a T1-weighted scan with and without gadolinium (Omniscan 0.1 mmol/kg) and a PD/T2 weighted scan. Digitized image data was transferred to a SGI workstation (Silicon Graphics, Inc) for further processing. The number and volume of new and total gadolinium enhancing lesions was determined using a semiautomated threshold based technique (Display, Montreal Neurological Institute) by a single experienced operator (NS). The operator was blinded as to whether patients had RR or SP disease. To calculate T2 volumes, a custom semiautomated, threshold based, seed-growing algorithm was used to determine lesion volume after skull stripping, rf correction and spatial normalization. All scans were counted by the same technician who was blinded as to whether patients had RR or SP disease.

Statistical Analysis.

One sample, paired, t tests were used to ascertain significance of percent changes in DTH responses, IFN.gamma. levels and PASAT cognitive testing scores during treatment as compared to pretreatment. The nonparametric, Wilcoxon's signed rank test was used for statistical comparisons in enhancing lesion numbers and volumes on MRI between the six month baseline period and each treatment period, post treatment period and re-treatment period.

Results.

Estriol levels and tolerability. Serum estriol levels during treatment and re-treatment approximated those observed in women who were six months pregnant, but were lower than those who were 8.5 months pregnant (FIG. 1B). Consistent with previous reports, estriol was well tolerated with only menstrual cycle abnormalities. There were no significant alterations in any laboratory measures including LH, FSH, cortisol, progesterone, estradiol and estrone.

Immune Responses.

Skin testing to tetanus and-*candida* were performed once in the pretreatment period and once at the end of the treatment period to determine whether they might be decreased with treatment. DTH responses to tetanus were significantly, P=−0.006, decreased at study month 12, when patients had been on estriol for six months, as compared to DTH responses at study month 3, the pretreatment baseline (FIG. 2A). DTH responses to *candida* were decreased less dramatically and more variably. The significant decrease in DTH responses to tetanus from pretreatment (month 3) to treatment (month 12) was not merely due to repeat testing at nine months since healthy, untreated female controls tested at baseline, then again after nine months, did not demonstrate a significant decrease in DTH responses as compared to their baseline. These findings are consistent with an estriol induced down-regulation of Th1 responses in vivo during treatment.

Figure 2B:
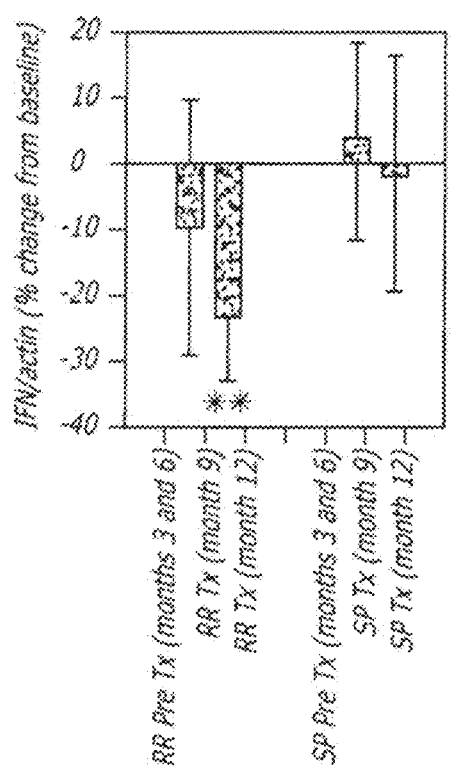
FIG. 2B is a bar graph depicting levels of IFN.gamma. between treatment groups.

IFN.gamma. is a signature cytokine for Th1 responses. Therefore, we assessed IFN.gamma. levels by RT-PCR of unstimulated peripheral blood mononuclear cells (PBMCs) derived ex vivo from patients during the pretreatment and the treatment periods. In the six RR patients, levels of IFN.gamma. were variably decreased at study month 9 (after three months of estriol treatment) and then significantly decreased, P=–0.003, at study month 12 (after six months of estriol treatment) as compared to baseline pretreatment levels (months 3 and 6) (FIG. 2B). In contrast, there was no decrease in IFN.gamma. in the four SP patients. These data are consistent with the concept that the immune system of RR patients, as compared to SP patients, may be more amenable to treatments that aim to decrease Th1 responses. Also, the observation that estriol treatment can alter cytokine production by PMBCs is consistent with reports demonstrating estrogen receptors .alpha. and .beta. in immune tissues and cells.

MRIs.

Based on the protective effect of pregnancy on relapse rates in MS patients and the association of gadolinium enhancing lesions with relapses, we hypothesized that estriol treatment would have an anti-inflammatory effect as manifested by decreases in enhancing lesions on serial brain MRIs. Compared to the six month pretreatment baseline period, the total volume and number of enhancing lesions for all ten MS patients (6RR, 4SP) decreased during the treatment period. This improvement in the group as a whole was driven by the beneficial effect of estriol treatment in the RR, not the SP, group (FIGS. 3A and 3B). Therapeutic effects of estriol treatment in the RR group were therefore examined in further detail. Within the first three months of treatment of RR patients, median total enhancing lesion volumes were decreased by 79%, P=0.02, and numbers were decreased by 82%, P=0.09 (FIGS. 3C and 3D). They remained decreased during the next three months of treatment, with lesion volumes decreased by 82%, P=0.01, and numbers decreased by 82%, P=0.02. In the post treatment period, median total enhancing lesion volumes and numbers became variable in the first three months off treatment, before returning to near baseline levels in the last three months of the post treatment period. During the four month re-treatment extension phase, enhancing lesion volumes decreased again by 88%, P=0.008, and numbers decreased again, this time by 48%, P=0.04, as compared to original baseline (FIGS. 3C and 3D). Changes in median new enhancing lesion volumes and numbers followed similar patterns as median total lesion numbers and volumes (FIGS. 3E and 3F).

Median T2 lesion volumes for the whole group were 15.3 cm.sup.3 (range 6.1-33.8), with no significant differences in median T2 volumes between RR and SP groups. Consistent with enhancing lesion data, serial T2 lesion volumes revealed that estriol treatment tended to be most beneficial in RR patients. In the RR group, median T2 lesion volumes remained stable during the six month treatment period (0% change), increased during the six month post treatment period (7.4% higher), and then declined in the four month re-treatment extension period (2.0% lower).

Clinical Measures. Relapses were few and showed no significant changes during the study. In the six RR patients, one relapse occurred during the pretreatment period, one in the treatment period, two in the post treatment period and none in the re-treatment period. No relapses occurred in SP patients. EDSS and 9 Hole Peg Test scores showed no significant changes during the study (Table 1).

TABLE 1

| | Clinical Measures | | | | | |
|---|---|---|---|---|---|---|
| | Pretreatment | | Estriol Treatment | | Post Treatment | |
| | 3 mo. | 6 mo. | 9 mo. | 12 mo. | 15 mo. | 18 mo. |
| | EDSS Scores | | | | | |
| 6 RR | 2.2 | 2.0 | 1.5 | 1.7 | 1.8 | 1.8 |
| | (0.6) | (0.5) | (0.7) | (0.6) | (0.6) | (0.5) |
| 4 SP | 5.0 | 5.0 | 4.9 | 5.0 | 5.1 | 5.0 |
| | (0.9) | (0.9) | (1.0) | (0.9) | (1.1) | (0.8) |
| | Hole Peg Test Score | | | | | |
| 4 RR | 22.2 | 21.8 | 22.5 | 21.5 | 21.0 | 21.4 |
| R | (2.4) | (1.6) | (2.3) | (1.9) | (1.7) | (2.4) |
| L | 24.8 | 22.9 | 24.3 | 23.3 | 23.0 | 22.7 |
| | (3.2) | (1.6) | (2.5) | (2.1) | (2.1) | (2.3) |
| 4 SP | 26.8 | 29.9 | 30.2 | 31.7 | 29.4 | 34.0 |
| R | (0.4) | (2.4) | (1.4) | (4.8) | (5.2) | (8.7) |
| L | 23.5 | 25.6 | 22.7 | 24.8 | 26.7 | 25.0 |
| | (1.4) | (2.5) | (1.7) | (2.6) | (0.7) | (1.8) |

Interestingly, PASAT cognitive testing scores were significantly improved in the RR-group, but not in the SP group (FIG. 4). This improvement in PASAT scores in RR patients by 14.0% during treatment as compared to baseline, reached statistical significance, P=0.04. It is unlikely that this improvement was entirely due to a practice effect of repeated testing because of the long time interval between testing (9 months) and because alternate versions of the test were used in each patient. This beneficial effect of estriol treatment on PASAT scores of RR MS patients is consistent with previous reports describing a beneficial effect of estrogen replacement therapy in surgically menopausal women and high dose estrogen treatment in Alzheimer's disease. Sicottte, et al. Treatment of Women with Multiple Sclerosis Using Pregnancy Hormone Estradiol: A Pilot Study. Neurology, 56 (8 Supp. 3):A75, April 2001, and Sicottte, et al. Treatment of Multiple Sclerosis with the Pregnancy Hormone Estradiol, Submitted to Neurology 2002, are herein incorporated by reference in their entirety.

Example 2

Progesterone in combination with estrogen treatments has been shown to protect against endometrial proliferation and cancer. Indeed, estrogen cannot be given for a lengthy period of time in an "unopposed" fashion in any woman with a uterus. Thus, seven of the 12 patients wanted to remain on estriol after completion of the 18 month study. These patients were then put back on 8 milligrams of estriol and 100 milligrams of progesterone per day. In an extension phase of the study which began after completion of the post treatment phase. This extension phase was 4 months in duration. Each of the seven patients had an MRI every month during the 4 month extension phase. Additionally, each of the seven patients was examined neurologically and had serologic studies done at the end of this phase. No known negative effects 100 milligrams of progesterone in combination therapy with 8 milligrams of estriol treatment were noted.

Example 3

In a pilot clinical trial, non-pregnant female MS patients were treated with estriol to induce a pregnancy level in serum. This treatment reduced the prototypic in vivo Th1 response, the delayed type hypersensitivity response, as well as reduced Th1 (TNFα, IFNγ) and increased TH2 (IL5, IL10) cytokine production by peripheral blood monuclear cells (Siotte et al., 2002; Soldan et al., 2003). Also, gadolinium-enhancing lesions on serial brain magnetic resonance images (MRIs) were reduced by >80% (Sicotte et al., 2002). Because enhancing lesion activity on brain MRI is a putative biomarker for relapses in MS, these reports together suggested that estriol treatment may recapitulate the anti-inflammatory effect of pregnancy in relapsing remitting MS (RRMS).

Example 4

A 33 year old white female patient was diagnosed as having relapsing remitting multiple sclerosis. Following the delivery of her first child (now age 7), the patient was treated only with Copaxone and relapsed at 6 weeks. Following the delivery of her second child (now age 3), the patient was again treated with Copaxone alone and again relapsed, this time at 4.5 months. Following a subsequent pregnancy, the patient was treated with 8 mg estriol/day in an attempt to prevent her post partum relapses.

Following the birth of the patient's third child (now 6 months), the patient resumed treatment with Copaxone as before. However, on day 10 post-partum she began taking estriol 8 mg/daily in an oral dosage form. The patient had no relapses for 6 months post-partum, and her neurologic exam is unchanged with minimal disability (EDSS=1). Since monthly brain MRIs with gadolinium to detect enhancing MS lesions are more sensitive for inflammatory disease activity than relapses, the patient underwent serial monthly MRIs at post partum months 4, 5, and 6. There was no enhancement at month 4, only one small enhancing lesion at month 5, and at 6 months only a small residual, less robust enhancement of the single lesion from the previous month. No new enhancement was observed at month 6. The T2 lesion load has been stable throughout.

The patient has had increased irregular menstrual bleeding despite using the progesterone minipill (norethindrone, 0.35 mg daily), one pill per day since day 10, to stabilize the uterine endometrium and for birth control. Uterine ultrasounds at month 3 and 6 showed a thin, not thick, endometrium, consistent with an unstable lining, not suggestive of hyperplasia. The patient doubled the progesterone minipill for 2 weeks to stabilize the endometrium. Otherwise no adverse events have been reported.

Example 5

Animals.

Female C57BL/6 mice, 8 weeks of age, were purchased from Taconic (Germantown, N.Y.). ERα KO mice backcrossed onto the C57BL/6 background for 16 generations were a generous gift from Dr. Dennis Lubahn (University of Missouri, Columbia, Mo.) (Lubahn et al., 1993). Wild-type littermates from F16 crosses served as ERα KO matched controls. ERβ KO mice, a generous gift from Dr. Jan Ake Gustafsson (Karolinska Institute, Stockholm, Sweden) (Krege et al., 1998), were backcrossed onto the C576BL/6 background for eight generations. Wild-type littermates from these crosses served as ERβ KO matched controls. Animals were housed under guidelines set by the National Institutes of Health, and experiments were conducted in accordance with the University of California, Los Angeles Chancellor's Animal Research Committee and the Public Health Service Policy on Humane Care and Use of Laboratory Animals.

Reagents.

PPT was purchased from Tocris Bioscience (Ellisville, Mo.), and E2 was purchased from Sigma-Aldrich (St. Louis, Mo.). Miglyol 812 N, a thin liquid oil, was obtained from Sasol North America (Houston, Tex.). Myelin oligodendrocyte glycoprotein (MOG) peptide, amino acids 35-55, was synthesized to >98% purity by Chiron Mimotopes (San Diego, Calif.).

EAE.

Active EAE induction ensued with subcutaneous injection of an emulsion containing the autoantigen MOG peptide, amino acids 33-55 (300 μg/mouse) and *Myobacterium tuberculosis* (500 μg/mouse) in complete Freund's adjuvant, as described previously (Suen et al., 1997; Liu et al., 2003). Mice underwent hormonal treatments as described below and were monitored daily for EAE disease severity using the standard EAE grading scale, as described previously (Pettinelli and McFarlin, 1981). Briefly, to determine the clinical score for each mouse on each day, each mouse was graded using the standard 0-5 scale: 0, unaffected; 1, tail limpness; 2, failure to right on attempt to roll over; 3, partial paralysis; 4, complete paralysis; and 5, moribund. On each day, the mean of the clinical scores of all mice within a given treatment group were determined, thereby yielding the mean clinical score for that treatment group. Some mice were followed clinically for up to 40 d after disease induction, and others were killed earlier for mechanistic studies, 1-2 d after the onset of clinical signs in the vehicle-treated group (day 16-19 after disease induction).

Treatments.

Isoflurane-anesthetized female mice were ovariectomized and allowed to recuperate for 10 days. Daily treatments of oil vehicle alone, estradiol, or PPT began 7 days before EAE immunization. Estradiol and PPT were dissolved in 10% ethanol and 90% oil to give the final proper concentration of 0.04 mg/kg/day of estradiol (Jansson et al., 1994) and 10 mg/kg/d of PPT per mouse (Harris et al., 2002). Estradiol, PPT or vehicle alone were given by daily subcutaneous injections along the midbackline and continued for the entire disease duration (up to 40 days after disease induction).

Perfusion.

Mice were deeply anesthetized with isoflurane and perfused transcardially with ice-cold 0.9% saline, followed by 10% formalin. Spinal cord columns were removed and postfixed overnight in 10% formalin and cryoprotected with 20% sucrose solution, in PBS. Spinal cords were removed from the column, cut in three parts (cervical, thoracic, and lumbar), and embedded in gelatin/sucrose mix. Spinal cord regions in gelatin were further postfixed and stored in 20% sucrose. Free-floating sections (25 μm thick) were cut coronally with a sliding microtome and collected serially in PBS.

Uterine Weights.

After the mice were killed, each uterus was extracted, and the fat, connective tissue, and excess fluid were removed to obtain each uterine weight, as described previously (Frasor et al., 2003).

Immune Responses.

Spleens were harvested during deep anesthesia before perfusion. Splenocytes were stimulated with the autoantigen, MOG peptide 35-55, at 25 μg/ml. Supernatants were collected after 48 and 72 h, and levels of TNFα, interferon-γ (IFNγ) interleukin-6 (IL6), and IL5 were determined by cytometic bead array (BD Biosciences Pharmingen, San Diego, Calif.) as described previously (Liu et al., 2003).

Histopathology and Immunohistochemistry.

Serial sections ere mounted on slides and stained with hematoxylin and eosin (H&E), Nissl, or Luxol fast blue (LFB)-cresyl violet. Consecutive sections were also examined by immunohistochemistry. Briefly, 25 μm free-floating sections were permeabillized in 0.3% Triton X-100 in PBS and blocked with 10% normal goat serum. White matter immunostaining was enhanced by treating sections with 95% ethanol/5% acetic acid for 15 min before permeabilization and blocking. To detect specific cell types and structures, sections were preincubated with primary antibodies in PBS solution containing 2% NGS for 2 h at room temperature, and then overnight at 40° C. The following primary antibodies were used: anti-03 tubulin and anti-neurofilament-NF200 [monoclonal (Chemicon, Temecula, Calif.); polyclonal (Sigma Biochemical)], anti-neuronal-specific nuclear protein (NeuN), anti-CD45 (Chemicon), anti-myelin basic proteins (MBP; Chemicon) and anti-Mac 3 (BD Biosciences Pharmingen). The second antibody step was performed by labeling with antibodies conjugated to TR1TC, FITC, and Cy5 (Vector Laboratories and Chemicon). IgG control experiments were performed for all primary antibodies, and no staining was observed under these conditions. To assess the number of cells, a nuclear stairs 4', 6'-diamidino-2-phenylindole dihydrochloride (DAPI; 2 ng/ml; Invitrogen, Eugene, Oreg.) was added for 15 min before final washes after secondary antibody addition. The sections were mounted on slides, dried, and coverslipped in fluoromount G (Fisher Scientific, Hampton, N.H.).

Microscopy.

Stained sections were examined and photographed using a confocal microscope (TCS-SP; Leica, Mannheim, Germany) or a fluorescence microscope (BX51WI; Olympus, Tokyo, Japan) equipped with Plan Fluor objectives connected to a camera (DP7O; Olympus). Digital images were collected and analyzed using Leica confocal and DP7O camera software. Images were assembled using Adobe Photoshop (Adobe Systems, San lose, CA).

Quantification.

To quantify immunostaining results, sections from spinal cord levels T1-T5 were examined, six from each mouse, with n=3 mice per treatment group, for a total of 18 sections per treatment group. Images were captured under microscope (4×, 10×, or 40×) using the DP7O Image software and a DP70 camera (both from Olympus). Identical light intensity and exposure times were applied to all photographs from each experimental set. Images from the same areas of spinal cord were compared (T1-T5) and were acquired separately from delineated whole gray and white matter regions. The middle region of the ventral horn was the focus for gray matter analysis, whereas the area lateral to the ventral horn was the focus for white matter analysis. Six gray matter and six white matter pictures were collected from the two sides of T1-T5 sections (100 μm apart) from three animals in each treatment group. All images were converted to grayscale and then analyzed by density measurement with ImageJ version 1.29 (the Windows version of NIH Image), downloaded from rsb.info.nih.gov/ij. A fixed threshold range of 0-160 was chosen to highlight the staining signals in normal spinal cord sections, and the total area within this range was measured, averaged, and compared.

Increase in total number of infiltrating cells after induction of EAE was measured by density measurements of DAPI+nuclei in the whole white matter. Neuronal cells were quantified by counting the NeuN+/β3-tubulin+/DAPI+ cells per square millimeter in the whole gray matter. Both white and gray matter assessments occurred its the T1-T5 spinal cord sections. Laser-scanning confocal microscopic scans at 40× were performed on Mac 3+/β3-tubulin+ immunostained spinal cord sections corresponding to levels T1-T5 ventral horn. The results for each experimental condition were averaged from four unilateral levels per mouse (100 μm apart, three mice in each treatment group, total of 12 sections per treatment group) and were expressed as mean fold change compared with healthy match controls.

Statistical analysis. EAE disease severity was compared between groups using the Friedman test, histopathological changes were assessed using 1×4 ANOVAs, and uterine weights and cytokine levels were compared between treatment groups using Student's t test, as described previously (Dalal et al., 1997).

Results.

Treatment with an ERα ligand remains highly selective for ERα in vivo during EAE.

The dose of the ERα-selective ligand for use in our RAE experiments which could induce a known biological response on a control tissue (the uterus). Estrogen-induced increases in uterine weight had been shown previously to be mediated by ERα, and doses of the ERα ligand PPT needed for this in vivo treatment effect had been described (Frasor et al., 2003). Daily subcutaneous injections of PPT, at a dose previously shown to increase uterine weight (10 mg/kg/d), resulted in a significant increase in uterine weight in female C57BL/6 mice with EAE at day 40 after disease induction, FIG. 1A. Sensitivity of this technique was shown by the decrease in uterine weight in ovariectomized compared with sham-operated, vehicle-treated mice. Treatment with injections of high doses of estradiol (to induce pregnancy levels in serum) served as a positive control, whereas treatment with injections of vehicle alone served as a negative control. To further demonstrate the in vivo selectivity of this dose of PPT, uterotrophic responses were also examined during PPT treatment of ERα or ERβ knock-out mice. Significant increases in uterine weight were observed in PPT-treated ERβ knock-out mice (FIG. 1B) but not in ERα knock-out mice (FIG. 1C). Together, these data demonstrated that the method of administration of the ERα ligand PPT induced an expected biological response in vivo on a positive control tissue.

FIG. 5 depicts results showing results showing treatment with an ERα-selective ligand is highly selective in vivo during EAE. As shown in FIG. 5A, treatment with the ERα ligand PPT induced expected biological responses on uterine weight (y-axis=uterine weight in grams). Uterine weight was increased with PPT given as daily subcutaneous injections at 10 mg/kg/day. The decrease in uterine weight with ovariectomy compared with sham surgery demonstrated the sensitivity of the technique in detecting differences in uterine weights associated with differences in estrogen levels. Treatment with a dose of estradiol known to induce a late pregnancy level of estradiol was used ad a positive control for an increase in uterine weight, whereas treatment with vehicle alone served as the negative control. The uteri were removed at day 35-40 during EAE treatment with the indicated hormone (sham vehicle, n=6; OVX vehicle, n=12; OVX estradiol, n=18; OVX PPT, n=18). OVX PPT and OVX Estradiol, each as compared with OVX Vehicle, *p<0.0001. WT<Wild type. As shown in FIG. 5B, Uterine weights were examined in ovariectomized ERβ knock-out mice as in FIG. 5A. Uterine weights were increased with PPT treatment in ERβ knock-out mice (OVX vehicle, n=9; OVX estradiol, n=12; OVX PPT, n=12). OVX PPT and OVX Estradiol, each as compared with OVX Vehicle, * p<0.0001. As shown in FIG. 5C, Uterine weights were examined in ovariectomized ERα knock-out mice as in FIG.

5A. Uterine weights were not increased with PPT treatment in ERα knock-out mice (OVX vehicle, n=6; OVX estradiol, n=4; OVX PPT, n=6).

Treatment with an ERα Ligand Reduces the Clinical Severity of EAE.

Figure 6A:
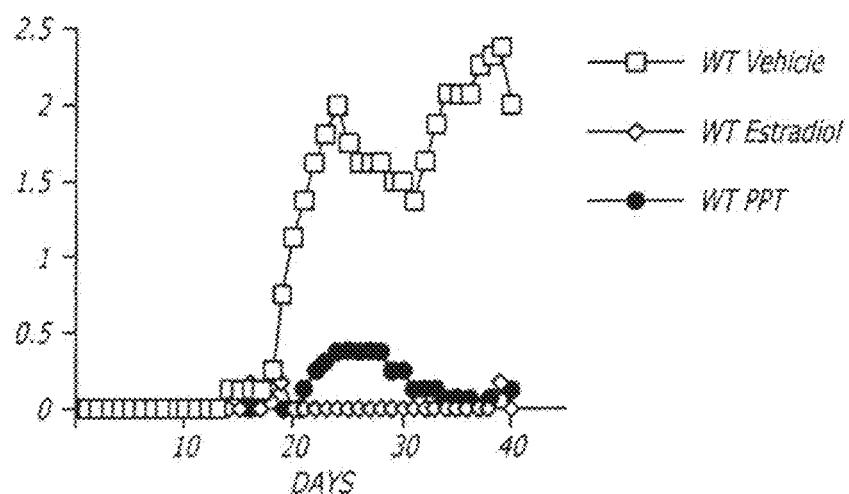
FIGS. 6A-C are graphs showing the effect of ER alpha selective ligand on clinical scores in wild type (WT), ER beta knock-out (KO), or ER alpha KO in mice treated with a control (vehicle), estrogen receptor alpha ligand (PPT) or estradiol treated animals.

Using the above dose and method of administration, PPT treatment was assessed for its effect on the clinical course of EAE. Ovariectomized, C57BL/6 wild-type female mice with MOG 35-55 peptide-induced active EAE were treated with the ERα-selective ligand PPT. PPT treatment significantly reduced the clinical severity of EAE (FIG. 6A). Treatment with injections of estradiol served as a positive control, whereas treatment with injections of vehicle alone served as the negative control.

Figure 6B:
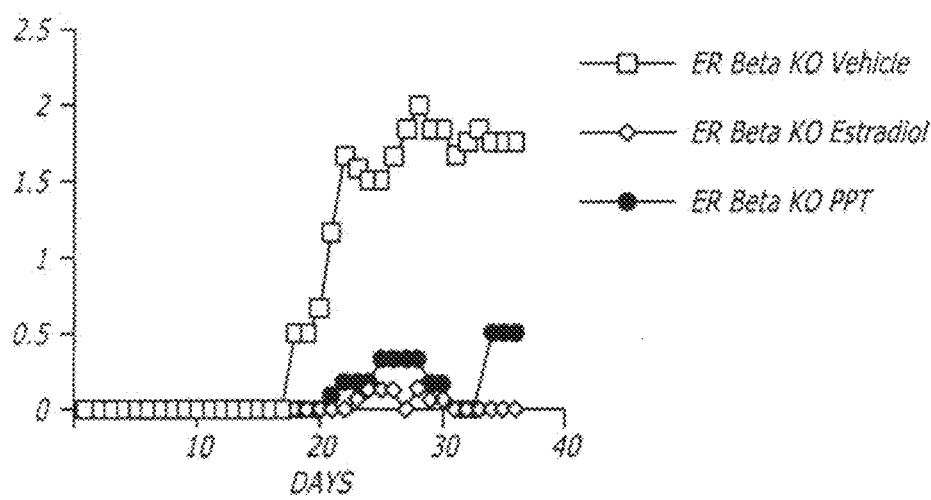
Figure 6C:
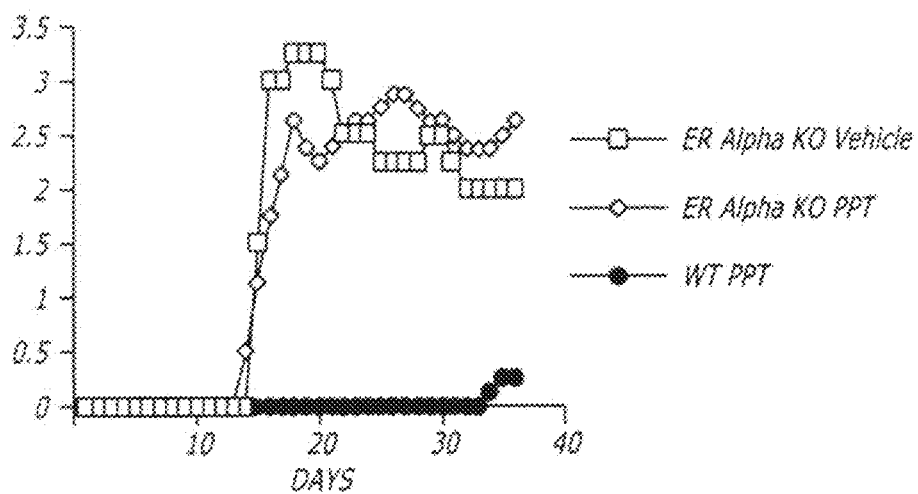

When ovariectomized ERβ knock-out C57BL/6 female mice were treated with PPT-during active EAE, clinical disease severity was also significantly decreased (FIG. 6). These data demonstrated that the presence of ERβ was not required for disease protection mediated by treatment with PPT. In contrast, when PPT was administered to ovariectomized ERα knock-out mice induced with active EAE, the disease-ameliorating effect of PPT treatment was abolished, as evidenced by the lack of a difference in mean clinical scores when comparing PPT-treated and vehicle-treated ERα knock-out mice (FIG. 6C). Similar results were obtained when castrated male mice were used instead of ovariectomized females (data not shown), consistent with a previous publication demonstrating that estrogen-medicated improvements in clinical EAE in castrated male mice were abrogated in the ERα knock-out (Liu et al., 2003). ERα knock-out female mice have high circulating estradiol levels; hence, estrogen unresponsiveness in this mouse could be attributable to the ERα genetic modification or the estrogen history of the mouse before ovariectomy at 4 weeks. Because male ERα knock-out mice do not have high circulating levels of estradiol, similar results in both the female and male ERα knock-outs make the ERα genetic modifications, not the estrogen history of the mouse, most likely responsible for effects observed.

These data demonstrated that the estrogen-medicated protection from EAE could be recapitulated by treatment with a highly selective ERα ligand, and that this protection was not dependent on an interaction with ERβ.

FIG. 6. Treatment with an ERα-selective ligand is sufficient to reduce the clinical severity of EAE. As shown in FIG. 6A, EAE clinical severity was decreased in ovariectomized, wild-type (WT) C57BL/6 female mice treated with PPT. Daily treatments of ovariectomized mice with injections of vehicle (negative control), estradiol (positive control), or PPT (10 mg/kg/day) began, and then 7 d later, active EAE was induced with MOG 35-55 peptide. Mean clinical scores were significantly reduced in both estradiol- and PPT-treated mice compared with vehicle treated (p<0.0001, Friedman test). Data are representative from experiments repeated a total of five times. As shown in FIG. 6B, the decrease in the mean clinical scores of EAE by PPT treatment was not dependent on the presence of ERβ. Ovariectomized, ERβ knock-out C57BL/6 female mice were treated with either PPT, estradiol, or vehicle as in A. Mean clinical scores were significantly reduced in both estradiol- and PPT-treated mice compared with vehicle treated (p<0.0001, Friedman test). Data are representative from experiments repeated a total of three times. As shown in FIG. 6C, PPT treatment in vivo during EAE remains highly selective for ERα. Ovariectomized female ERα knock-out C57BL/6 mice were treated as in FIG. 6A. In ERα knock-out mice, mean clinical scores were not significantly different in PPT-treated compared with vehicle-treated. PPT-treated wild-type mice served as a positive control for a PPT treatment effect within the experiment. Data are representative from experiments repeated a total of three times. Error bars indicate variability of clinical scores between mice within a given treatment group. n=5 mice per each treatment group.

Treatment with an ERα Ligand Reduces Autoantigen-Specific Proinflammatory Cytokine Production.

Because it had been shown previously using ERα knock-out mice that both disease protection and a reduction in proinflammatory cytokines (TNFα and IFNγ) were dependent on ERα, we next determined whether treatment with an ERα ligand could reduce proinflammatory cytokine production. As demonstrated in FIG. 7, PPT treatment significantly reduce TNFα, IFNγ, and IL6 production. Interestingly, we had shown previously that production of the Th2 cytokine IL5 was increased with estrogen treatment and that this was only partially, but not completely, abolished in the ERα knock-out (Liu et al., 2003). In the present study, when wild-type mice were treated with the ERα agonist PPT, treatment significantly increased IL5 production. Together, these data demonstrated that treatment with an ERα agonist induced changes in cytokine production during autoantigen-specific immune responses in the peripheral immune system that would be anti-inflammatory with respect to EAE immunopathogenesis.

Figures 7A, 7B:
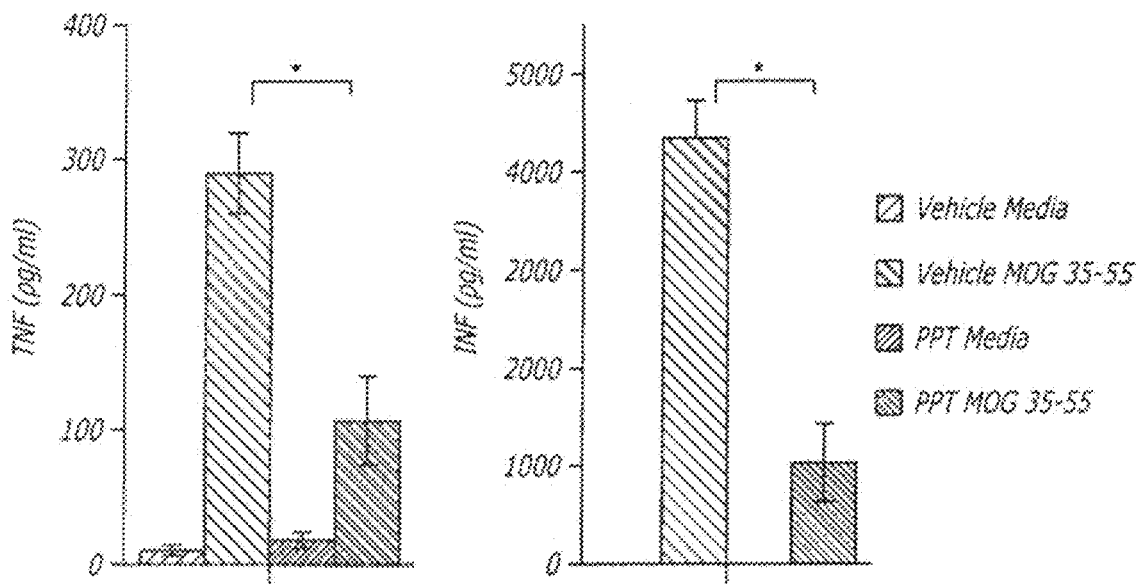
FIGS. 7A-D are bar graphs showing proinflammatory cytokine production by peripheral immune cells in ovariectomized, wild type (WT) C57BL/6 female mice with EAE.
Figures 7C, 7D:
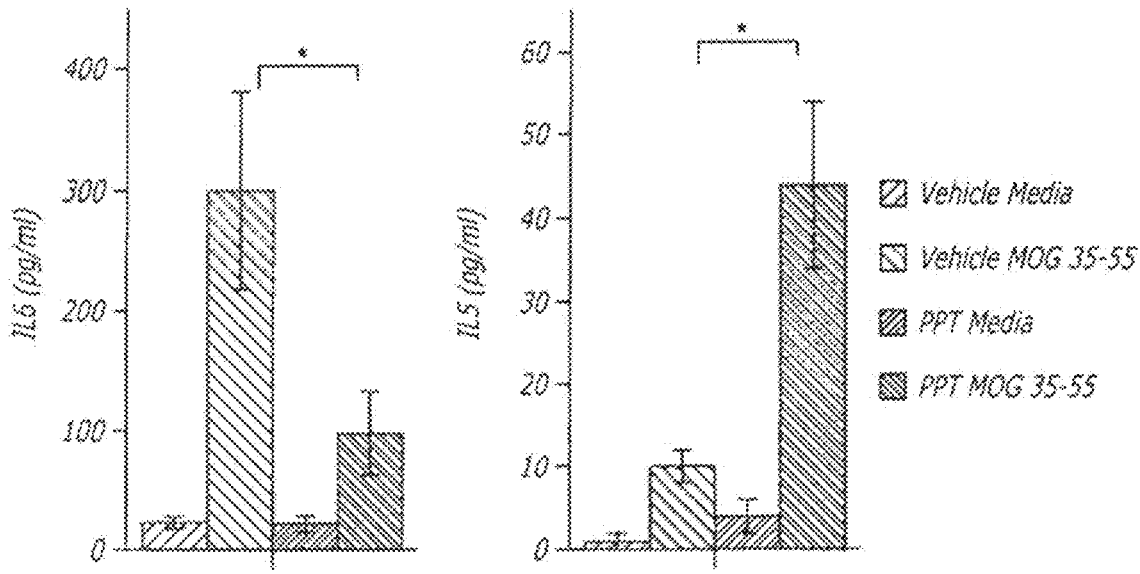

As shown in FIG. 7, treatment Treatment with an ERα ligand reduced proinflammatory cytokine production by peripheral immune cells in ovariectomized, wild-type C57BL/6 female mice with EAE. EAE was induced as in FIG. 6, and then at day 40 after disease induction, mice were killed, and cytokine production by MOG 35-55 stimulated splenocytes was determined. TNFα, IFNγ, and IL6 levels were each significantly reduced with PPT treatment, whereas IL5 levels were increased with PPT treatment. Error bars indicate variability of cytokine values for splenocytes between individual mice within a given treatment group, with n=5 mice for each treatment group. Data are representative of experiments repeated three times. *p<0.05.

Treatment with an ERα Ligand Reduces Inflammation and Demyelination in EAE.

Because we had observed that treatment with the ERα ligand PPT recapitulated the protective effect of estrogen treatment on the clinical course of EAE and was anti-inflammatory with respect to the autoantigen-specific immune response in the periphery, we next ascertained the effect of treatment with PPT on inflammation and demyelination in the CNS of EAE mice. Spinal cord sections of ovariectomized, C57BL/6 mice at the acute phase of EAE (1-2 days after onset of clinical signs in vehicle-treated mice) were assessed for inflammation and demyelination. Mice from all treatment groups were killed at the same time point, to permit their examination in parallel. Compared with vehicle-treated EAE, both inflammation and demyelination were markedly reduced by treatment with the ERα ligand PPT or E2 (FIG. 4). H&E-stained vehicle-treated EAE mice, compared with normal healthy controls, had numerous multifocal to coalescing inflammatory cell infiltrates in the spinal cord. Infiltrates were present in the leptomeninges, around blood vessels in the leptomeninges, and in the parenchyma of the white matter (FIG. 4A). Inflammatory cell infiltrates were associated with pallor and vacuolation, consistent with demyelination. Quantification of white matter cell density by counting DAPI+ cells revealed a 60% increase in infiltrates of vehicle-treated EAE group. In contrast, both estradiol and PPT treated mice had no detectable inflammation, with white matter cell densities similar to those in the normal control (FIG. 4D).

The degree of myelin loss was assed by Luxol fast blue and confirmed by MBP immunostaining. Luxol fast blue staining revealed demyelination at the sites of inflammatory cell infiltrates (FIG. 4B). Also, myelin staining of dorsal column regions of vehicle-treated spinal cord section had significantly less MBP immunostaining compared with normal control, E2-, and PPT-treated sections, FIG. 4C. Quantification of demyelination by density analysis of Luxol fast blue-stained spinal cord sections revealed a 25% decrease in myelin density in vehicle-treated EAE mice. In contrast, both estradiol- and PPT-treated mice had much less demyelination, with myelin densities not significantly different from those in the normal control (FIG. 8E).

As shown in FIG. 8, treatment with an ERα ligand reduced inflammation and demyelination in spinal cords of mice with EAE. In FIG. 8A, representative H&E-stained thoracic spinal cord sections (4× magnification) from normal (healthy control), as well as vehicle-, E2-, and PPT-treated EAE mice are shown. Vehicle-treated EAE mouse spinal cord shows multifocal to coalescing areas of inflammation in the leptomeninges and white matter, around blood vessels, and in the parenchyma of the white matter (areas of inflammation shown byarrows). No inflammation was observed in either E2- or PPT-treated EAE spinal cords. As shown in FIG. 8B, luxol fast blue-stained region of dorsal column (square in A) of spinal cords (40× magnification). Intense demyelination in the white matter is seen in vehicle-treated EAE sections only. As shown in FIG. 8C, anti-MBP immunostained dorsal column demonstrated demyelination in the white matter of vehicle-treated EAE sections only. As shown in FIG. 8D, increase in total number of infiltrating cells after induction of EAE was semiquantified by counting DAPI+ cells in the entire delineated white matter (including dorsal, lateral, and ventral funiculi) and presented as percentage of normal. Vehicle-treated EAE mice had a significant increase in white matter cell density compared with healthy normal control, whereas E2-treated and the ERα ligand (PPT)-treated groups did not. As shown in FIG. 8E, the extent of demyelination was compared by staining thoracic spinal cord sections with Luxol fast blue. Myelin density is presented as percentage of normal. Vehicle-treated mice EAE mice had a significant decrease in myelin density in the entire delineated white matter as compared with normal control, whereas E2-treated and PPT-treated groups did not. Number of mice, three per treatment group; number of T1-T5 sections per mouse, six; total number of sections per treatment group, 18. **Statistically significant compared with normals ($p<0.001$), 1×4 ANOVAs. Data are representative of experiments repeated in their entirety on another set of EAE mice with each of the treatments.

Treatment with an ERα Ligand is Neuroprotective in EAE.

Figure 9A:
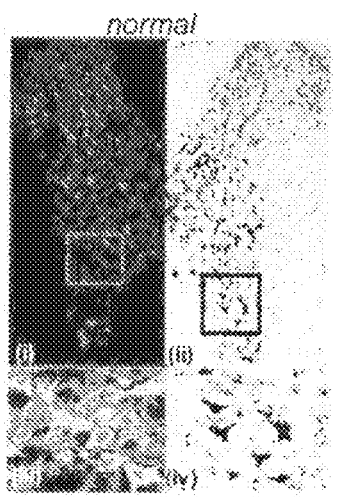
FIGS. 9A-E depict various measures of estrogen receptor alpha ligand reduced inflammation and demyelination in spinal cords of mice with EAE.
Figure 9B:
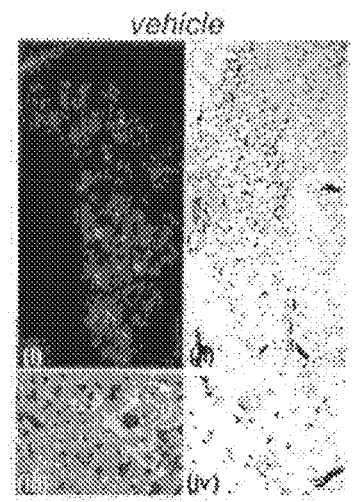
Figure 9C:
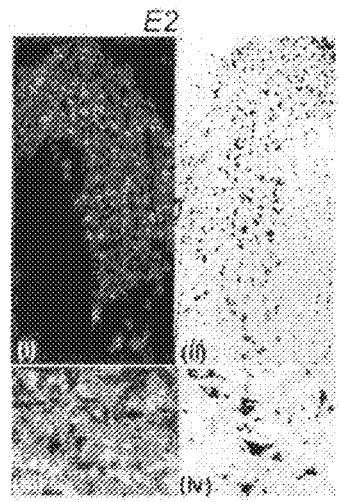
Figure 9D:
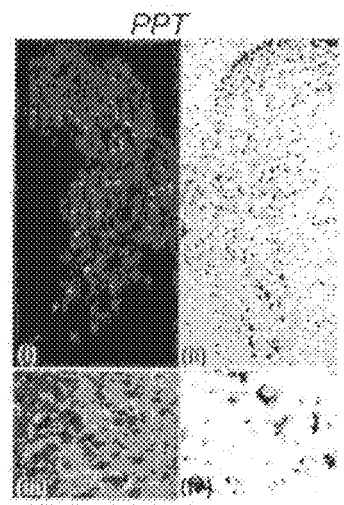
Figure 9E:
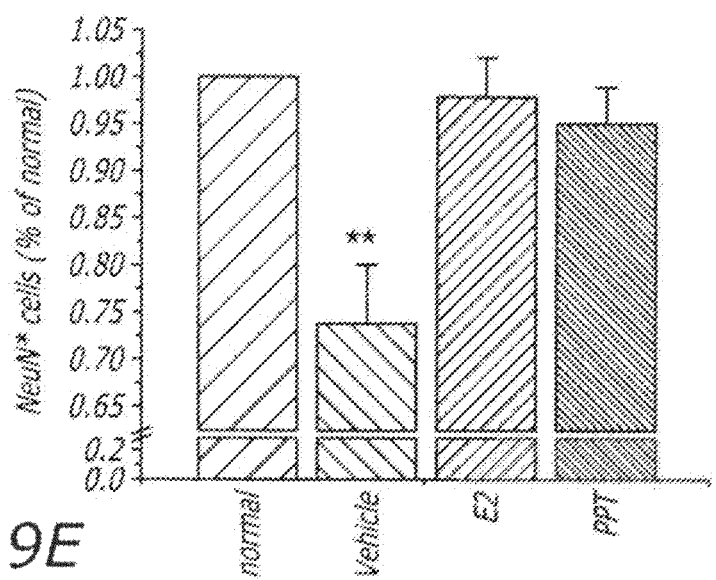

In light of the significant anti-inflammatory effect induced by PPT treatment of mice with EAE, the preservation of neuronal and axonal integrity was examined. A combination of Nissl stain histology and anti-NeuN/β3-tubulin immunolabeling was used to identify and semiquantify neurons, and neurofilament antibody (anti-NF200) was used to identify axons. At the acute phase of EAE, 1-2 d after the onset of clinical signs in vehicle-treated mice, thoracic spinal cord sections of all treatment groups of EAE mice were assessed for NeuN+/β3 tubulin+ neurons in the gray matter and NF200 axons in the white matter. A surprising decrease in neuronal staining (NeuN+I/Nissl+) in gray matter occurred at this early time point in vehicle-treated EAE mice (FIG. 9B) compared with normal, healthy, age- and gender-matched control mice (FIG. 9B). This significant decrease in neuronal staining in gray matter of vehicle-treated EAE mice was not observed in EAE mice treated with either estradiol (FIG. 9C) or the ERα ligand (FIG. 9D). Quantification of NeuN+ cells in gray matter confirmed the significant loss in vehicle-treated EAE mice compared with normal controls, whereas estradiol- and PPT-treated mice had NeuN+cell numbers that were no different from the normal control (FIG. 9E).

As shown in FIG. 9, treatment with an ERα ligand preserved neuronal staining in gray matter of spinal cords of mice with EAE. As shown in FIGS. 9A-D, split images of thoracic spinal cord sections stained with NeuN (red) in I and Nissl in ii at 4× magnification, derived from normal healthy control mice (A), vehicle-treated EAE (B), E2-treated EAE mice (C), and ERα ligand (PPT)-treated EAE mice (D), each killed very early during EAE, 1-2 days after the onset of clinical signs. iii, Merged confocal scan at 40× of NeuN+ (red) and β3-tubulin+(green) colabeled neurons from an area represented by dotted white square area in i. iv, A40× magnification of Nissl-stained area in solid black square in ii. A decrease in NeuN+ immunostaining and Nissl staining was observed in the dorsal horn, intermediate zone, and ventral horn of vehicle-treated EAE mice (FIG. 9B) compared with normal controls (FIG. 9A). White arrows in Biii denote loss of NeuN+ staining. In contrast, EAE mice treated with either estradiol (FIG. 9C) or PPT (FIG. 9D) had preserved NeuN and Nissl staining. After quantification of neurons in the entire delineated gray matter of T1-T5 sections, NeuN+ immunolabeled neurons were significantly decreased, by nearly 25%, in vehicle-treated EAE mice compared with normal controls, but E2- and PPT-treated EAE mice were not statistically different from normal controls (FIG. 9E). Number of mice, three per treatment group; number of T1-T5 sections per mouse, six; total number of sections per treatment group, 18. **Statistically significant compared with normals ($p<0.001$); 1×4 ANOVAs. Data are representative of experiments repeated in their entirety on another set of EAE mice with each of the treatments.

Immunostaining for neurofilament (NF200) resulted in clear identification of axons within the spinal cord of normal mice (FIG. 10A). A significant decrease in axonal NF200 staining (NF200+) in white matter occurred in vehicle-treated EAE mice compared with normal controls in areas positive for CD45 staining, consistent with previous observations of axonal transection within inflammatory white matter lesions in EAE (Wujek et al., 2002). EAE mice treated with either estradiol or the ERα ligand demonstrated not decrease in axonal NF200+ staining and only an occasional single cell positive for CD 45 (FIG. 10A). Quantification of axon numbers in white matter confirmed the significant loss in vehicle-treated EAE mice, but no significant axonal loss occurred in EAE mice treated with either estradiol or the ERα ligand (FIG. 10C). These immunohistoligical data are consistent with our observation of markedly reduced inflammatory lesions by H&E in white matter with these treatments (FIG. 8A). Notably, at this early time point in EAE, there was no loss in axon numbers in white matter areas devoid of inflammatory lesions, even in the vehicle-treated EAE group, thereby providing no evidence for Wallerian degeneration of white matter tracts in these regions of the cord at this very early time point in EAE.

Treatment with an ERα Ligand Reduces Microglial/Monocyte Activation in White and Gray Matter of Mice with EAE.

Gray matter axonal pathology has been described in cortex of MS patients, which was characterized by activated microglia closely opposed to and ensheathing apical dendrites, neurites, and neuronal perikarya (Peterson et al., 2001). In light of our observation of a decrease in NeuN+/β3-tubulin+/Nissl+ neuronal staining in the gray matter of spinal cords in EAE, we next addressed the microglial reaction in this gray matter. Microglia/monocytes were stained for Mac 3, a lysosomal antigen equivalent to LAMP-2 (lysosomal-associated membrane protein 2)/CD 107b, present on the surface of microglia and mature mononuclear phagocytes, and sections were coimmunolabeled with anti-B3-tubulin (FIG. 10B). Striking Mac 3+ reactivity was observed in gray matter of mice at this very early time point in EAE, only 1-2 days after the onset of clinical signs in the vehicle-treated group. Most of the MAC 3+ cells demonstrated a morphology similar to that of activated microglia (FIG. 10B, inset). They were in close vicinity to, and in direct contact with, gray matter neurons that had reduced and punctuate β3-tubulin staining (FIG. 10B). In contrast, EAE mice treated with either the ERα ligand PPT, or estradiol, which were killed and examined in parallel, had some, but significantly less, immunoreactivity (FIG. 10B). Quantification of MAC 3+ cells revealed an ~65% decrease when E2- and PPT-treated spinal cords were compared with those from vehicle-treated EAE mice (FIG. 10D).

As shown in FIG. 10, treatment with an ERα ligand reduced CD45+ and Mac 3+ cells in white and gray matter of mice with EAE. As shown in FIG. 10A, thoracic spinal cord sections from mice used in FIG. 9 were coimmunostained with NF200 (green) and CD45 (red) at 10× magnification. Shown are partial images with white and gray matter from normal control, vehicle-treated EAE, E2-treated EAE, or ERα ligand (PPT)-treated EAE mice. LF, Lateral *funiculus* of white matter; GM, gray matter. The vehicle-treated EAE cords had large areas of CD45+ cells associated with reduced NF200 axonal staining in white matter compared with the normal control, whereas estradiol and ERα ligand-treated EAE mice had only occasional CD45 positivity, with intact NF200 axonal staining. As shown in FIG. 10B, consecutive sections from the same mice were also coimmunostained with β3-tubulin (green) and Mac 3(red), with the section of the ventral horn designated by the dotted line square area in FIG. 10A scanned at 40× magnification by confocal microscopy. Vehicle-treated EAE mice demonstrated markedly increased Mac 3 staining in ventral horn gray matter compared with normal control mice, with most of these Mac 3+ cells having the morphology of microglia (inset, 100× magnification). They were surrounding neuronal structures (white arrows). In contrast, E2- and ERα ligand (PPT)-treated EAE cord sections demonstrated less Mac 3 immunostaining compared with vehicle-treated EAE mice. As shown in FIG. 10C, after quantification, neurofilament-stained axon numbers in white matter were significantly lower in vehicle-treated EAE mice compared with normal mice, whereas E2- and PPT-treated EAE mice demonstrated no significant reduction in axon numbers. Axon number is presented as percentage of normal. Statistically significant compared with normal ($p<0.001$); 1×4 ANOVAs. FIG. 10D, Mac 3× cells were analyzed by density measurements and represented as percentage of vehicle-treated groups. Compared with vehicle-treated EAE mice, both the E2-treated and PPT-treated had significantly lower Mac 3+ immunoreactivity in gray matter. Number of mice, three per treatment group; number of T1-T5 sections per mouse, four; total number of sections per treatment group, 12. Statistically significant compared with normal ($p<0.001$); 1×4 ANOVAs. Data are representative of experiments repeated in their entirety on another set of EAE mice with each of the treatments.

Example 6. The Neuroprotective Effects of Estrogen Receptor (ER) Beta

Methods. Animals.

Female wild type C57BL/6 mice, as well as female ERJ3 1(0 mice on the C57BL16 background, age 8 weeks, were obtained from 'laconic (Germantown, N.Y.). Wild type SI1L female mice, age S weeks, were obtained from Harlan laboratories (Indianapolis, Ind.). Animals were maintained in accordance with guidelines set by the National Institutes of Health and as mandated by the University of California Los Angeles Office for the Protection of Research Subjects and the Chancellor's Animal Research Committee.

Reagents.

Propyl pyrazole triol (PPt and Diarylpropionitrile (DPN), an ERα and an ERI3 agonist, respectively, were purchased from Tocris Bioscience (Ellisville, Mo.). Estradiol was purchased from Sigma-Aldrich (St. Louis, Mo.). Miglyol 812 N, a thin liquid oil, was obtained from Sasol North America (Houston, Tex.). Myelin oligodendrocytes glycoprotein (MOO) peptide, amino acids 35-55, proteolipid protein (PLP) peptides 139-151 and 179-191, and myelin basic protein (MBP) peptide 83-102 were synthesized to >98% purity by Mimotopes (Clayton, Victoria, Australia).

Uterine Weights to Assess Dosing.

Uterine weight was used as a positive control to assess dosing of estrogen agonists. Daily subcutaneous injections of vehicle, estradiol, PPT, or DPN, as well as a combination of ITT with DPN, were administered for ten days at indicated doses to ovariectomized mice. Following euthanasia, the uterus was extracted, then fat, connective tissue, and excess fluid removed in order to obtain the uterine weight, as described.

Hormone Manipulations During EAE.

Isotlurane-anesthetized female mice were ovariectomized and allowed to recuperate for 7-10 days. Daily subcutaneous injections of vehicle, estradiol, PPT, or DPN began seven days prior to EAE immunization, and continued throughout the entire disease duration. Estradiol was delivered at a concentration of 0.04 mg/kg/day, DPN at 8 mg/kg/day and ITT at 10 mg/kg/day. Vehicle alone treatments consisted of 10% Ethanol and 90% Migylol.

EAE Induction.

Active EkE was induced by immunizing with 300 gg of myelin oligodenrocyte glycoprotein (MOO) peptide, amino acids 35-55, and 500 pg of *Mycobacterium tuberculosis* in complete Freund's adjuvant as described. Active EAE was induced in SiT, mice with 100 jig of proteolipid protein (PLP) peptide, amino acids 139-15 1, and 100 jig of *Mycobacterium tuberculosis* in complete Freund's adjuvant as described. Mice were monitored and scored daily for clinical disease severity according to the standard 0-5 EAE grading scale: 0, unaffected; 1, tail limpness; 2, failure to right upon attempt to roll over; 3, partial paralysis; 4, complete paralysis; and 5, moribund. On each day, the mean of the clinical scores of all mice within a given treatment group were determined, thereby yielding the mean clinical score for that treatment group. Some mice were followed clinically for up to 50 days after disease induction, while others were sacrificed earlier for mechanistic studies at day 19 after disease induction, corresponding to day 4-6 after the onset of clinical signs in the vehicle treated group.

Rotarod Testing.

Motor behavior was tested up to two times per week for each mouse using a rotarod apparatus (Med Associates mc, St. Albans, Vt.). Briefly, animals were placed on a rotating horizontal cylinder for a maximum of 200 seconds. The amount of time the mouse remained walking on the cylinder, without falling, was recorded. Each mouse was tested on a speed of 3-30 rpm and given three trials for any given day. The three trials were averaged to report a single value for an individual mouse, and then averages were calculated for all animals within a given treatment group. The first two trial days, prior to immunization (day 0), served as practice trials.

Immune Responses.

Spleens were harvested either after deep anesthesia prior to perfusion or after euthanasia. Splenocytes were stimulated with the indicated autoantigens at 25 pg/ml, and proliferation assessed using standard H3 incorporation assays, as described. Supernatants were collected after 48 and 72 hours, and levels of TNF-i, IFN-γ, 11,6, and 1 L5 were determined by cytometric bead array (BD Biosciences), as described.

Perfusion.

Mice were deeply anesthetized with isoflurane and perfused transcardially with ice-cold 0.9% saline, followed by 10% formalin. Spinal cord columns were removed and post-fixed overnight in 10% formalin and cryoprotected with 20% sucrose solution in PBS. Spinal cords were removed from the column and cut in 3 parts (cervical, thoracic and lumbar) and embedded in gelatin/sucrose mix. Spinal cord regions in gelatin were further postfixed and stored in 20% sucrose. Free-floating sections (25 µm thick) were cut coronally with a sliding microtome and collected serially in PBS.

Histopathology and Immunohistochemistry.

Serial sections were mounted on slides and stained with Hematoxylin & eosin (H&E) or Nissl. Consecutive sections were also examined by immunohistochemistry. Briefly, 25 µm free-floating sections were permeabilized in 0.3% Triton X-100 in PBS and blocked with 10% normal goat serum. White matter immunostaining was enhanced by treating sections with 95% ethanol/5% acetic acid for 15 minutes prior to permeabilization and blocking. To detect specific cell types and structures, sections were pre-incubated with primary antibodies in PBS solution containing 2% NGS for 2 hours at room temperature, then overnight at 40 C. The following primary antibodies were used: anti-133 tubulin and anti-neurofilament-NF200 (monoclonal, Chemicon; polyclonal Sigma Biochemical), anti-neuronal specific nuclear protein (NeuN), anti-CD4S (Chemicon), and anti-MW (Chemicon). The second antibody step was performed by labeling with antibodies conjugated to TRITC, FITC and Cy5 (Vector Labs and Chemicon). IgG-control experiments were performed for all primary antibodies, and no staining was observed under these conditions. To assess the number of cells, a nuclear stain 4',6-Diamidino-2-phenylindole, DAPI (2 ng/ml; Molecular Probes) was added for 15 minutes prior to final washes after secondary antibody addition. The sections were mounted on slides, dried and coverslipped in fluoromount G (Fisher Scientific).

Microscopy.

Stained sections were examined and photographed using a confocal microscope (Leica TCS-SP, Mannheim, Germany) or a fluorescence microscope (BX51WI; Olympus, Tokyo, Japan) equipped with Plan Fluor objectives connected to a camera (DP70, Olympus). Digital images were collected and analyzed using Leica confocal and DP70 camera software. Images were assembled using Adobe Photoshop (Adobe Systems, San Jose, Calif.).

Quantification.

To quantify immunostaining results, sections from spinal cord levels T1-T5 were examined, six from each mouse, with n=3 mice per treatment group, for a total of 18 sections per treatment group. Images were captured under microscope (4×, 10× or 40×) using the DP70 Image software and a DP70 camera (both from Olympus). Identical tight intensity and exposure times were applied to all photographs from each experimental set. Images from the same areas of spinal cord were compared (TI-IS) and were acquired separately from delineated whole gray and white mailer regions. The middle region of the ventral horn was the focus for gray matter analysis, while the area lateral to the ventral horn was the focus for white matter analysis. Six gray matter and six white matter pictures were collected from the two sides of TI-IS sections (100 jim apart) from three animals in each treatment group. All images were converted to grayscale and then analyzed by density measurement with ImageJ vi 0.29 (the Windows version of NIH Image), downloaded from rsb.info.nih.gov/ij. A fixed threshold range of 0 to 160 was chosen to highlight the staining signals in normal spinal cord sections, and the total area within this range was measured, averaged, and compared.

Increase in total number of infiltrating cells after induction of EAE was measured by density measurements of DAPI nuclei in the whole white matter. Neuronal cells were quantified by counting the NeuN$^+$/β3-tubulin$^+$/DAPI$^+$ cells per mm2 in the whole gray matter. Both white and gray matter assessments occurred in the TI-IS spinal cord sections. Laser scanning confocal microscopic scans at 40× were performed on Mac 3$^+$/β3-tubulin$^+$ immunostained spinal cord sections corresponding to levels 11-15 ventral horn. The results for each experimental condition were averaged from four unilateral levels per mouse (100 pm apart, three mice in each treatment group, total of 12 sections per treatment group) and were expressed as mean fold change as compared to healthy matched controls, as described.

Statistical Analysis.

EAE clinical disease severity was compared between treatment groups using the Friedman test; histopathological changes were assessed using 1×4 ANOVAs; uterine weights, proliferative responses and cytokine levels were compared between treatment groups using Student t-test, and time on rotorod was compared between treatment groups using ANOVA.

Results. Selected Doses of ERα and ERβ Ligands Induced Known Biological Responses on a Positive Control Tissue, the Uterus.

Figure 11:
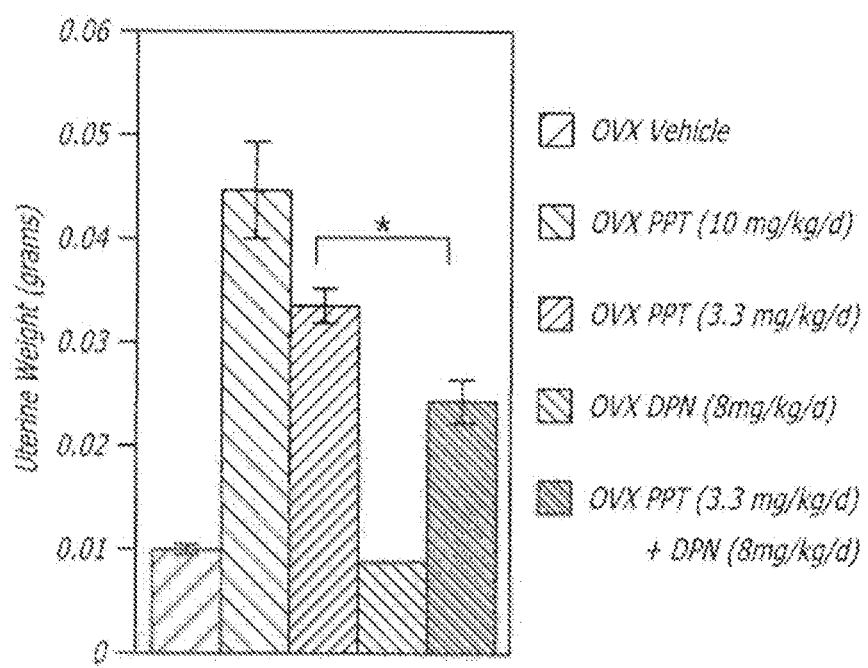
FIG. 11 is a bar graph showing the uterine weights of wild type (WT), estrogen receptor alpha ligand (PPT) and estrogen receptor beta ligand (DPN) treated animals (y-axis=uterine weight in grams).

Before beginning EAE experiments, the uterine response was used to assess whether a known in vivo response would occur during treatment with each of our dosing regimens. It was known that estrogen treatment increased uterine weight primarily though ERα, and it had also been shown that treatment with the ERβ ligand Diarylpropionitrile (DPN) could antagonize the ERα mediated increase in uterine weight. The ERα ligand propyl pyrazole triol (PPT) was given to ovariectomized C7BL/6 females for 10 days at either an optimal (10 mg/kg/day) or suboptimal (3.3 mg/kg/day) dose, and a significant increase in uterine weight as compared to vehicle treated was observed (FIG. 11). For the ERβ ligand DPN, a dose was selected which was shown to be neuroprotective in an animal model of global ischemia. When this DPN dose (8 mg/kg/day) was given in combination with PPT treatment, the increase in uterine weight mediated by PPT treatment was significantly reduced. Doses of the ERα and ERβ ligands induce known biological responses on a positive control tissue. C57BL/6 mice were ovariectomized, then treated for 10 days with indicated doses of ERα or ERβ ligands as daily subcutaneous injections to determine the effect of this dosing regimen on uterine weight. As shown in FIG. 11, uterine weight was increased with PPT treatments at both 10 mg/kg/day and 3.3 mg/kg/day, as compared to vehicle treated controls. Treatment with DPN alone at 8 mg/kg/day had no effect on uterine weight, while this DPN dose antagonized the PPT 3.3 mg/kg/day mediated increase in uterine weight. Each treatment group, n=4. * indicates p<0.05, student t-test.

These data demonstrated that the method and dose of delivery of the ERα and ERβ ligands induced a known biological response in vivo on a positive control tissue, the uterus.

Differential Effects of Treatment with ERα and ERβ Ligands on Clinical EAE.

We compared and contrasted effects between ERα and ERβ treatment during EAE. When the ERα ligand was administered one week prior to active EAE induction with MOG 35-55 peptide in ovariectomized C57BL/6 female mice, clinical disease as measured by the standard EAE grading scale was completely abrogated, p<0.0001 (FIG. 12A). This was consistent with our previously findings in this EAE model (described above), as well as findings in adoptive EAE in SJL mice by others. In contrast, ERβ ligand treatment had no significant effect early in disease (up to day 20 after disease induction), but then demonstrated a significant protective effect later in disease (after day 20), p<0.001 (FIG. 12B).

The protective effect using the ERβ ligand DPN in active EAE in C57BL/6 mice were surprising given that another ERβ ligand (WAY-202041) was shown to have no effect in adoptive EAE in SJL mice. Since WAY-202041 was shown to have a 200 fold selectivity for ERβ as compared to ERα, while DPN has a 70 fold selectivity, it was possible that DPN was not sufficiently selective for ERβ in vivo in our studies. To assess the in vivo selectivity of DPN during EAE, DPN was administered to ERβ KO mice. When OPN was administered to ovariectomized ERβ KO C57BL/6 mice with active EAE, the treatment was no longer protective (FIG. 12C). These data demonstrated the in vivo selectivity of DPN for ERβ during EAE at the dose used.

Together these data indicate that treatment with an ERα ligand is protective throughout the course of EAE, while treatment with an ERβ ligand is protective during the later phase of the disease, alter the acute initial phase.

Differential Effects of Treatment with ERα and ERβ Ligands on Autoantigen Specific Cytokine Production in C57BL/6 Mice with EAE.

Figure 12E:
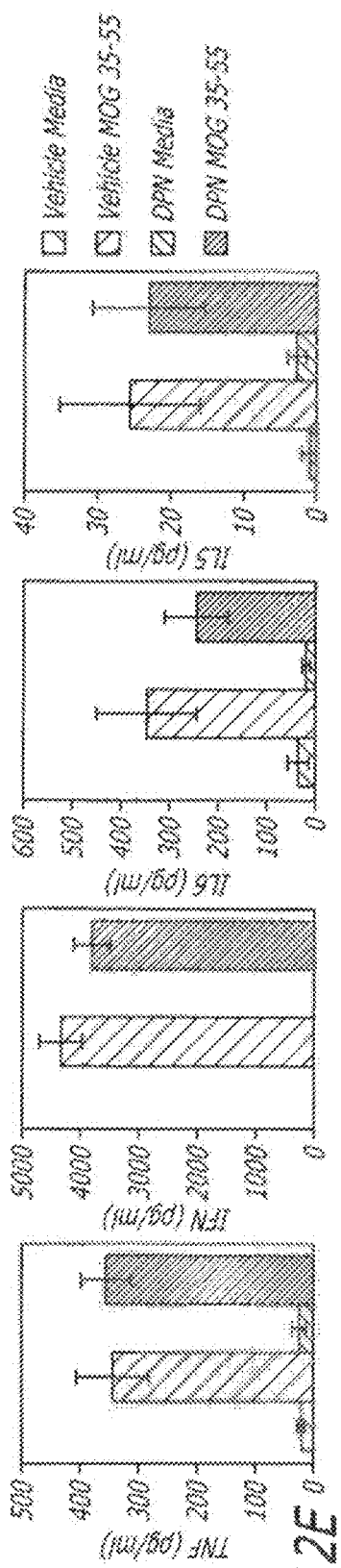

To further investigate differences between treatments with the ERα versus the ERβ ligand, the autoantigen specific cytokine production during both early and later stages of EAE in C57BL/6 mice was assessed. ERα ligand treatment significantly reduced levels of proinflammatory cytokines (TNFα, IFNγ, and IL6), while increasing the anti-inflammatory cytokine IL5, during both early (FIG. 12D) and later (FIG. 12F) stages of EAE. In contrast, ERβ ligand treatment was not statistically different from vehicle treatment in all measured cytokines (TNFα, IFNγ, and IL6, and IL5) at either the early (FIG. 12E) or later (FIG. 12G) time points. Treatment with ERα versus ERβ selective ligands has differential effects on chronic EAE and autoantigen specific immune responses in C57BL/6 mice. Ovariectomized C57BL/6 female mice were given daily subcutaneous injections of an ER ligand during active EAE and graded using the standard EAE grading scale. FIG. 12A, Mean clinical scores of PPT treated mice as compared to vehicle treated mice were significantly reduced during the entire disease course, p<0.0001, Friedman test. Each treatment group had an n=4, and data are representative of a total of five repeated experiments. FIG. 12B, DPN treated mice, as compared to vehicle treated mice, were not significantly different early in disease (up to day 20 after disease induction), but then became significantly improved later during EAE, (following day 30 after disease induction) p<0.001, Friedman test. Number of mice in each group were vehicle, n=4; estradiol, n=4; DPN, n=8. Data are representative of experiments repeated twice. DPN treatment in vivo during EAE remains highly selective for ERβ. Clinical scores in ovariectomized ERβ 1(0 C57BL/6 mice with active EAE were no different when comparing DPN treated with vehicle treated. Each treatment group had an n 4, and data are representative of experiments repeated twice. Estradiol treated mice served as a positive control for a treatment effect in each experiment (FIGS. 12A-C).

Figure 12F:
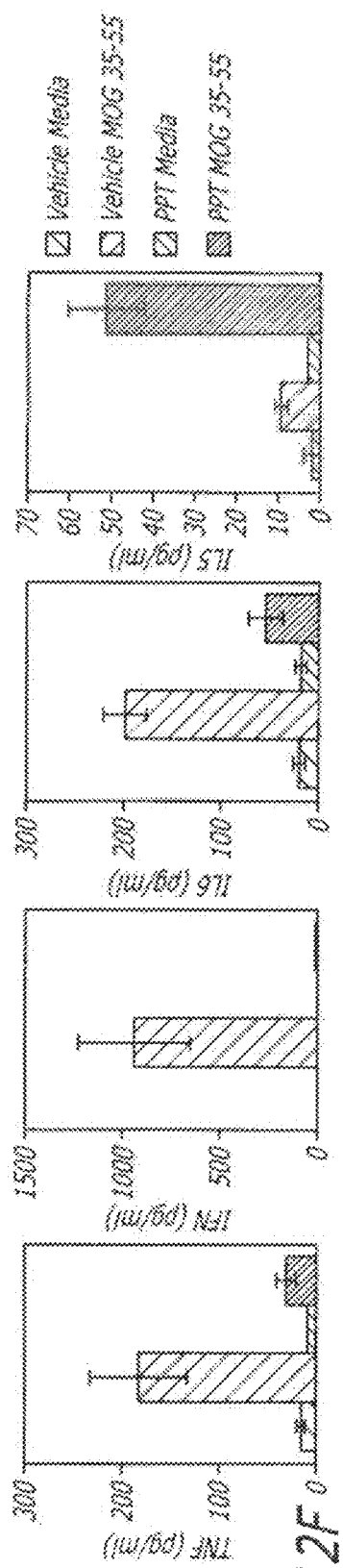
Figure 12G:
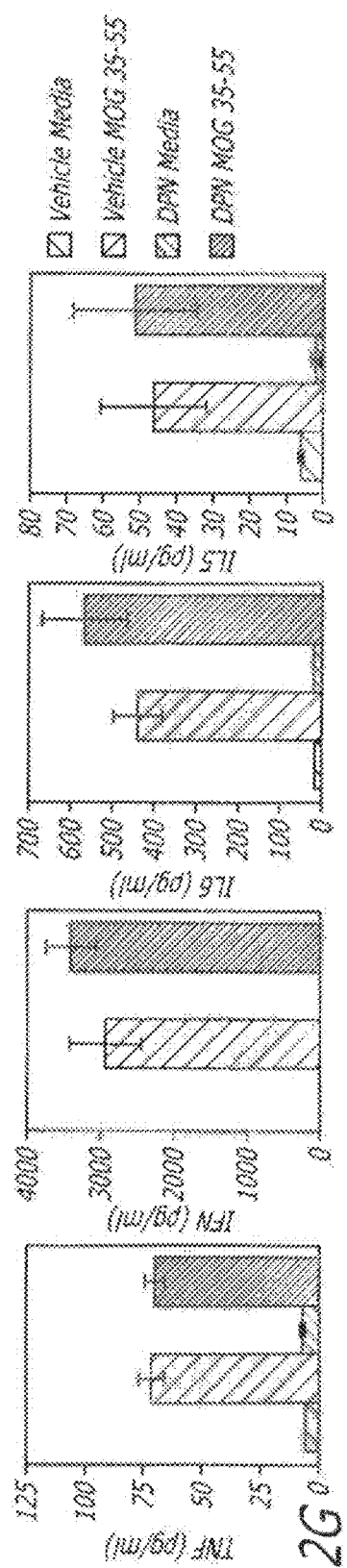

At day 19 (FIGS. 12D and 12E) or day 40 (FIGS. 12F and 12G) after disease induction, mice were sacrificed and cytokine production by MOO 35-55 stintulated splenocytes was determined. ITT treatment significantly reduced TNFα, LFNγ, and LL6, and increased LU during early EAE (FIG. 12D) and late EAE (FIG. 12F).

In contrast, no significant differences with DPN treatment were seen in measured cytokine levels at either the early stage (FIG. 12E) or late stage (1) of EAE disease. Error bars indicate variability of cytokine values for individual mice within a given treatment group, with n=4 mice for each treatment group. Data are representative of two to five experiments for each time point. (FIGS. 12D-G) No differences were observed with either ERα or ERβ ligand treatment, as compared to vehicle, for IL1O production, while 11,4 and 1L12 levels were too low to detect (not shown).

These results indicated that while ERα ligand treatment induced favorable changes in cytokine production during the autoantigen specific immune response, ERβ ligand treatment did not.

Treatment with an ERβ Ligand Reduces Clinical Relapses, but does not Alter Autoantigen Specific Immune Responses in SJL Mice with EAE.

Next, proteolipid protein (PLP) 139-151 induced active EAE in SJL mice were treated with either DPN or vehicle control. While there was no difference in the incidence, the day of onset, or the peak clinical scores, there was a significant decrease in relapses in DPN treated mice (5/13, 33%) as compared to vehicle treated (10/13, 77%), p<0.01. These relapses occurred between days 36 and 52 after disease induction. Notably, the previous report stating that the ERβ ligand WAY-202041 was not protective in EAE in SJL mice followed mice for only the first 27 days after disease induction, a duration including only the first episode of acute EAE, and a time when no effect of DPN treatment was observed.

The immune responses in this EAE model were then assessed. Since epitope spreading had been previously described in SJL mice with PLP 139-151 induced EAE, the immune response to the disease initiating autoantigen (PLP 139-151) was assessed, as well as the response to possible epitope spreading autoantigens (PLP 179-191 and MBP 83-102). There was no significant effect of ERβ legand treatment, as compared to vehicle treatment, on immune responses to the disease initiating autoantigen (FIGS. 13A-

C), and no epitope spreading occurred, even m vehicle treated EAE mice, consistent with some reports not detecting epitope spreading.

Figure 13A:
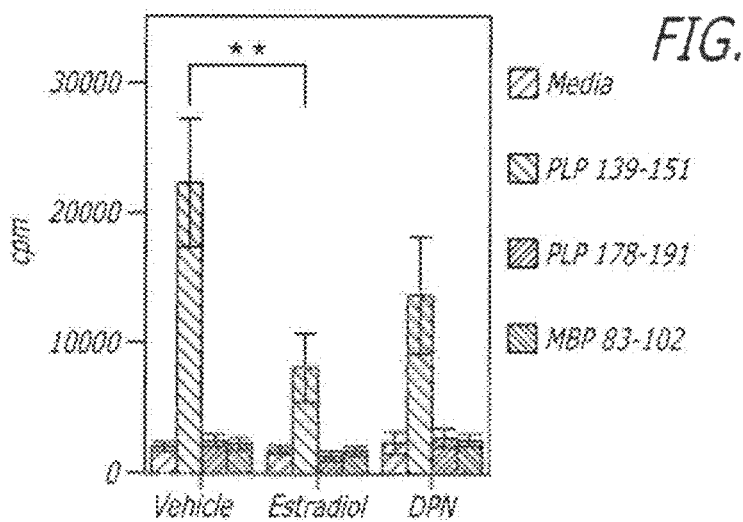
FIGS. 13A-C are bar graphs showing the effect of treatment with a estrogen receptor selective ligand (DPN), vehicle or estradiol on proliferation or cytokine production.
Figure 13B:
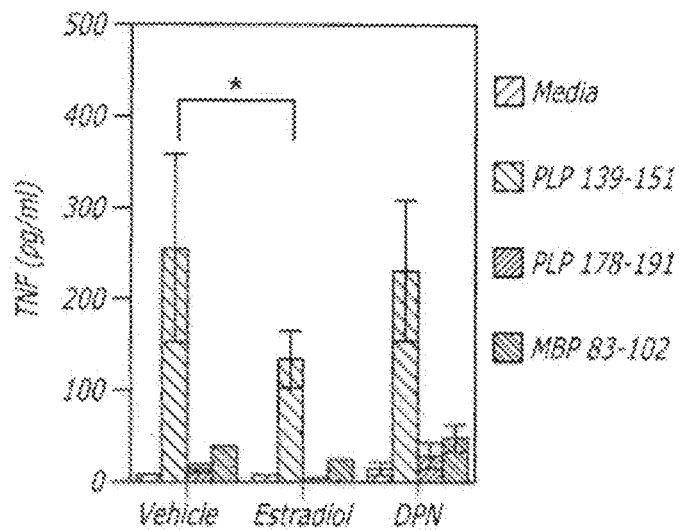
Figure 13C:
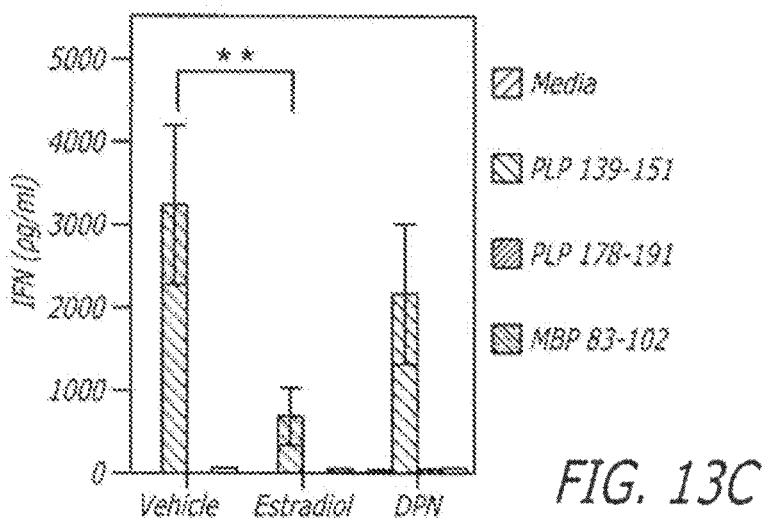

FIGS. 13A-C. Treatment with an ERβ selective ligand did not affect peripheral immune cells in SJL mice with EAE. Active EAE was induced with PLP 139-151 peptide in ovariectomized SJL female mice treated with either vehicle, DPN or estradiol. At day 52 after disease induction, mice were sacrificed and splenic immune responses to the disease initiating antigen (PLP 139-151), as well as to possible epitope spreading antigens (PLP 178-191 and MBP 83-102) were assessed. The only detectable response in all three treatment groups was to the disease initiating antigen (PLP 139-151), while responses to possible epitope spreading antigens were undetectable. No significant differences were observed in proliferation or cytokine (TNFα or LENγ) production during the PLP 139-151 specific response in the DPN treated group as compared to the vehicle treated group. Estradiol treatment served as the positive control for a treatment effect on immune responses, demonstrating decreases in the proliferative response, as well as in TNFα and IFNγ cytokine production, when compared to vehicle treated, consistent with previous reports. Error bars indicate variability of values for individual mice within a given treatment group, with n=4 mice for each treatment group, and data are representative of experiments repeated twice.

Together these data indicated that while ERβ ligand treatment mediated a reduction in relapses in SW mice with EAE, the mechanism for this effect on relapses did not include a significant effect on cytokine production or epitope spreading.

Treatment with an ERα Ligand, but not an ERβ Ligand, Reduces CNS Inflammation in EAE.

The comparison of the effect of ERα versus ERβ ligands in neuropathology was assessed. At both early (day 19) and later (day 40) stages of EKE, spinal cord sections from mice treated with either vehicle, ERα or ERβ ligand were assessed for inflammation and demyelination. On hemotoxylin and eosin (H&E) staining, vehicle treated C578L16 EAE mice had extensive white matter inflammation at both the early (FIG. 14A) and later (FIG. 14C) time points as compared to the healthy controls. As compared to vehicle treated EAE, this inflammation was significantly reduced by treatment with the ERα ligand PPT. In contrast, extensive white matter inflammation was present in the ERβ ligand treated group at both the early and late timepoints. Quantification of white matter cell density by counting DAPI+ cells revealed that ERα ligand treated mice at the early stage of EAE had a significant, p<0.001, reduction in inflammation in white matter of the thoracic cord as compared with vehicle treated EAE, while white matter cell densities in DPN treated EAE mice were not significantly different from those in vehicle treated, FIG. 14B. At the later time point, quantification revealed a lesser, but still significant, p<0.05, reduction in inflammation with ERα ligand treatment as compared to vehicle, while inflammation in ERβ ligand treated was no different from that in vehicle treated, FIG. 14D.

Double immunohistochemistry using anti-CD4S and anti-NIF200 antibodies was then used to stain inflammatory cells and axons, respectively. ERα ligand treated EAE mice, as compared to vehicle treated EAE, had less C045 staining in white matter. This reduction in C045 staining was most marked at the early time point in EAE (FIG. 14E), while at the later time point, some C045 staining was detectable in the ERα ligand treated, albeit still less than in vehicle treated (FIG. 14F). In contrast, ERβ ligand treated EAE mice did not have reduced CD45 staining in white matter, at either the early or the later time points.

Additionally, CD45 staining of cells in gray matter of vehicle treated EAE mice was observed at both the early and later time points, and these cells had a morphology suggestive of activated microglia (FIGS. 14E and F insets), ERα ligand treatment, but not ERβ ligand treatment, reduced this CD4S staining in gray matter.

Together these data indicated that ERα ligand treatment, but not ERβ ligand treatment, reduced inflammation in the CNS of mice with EAE. Notably, the lack of a reduction in CNS inflammation with ERβ ligand treatment was consistent with the lack of an immunomodulatory effect of ERβ ligand treatment on the autoantigen specific immune response in the periphery (FIG. 12).

Treatment with Both an ERα Ligand and an ERβ Ligand Reduces Demyelination and Axonal Transaction in White Matter in EAE.

Figure 17A:
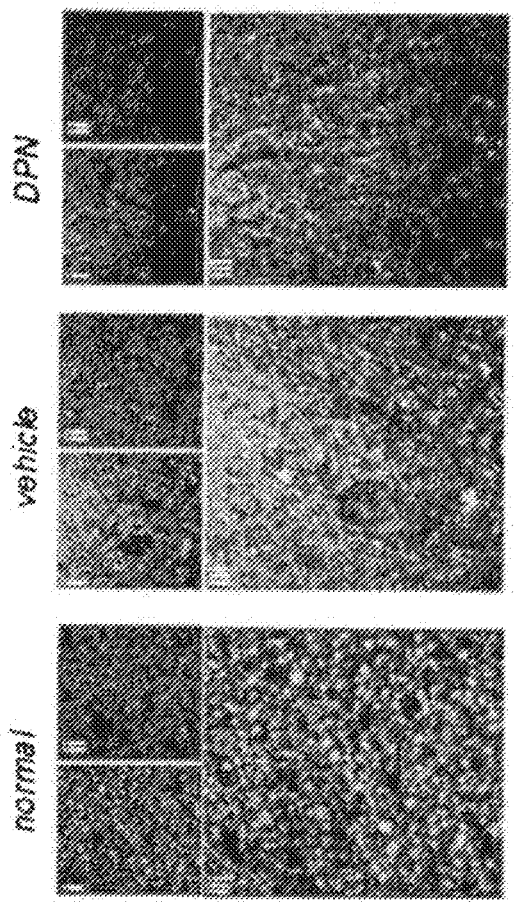
FIGS. 17A-B are images of thoracic spinal cord sections stained derived from ERβ knock out control mice, vehicle-treated mice with EAE, and DPN-treated mice with EAE.
Figure 17B:
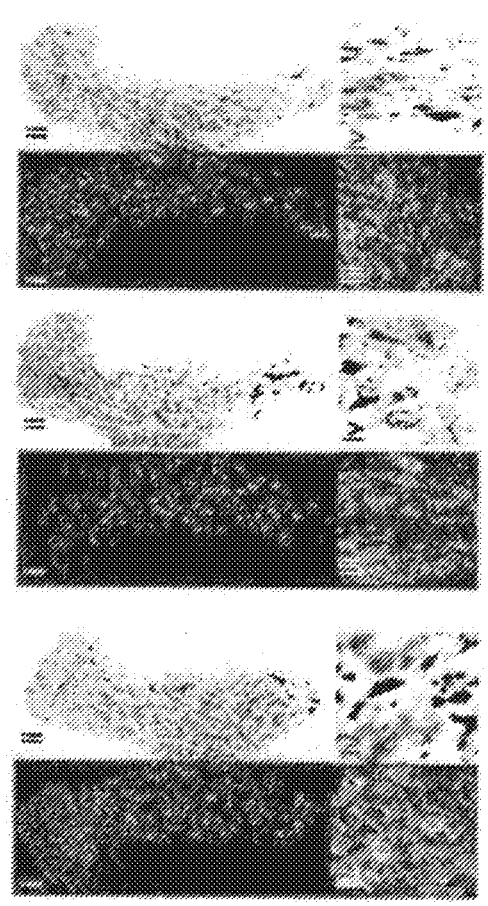
Figure 17C:
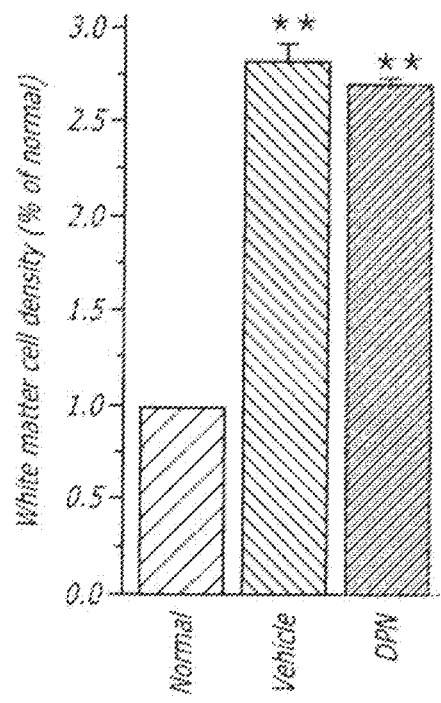
FIGS. 17C-F depict quantification of white matter cell density, myelin density, axonal numbers and NeuN+ cells in control mice, vehicle-treated mice with EAE, and DPN-treated mice with EAE.
Figure 17D:
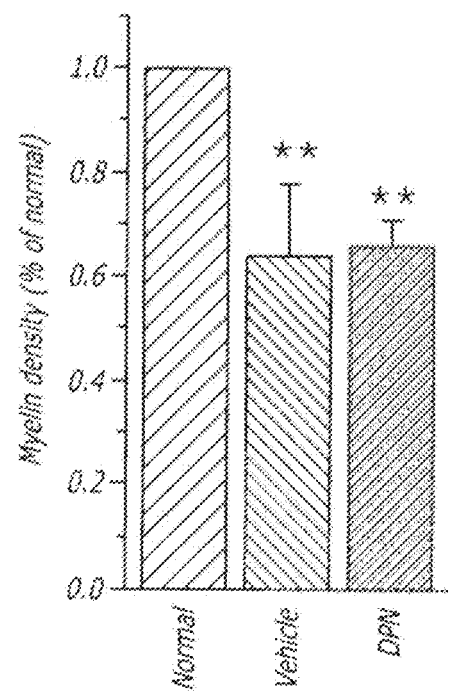
Figure 17E:
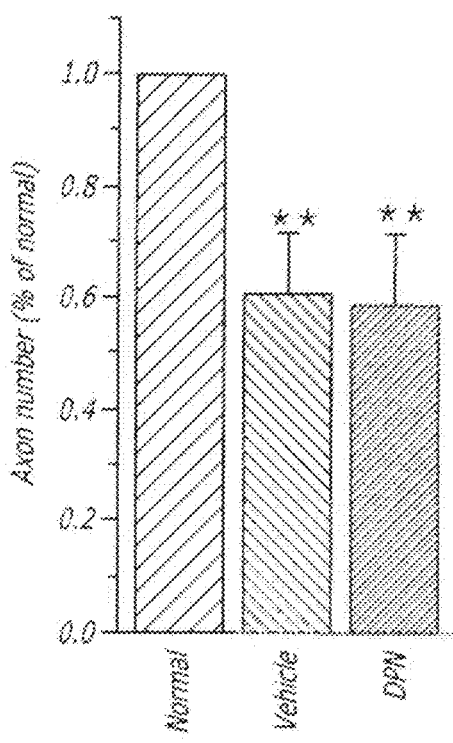
Figure 17F:
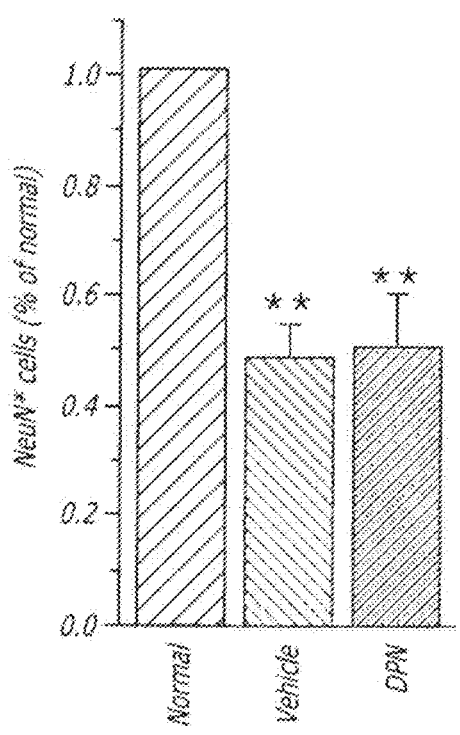

The degree of myelin loss was then assessed by myelin basic protein (MBP) immunostaining in the dorsal columns of thoracic cords. Extensive demyelination occurred at the sites of inflammatory cell infiltrates in vehicle treated EAE mice while less demyelination occurred in ERα and ERβ ligand treated (FIGS. 15A and 15C). Quantification of demyelination by density analysis of MBP immunostained spinal cord sections revealed a 32% (p<0.01) and 34% (p<0.005) decrease in myelin density in vehicle treated EAE mice, at the early and later time points, respectively, as compared to normal controls (FIGS. 17B and 17D). Myelin staining was relatively preserved in both ERα and ERβ ligand treated mice, at both the early and later time points in disease, with reductions ranging from 7-19%, not significantly different than healthy controls.

Staining with anti-NF200 antibody revealed axonal loss in white matter of vehicle treated mice at both early and later time points of disease as compared to normal controls, while both ERα ligand and ERβ ligand treatment resulted in less axonal loss, as compared to that in vehicle treated EAE mice (FIGS. 15E and 15G). Quantification of NF200 staining in anterior fununculus revealed a 49±12% (p<0.01) and 40±8% (p<0.005) reduction in vehicle treated EAE, at the early and later time points, respectively, as compared to healthy controls (FIGS. 15F and 15H) Axon numbers in ERα ligand and ERβ ligand treated EAE mice were not significantly reduced as compared to those in healthy controls.

FIG. 15. Treatment with an ERα ligand and an ERβ ligand each preserved myelin basic protein immunoreactivity and spared axonal pathology in white matter of spinal cords of mice with EAE. Dorsal columns of thoracic spinal cord sections were imaged at lox magnification from mice in FIG. 14 that were immunostained with antiMBP (red). At day 19 (FIG. 15A) and day 40 (FIG. 15C) after disease induction, vehicle treated mice had reduced MBP immunoreactivity as compared to normal controls, while PPT treated EAE and DPN treated EAE mice showed relatively preserved MBP staining. Upon quantification (FIGS. 15B and 15D), MBP immunoreactivity in dorsal column was significantly lower in vehicle treated EAE mice as compared to normal mice, while PPT and DPN treated EAE mice demonstrated no significant decreases. Myelin density is presented as percent of normal. Statistically significant compared with normal (*p<0.01; p<0.005), 1×4 ANOVAs.

Part of the anterior funniculus of thoracic spinal cord sections was imaged at 40× magnification from mice in FIG. 15 that were co-immunostained with anti-NF200 (green, i) and anti-MBP (red, ii). Merged images of smaller (i) and (ii)

panels are shown in (iii). Distinct green axonal centers surrounded by red myelin sheaths can be seen in normal controls, PPT and DPN treated EAE mice from 19 day (FIG. 15E) and 40 day (FIG. 15G) after disease induction. Vehicle treated mice show reduced axonal numbers and myelin, along with focal demyelination (white stars) and loss of axons. Upon quantification (FIGS. 15F and 15H), neurofilament stained axon numbers in white matter were significantly lower in vehicle treated EAE mice as compared to normal mice, while PPT and DPN treated EAE mice demonstrated no significant reduction in axon numbers. Axon number is presented as percent of normal. Statistically significant compared with normal (*$p<0.01$; **$p<0.005$), 1×4 ANOVAs.

Together these data demonstrated that ERα ligand treatment reduced inflammation, demyelination and axonal transection in white matter during EAE, while ERβ ligand treatment did not reduce inflammation, but nevertheless still was capable of reducing demyelination and axonal transection.

Treatment with both an ERα ligand and an ERβ ligand reduces neuronal pathology in gray mailer of mice with EAE.

In Example 5 above, we demonstrated neuronal abnormalities surprisingly early during EAE (day 15), which were prevented by treatment with either estradiol or PPT. Whether ERβ ligand treatment might preserve neuronal integrity at both the early (day 19) and later (day 40) time points of EAE was examined. Using a combination of Nissl stain histology and anti NeuN/β3-tubulin immunolabeling of neurons in gray matter were identified and quantified, at both the early and later time points in EAE. A decrease in neuronal staining in gray matter occurred at both time points in vehicle treated EAE mice as compared to normal controls, while neuronal staining in gray matter was well preserved in EAE mice treated with either the ERα or the ERβ ligand at the early and the later time points (FIGS. 16A and 16C). Quantification of NeuN$^+$ cells in gray matter demonstrated a 41±13% ($p<0.05$) and 31±8% ($p<0.05$) reduction, at the early and later time points respectively, in vehicle treated EAE mice as compared to normal controls, while PPT and DPN treated mice had NeuN$^+$ cell numbers that were fewer, but not significantly different from those in healthy controls (FIGS. 16B and 16D).

FIG. 16. Treatment with an ERα ligand and an ERI3 ligand each preserved neuronal staining in gray matter of spinal cords of mice with EAE. Split images of thoracic spinal cord sections stained with NeuN$^+$ (red) in (i) and Nissl in (ii) at 4× magnification, derived from normal healthy control mice, vehicle treated EAE, ERα ligand (PPT) treated EAE and ERβ ligand (DPN) treated EAE mice, each sacrificed at either day 19 (early; FIG. 16A) or at day 40 (late; FIG. 16C) after disease induction. Panel (iii) is a merged confocal scan at 40× of NeuN$^+$ (red) and (33-tubulin+ (green) co-labeled neurons from an area represented by dotted white square area in (i). Panel (iv) is a 40× magnification of Nissl stained area in solid black square in (ii). A decrease in NeuN$^+$ immunostaining and Nissl staining was observed in the dorsal horn, intermediate zone and ventral horn of vehicle treated EAE mice as compared to normal control. White arrows in panel (iii) denote loss of NeuN$^+$ staining. In contrast, EAE mice treated with either PPT or DPN had preserved NeuN and Nissl staining. Upon quantification of neurons in the entire delineated gray matter of T1-T5 sections, NeuN$^+$ immunolabeled neurons were significantly decreased, by nearly 41%, in vehicle treated EAE mice at day 19 (FIG. 16B) and nearly 31% at day 40 (FIG. 16D) as compared to normal controls, while PPT and DPN treated EAE mice were not statistically different from normal controls. Number of mice 3 per treatment group, number of T1-T5 sections per mouse=6, total number of sections per treatment group=18. Statistically significant compared with normals (*$p<0.05$), 1×4 ANOVAs. Data are representative of experiments repeated in their entirety on another set of EAE mice with each of the treatments.

Protection from neuropathology is mediated by ERβ.

To confirm whether the effect of DPN treatment in vivo on CNS neuropathology was indeed mediated through ERβ, we next assessed white and gray matter neuropathology in DPN treated EAE mice deficient in ERβ. At day 38 after disease induction, inflammation, demyelination and reductions in axon numbers were present in white matter, while neuronal staining was decreased in gray matter of vehicle treated EAE mice (FIG. 17). In contrast to the preservation of myelin, axon numbers and neuronal staining observed during DPN treatment of wild type mice (FIGS. 15 and 16), DPN treatment of ERβ knock out mice failed to prevent this white and gray matter pathology (FIG. 17).

FIG. 17. DPN treatment mediated protection from neuropathology during EAE is dependent upon ERβ. As shown in FIG. 17A, part of the anterior funniculus of thoracic spinal cord sections from ERβ knock out control mice, vehicle treated EEβ knock out with EAE and DPN treated ERβ knock out with EAE at day 40 after disease induction were imaged at 40× magnification upon co-immunostaining with anti-NF200 (green, i) and anti-MBP (red, ii). Merged images are shown in panel iii. ERβ knock out control sections showed robust NF200 and MBP immunostaining similar to wild type normal controls in FIG. 18, whereas vehicle and DPN treated EAE sections had decreased myelin and axonal staining. FIG. 17B shows split images of thoracic spinal cord sections, derived from mice in FIG. 17A, stained with NeuN (red) in (i) and Nissl in (ii) at 4× magnification, showed neuronal losses in gray matter of both the vehicle treated and DPN treated ERβ knock out mice with EAE. (FIGS. 17C-F) Quantification of white matter cell density, myelin density, axonal numbers and NeuN$^+$ cells revealed that DPN treatment does not prevent white and gray matter pathology during EAE in ERβ knock out mice. Number of mice=3 per treatment group, number of T1-T5 sections per mouse=6, total number of sections per treatment group=18. Statistically significant compared with normals (**$p<0.001$), 1×4 ANOVAs. These data demonstrate that direct neuroprotective effects mediated by DPN treatment in vivo during EAE are mediated through ERβ.

Treatment with an ERβ Ligand Induces Recovery of Motor Performance.

Figure 18A:
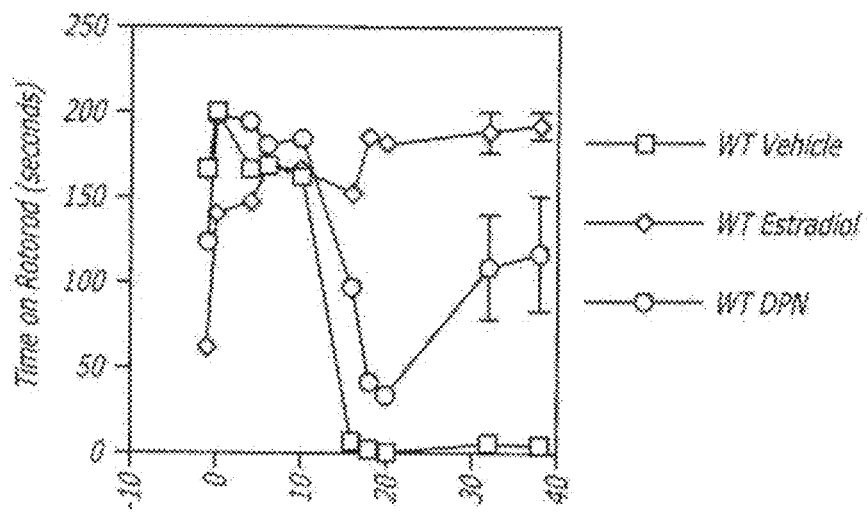
FIGS. 18A-B depict results in recovery of motor function during EAE in control, vehicle-treated, and DPN-treated mice.

Since treatment with an ERβ ligand was found to be neuroprotective in EAE, the clinical significance of this neuroprotective effect was assessed. The clinical outcome frequently used in spinal cord injury, rotarod performance was used. Vehicle treated C57BL/6 EAE mice demonstrated an abrupt and consistent decrease in the number of seconds they were able to remain on the rotarod, beginning at day 12 after disease induction (FIG. 18A). This disability remained throughout the remainder of the observation period in vehicle treated EAE mice. In contrast, ERβ ligand treated mice had an abrupt decrease in the number of seconds they could remain on the rotarod apparatus, beginning at day 12, but later during EAE, at days 30-40, they had significant recovery of their ability to remain on the rotarod. These data demonstrated that ERβ ligand treatment induces functional clinical recovery in motor performance at later time points of disease during EAE.

Finally, to assess whether the improvement in rotarod performance with DPN treatment was mediated through ERβ, rotarod performance studies were conducted in ERβ KO female mice. The improvement in rotarod performance late during EKE with DPN treatment was no longer observed in the ERβ KO (FIG. 18B).

Figure 18B:
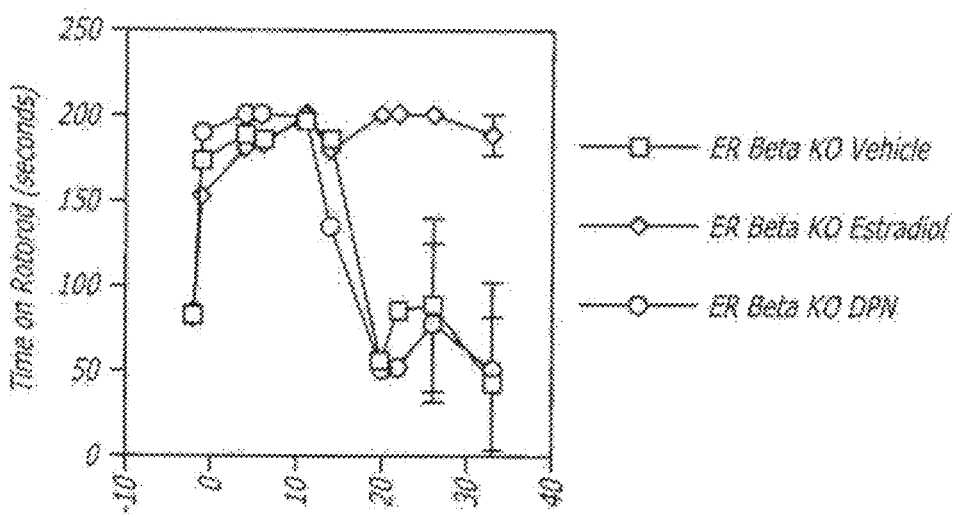

FIG. 18. Treatment with an ERβ selective ligand results in recovery of motor function late during EAE. Ovariectonized C57BL/6 female mice with EAE were treated with DPN and assessed for motor performance on a rotarod apparatus. As shown in FIG. 18A, while mean time on rotarod decreased abruptly at day 12 after disease induction in both the vehicle and DPN treated EAE mice, after day 30 the DPN treated group demonstrated significant recovery of motor function, while the vehicle treated did not improve. *$p<0.01$ and ** $p<0.005$, ANOVA. Estradiol treatment served as a positive control for a treatment effect. Number of mice in each treatment group, vehicle n=4; DPN n=8; estradiol n=4. Data are representative of experiments repeated twice. As shown in FIG. 18B, in contrast to the improvement observed with DPN treatment of wild type mice, no improvement was observed at the later phase of disease in DPN treated ERβ KO mice. Again, vehicle served as a negative control, and estradiol served as a positive control, for a treatment effect. Number of mice in each treatment group, vehicle n=4; DPN n=4; estradiol n=4.

These data demonstrated that the DPN induced recovery in motor performance later in disease was mediated through ERβ.

In closing, it is noted that specific illustrative embodiments of the invention have been disclosed herein above. However, it is to be understood that the invention is not limited to these specific embodiments.

Accordingly, the invention is not limited to the precise embodiments described in detail hereinabove. With respect to the claims, it is applicant's intention that the claims not be interpreted in accordance with the sixth paragraph of 35 U.S.C. Section 112 unless the term "means" is used followed by a functional statement.

While the specification describes particular embodiments of the present invention, those of ordinary skill can devise variations of the present invention without departing from the inventive concept.

I claim:

1. A method of reducing motor impairment in a subject suffering from multiple sclerosis, comprising administering to the subject an effective amount of

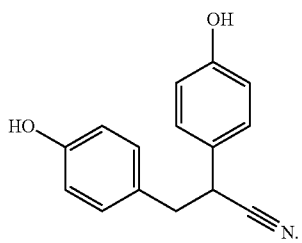

2. The method of claim 1, wherein the method treats multiple sclerosis.
3. The method of claim 1, wherein the method reduces clinical relapses.
4. The method of claim 1, wherein the method reduces demyelination or axonal transection.
5. The method of claim 1, wherein the method promotes recovery of motor performance.
6. The method of claim 1, wherein the method further comprises conjoint administration of an effective amount of a secondary agent to the subject.
7. The method of claim 6, wherein the secondary agent is a glucocorticoid.
8. The method of claim 6, wherein the secondary agent is prednisone or methyl prednisone.
9. The method of claim 6, wherein the secondary agent is selected from beta-interferon, glatiramer acetate copolymer-1, azathioprine, cyclophosphamide, methotrexate, mitoxantrone and cyclosporin A.
10. The method of claim 6, wherein the beta-interferon is interferon-beta 1a or interferon-beta 1b.
11. The method of claim 1, wherein the subject is a human female.
12. A method of reducing motor impairment in a subject suffering from multiple sclerosis, comprising delivering to the brain of the subject an effective amount of

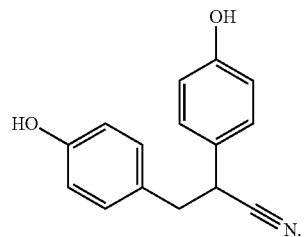 [SMILES: N#CC(Cc1ccc(O)cc1)c1ccc(O)cc1]

13. The method of claim 12, wherein the method reduces clinical relapses.
14. The method of claim 12, wherein the method reduces demyelination or axonal transection.
15. The method of claim 12, wherein the method promotes recovery of motor performance.
16. The method of claim 12, wherein the method further comprises conjoint administration of an effective amount of a secondary agent to the subject.
17. The method of claim 16, wherein the secondary agent is a glucocorticoid.
18. The method of claim 16, wherein the secondary agent is prednisone or methyl prednisone.
19. The method of claim 16, wherein the secondary agent is selected from beta-interferon, glatiramer acetate copolymer-1, azathioprine, cyclophosphamide, methotrexate, mitoxantrone and cyclosporin A.
20. The method of claim 16, wherein the beta-interferon is interferon-beta 1a or interferon-beta 1b.
21. The method of claim 12, wherein the subject is a human female.

* * * * *